US012594290B2

(12) United States Patent
Perello Bestard et al.

(10) Patent No.: US 12,594,290 B2
(45) Date of Patent: Apr. 7, 2026

(54) IP AND IP ANALOGS DOSAGE REGIMENS FOR THE TREATMENT OF ECTOPIC CALCIFICATIONS

(71) Applicant: SANIFIT THERAPEUTICS S.A., Palma de Mallorca (ES)

(72) Inventors: Joan Perello Bestard, Palma de Mallorca (ES); Carolina Salcedo Roca, Palma de Mallorca (ES); Ana-Zeralda Canals Hamann, Palma de Mallorca (ES)

(73) Assignee: SANIFIT THERAPEUTICS S.A., Palma de Mallorca (ES)

( * ) Notice: Subject to any disclaimer, the term of this patent is extended or adjusted under 35 U.S.C. 154(b) by 0 days.

(21) Appl. No.: 19/065,860

(22) Filed: Feb. 27, 2025

(65) Prior Publication Data

US 2025/0302853 A1 Oct. 2, 2025

Related U.S. Application Data

(60) Continuation of application No. 18/778,767, filed on Jul. 19, 2024, now abandoned, which is a continuation of application No. 17/192,609, filed on Mar. 4, 2021, now Pat. No. 12,070,469, which is a division of application No. 16/791,808, filed on Feb. 14, 2020, now Pat. No. 10,973,838, which is a continuation of application No. PCT/IB2018/057904, filed on Oct. 11, 2018.

(30) Foreign Application Priority Data

Oct. 11, 2018 (ES) ................................ ES201830988

(51) Int. Cl.
| | |
|---|---|
| *A61K 31/7024* | (2006.01) |
| *A61K 9/00* | (2006.01) |
| *A61K 31/661* | (2006.01) |
| *A61K 31/6615* | (2006.01) |
| *A61K 31/7032* | (2006.01) |
| *A61P 9/00* | (2006.01) |
| *A61P 17/02* | (2006.01) |
| *A61P 19/08* | (2006.01) |

(52) U.S. Cl.
CPC ........ *A61K 31/7024* (2013.01); *A61K 9/0014* (2013.01); *A61K 9/0019* (2013.01); *A61K 31/6615* (2013.01); *A61K 31/7032* (2013.01); *A61P 9/00* (2018.01); *A61P 17/02* (2018.01); *A61P 19/08* (2018.01)

(58) Field of Classification Search
CPC ............ A61K 31/7024; A61K 31/6615; A61K 31/7032; A61K 31/661; A61P 9/00; A61P 17/02; A61P 19/08
See application file for complete search history.

(56) References Cited

U.S. PATENT DOCUMENTS

| | | | |
|---|---|---|---|
| 3,159,581 | A | 12/1964 | Diehl |
| 3,488,419 | A | 1/1970 | Mccune et al. |
| 3,934,001 | A | 1/1976 | Watson |
| 3,934,002 | A | 1/1976 | Haefele |
| 4,024,175 | A | 5/1977 | Satzinger et al. |
| 4,215,105 | A | 7/1980 | Gaffar et al. |
| 4,259,316 | A | 3/1981 | Nakashima et al. |
| 4,515,772 | A | 5/1985 | Parran, Jr. et al. |
| 4,627,977 | A | 12/1986 | Gaffar et al. |
| 4,752,586 | A | 6/1988 | Ropars et al. |
| 4,808,401 | A | 2/1989 | Gaffar et al. |
| 4,826,675 | A | 5/1989 | Gaffar et al. |
| 4,952,568 | A | 8/1990 | Sawai et al. |
| 5,007,790 | A | 4/1991 | Shell |
| 5,015,634 | A | 5/1991 | Siren |
| 5,041,429 | A | 8/1991 | Sawai et al. |
| 5,057,507 | A | 10/1991 | Siren |
| 5,082,833 | A | 1/1992 | Shamsuddin |
| 5,112,814 | A | 5/1992 | Sabin |
| 5,206,226 | A | 4/1993 | Sabin |
| 5,268,176 | A | 12/1993 | Znaiden et al. |
| 5,300,289 | A | 4/1994 | Garlich et al. |
| 5,330,979 | A | 7/1994 | Siren et al. |

(Continued)

FOREIGN PATENT DOCUMENTS

| | | |
|---|---|---|
| CA | 2975801 A1 | 2/2010 |
| CN | 1295862 A | 5/2001 |

(Continued)

OTHER PUBLICATIONS

Angelis, M., et al., "Calciphylaxis in patients on hemodialysis: a prevalence study," Surgery 122(6): 1083-1090, Elsevier, Netherlands (Dec. 1997).

Augustin, M., et al. "Quality-of-life evaluation in chronic wounds: comparative analysis of three disease-specific questionnaires," International Wound Journal 14(6): 1299-1304, John Wiley, United States (Dec. 2017).

Avogaro, A., and Fadini, G. P., "Mechanisms of ectopic calcification: implications for diabetic vasculopathy," Cardiovascular Diagnosis and Therapy 5(5): 343-52, AME Publishing Company, China (Oct. 2015).

(Continued)

*Primary Examiner* — Kamal A Saeed
*Assistant Examiner* — Sagar Patel
(74) *Attorney, Agent, or Firm* — STERNE, KESSLER, GOLDSTEIN & FOX P.L.L.C.; Jaume M. Canaves

(57) ABSTRACT

The present disclosure related to compositions, methods, dosages, dosage regimens, articles of manufacture and kits for the treatment and/or prevention ectopic calcifications, and in particular cutaneous calcifications such as calciphylaxis calcifications comprising inositol phosphate, inositol phosphate analogs, inositol phosphate derivatives, or combinations thereof. In a particular aspect the disclosure provides a dosage regimen to treat calciphylaxis comprising the administration of 6 mg/kg to 9 mg/kg daily doses of myo-inositol hexaphosphate, three times a week, for at least 1 to 8 months.

21 Claims, 14 Drawing Sheets

(56) References Cited

U.S. PATENT DOCUMENTS

| | | | |
|---|---|---|---|
| 5,362,886 | A | 11/1994 | Berglund |
| 5,516,801 | A | 5/1996 | Horrobin et al. |
| 5,552,148 | A | 9/1996 | Znaiden et al. |
| 5,582,837 | A | 12/1996 | Shell |
| 5,821,237 | A | 10/1998 | Bissett et al. |
| 5,972,389 | A | 10/1999 | Shell et al. |
| 6,121,243 | A | 9/2000 | Lanzendorfer et al. |
| 6,340,475 | B2 | 1/2002 | Shell et al. |
| 6,359,194 | B1 | 3/2002 | Galvin et al. |
| 6,451,808 | B1 | 9/2002 | Cowles |
| 6,488,962 | B1 | 12/2002 | Berner et al. |
| 6,610,702 | B2 | 8/2003 | Lehn et al. |
| 8,277,909 | B2 | 10/2012 | Simpson et al. |
| 8,377,909 | B2 | 2/2013 | Grases Freixedas et al. |
| 8,778,912 | B2 | 7/2014 | Grases Freixedas et al. |
| 9,155,750 | B2 | 10/2015 | Grases Freixedas et al. |
| 9,358,243 | B2 | 6/2016 | Castagner et al. |
| 9,364,490 | B2 | 6/2016 | Perello Bestard et al. |
| 9,612,250 | B2 | 4/2017 | Perello Bestard et al. |
| 9,629,872 | B2 | 4/2017 | Ratsimbazafy et al. |
| 9,751,903 | B2 | 9/2017 | Castagner et al. |
| 10,010,559 | B2 | 7/2018 | Perello Bestard et al. |
| 10,076,481 | B2 | 9/2018 | Kleinberg et al. |
| 10,624,909 | B2 | 4/2020 | Ivarsson et al. |
| 10,744,233 | B2 | 8/2020 | Taton |
| 10,973,838 | B2 | 4/2021 | Perello Bestard et al. |
| 12,070,469 | B2 | 8/2024 | Perello Bestard et al. |
| 2002/0051820 | A1 | 5/2002 | Shell et al. |
| 2003/0039688 | A1 | 2/2003 | Shell et al. |
| 2003/0044466 | A1 | 3/2003 | Markey et al. |
| 2003/0104053 | A1 | 6/2003 | Gusler et al. |
| 2003/0104062 | A1 | 6/2003 | Berner et al. |
| 2003/0119910 | A1 | 6/2003 | Kamiya et al. |
| 2003/0147952 | A1 | 8/2003 | Lim et al. |
| 2006/0241086 | A1 | 10/2006 | Nicolau et al. |
| 2007/0066574 | A1 | 3/2007 | Grases Freixedas |
| 2007/0148258 | A1 | 6/2007 | O'Neill et al. |
| 2007/0212449 | A1 | 9/2007 | Shamsuddin et al. |
| 2007/0219115 | A1 | 9/2007 | Coleman et al. |
| 2010/0113613 | A1 | 5/2010 | Mclaurin et al. |
| 2011/0091440 | A1 | 4/2011 | Sabin |
| 2011/0172194 | A1 | 7/2011 | Grases et al. |
| 2011/0293595 | A1 | 12/2011 | Sabin |
| 2012/0101069 | A1 | 4/2012 | Moeddel et al. |
| 2013/0302448 | A1 | 11/2013 | Parc |
| 2014/0271915 | A1 | 9/2014 | Perello Bestard et al. |
| 2016/0280727 | A1 | 9/2016 | Castagner et al. |
| 2017/0020903 | A1 | 1/2017 | Perello et al. |
| 2017/0119799 | A1 | 5/2017 | Grases Freixedas et al. |
| 2017/0360810 | A1 | 12/2017 | Perello Bestard et al. |
| 2019/0091375 | A1 | 3/2019 | Taton |
| 2019/0167702 | A1 | 6/2019 | Perello Bestard et al. |
| 2020/0179422 | A1 | 6/2020 | Perello Bestard et al. |
| 2022/0000889 | A1 | 1/2022 | Bassissi et al. |
| 2022/0249521 | A1 | 8/2022 | Perello Bestard et al. |
| 2022/0339171 | A1 | 10/2022 | Perello Bestard et al. |
| 2023/0248749 | A1 | 8/2023 | Bassissi et al. |
| 2024/0066042 | A1 | 2/2024 | Perello Bestard et al. |
| 2025/0295676 | A1 | 9/2025 | Perello Bestard et al. |

FOREIGN PATENT DOCUMENTS

| | | | |
|---|---|---|---|
| CN | 1593376 | A | 3/2005 |
| DE | 29910454 | U1 | 9/1999 |
| EP | 1203535 | A1 | 5/2002 |
| EP | 2324835 | A2 | 5/2011 |
| EP | 2974714 | A1 | 1/2016 |
| EP | 3407891 | A1 | 12/2018 |
| GB | 2055574 | A | 3/1981 |
| WO | WO-9011757 | A1 | 10/1990 |
| WO | WO-1991009601 | A1 | 7/1991 |
| WO | WO-9318755 | A1 | 9/1993 |
| WO | WO-9747285 | A1 | 12/1997 |
| WO | WO-9811879 | A1 | 3/1998 |
| WO | WO-9855107 | A1 | 12/1998 |
| WO | WO-0113933 | A2 | 3/2001 |
| WO | WO-0124830 | A2 | 4/2001 |
| WO | WO-0132217 | A2 | 5/2001 |
| WO | WO-0156544 | A2 | 8/2001 |
| WO | WO-0197783 | A1 | 12/2001 |
| WO | WO-0209723 | A2 | 2/2002 |
| WO | WO-0210177 | A1 | 2/2002 |
| WO | WO-0232416 | A2 | 4/2002 |
| WO | WO-0296404 | A1 | 12/2002 |
| WO | WO-0335029 | A1 | 5/2003 |
| WO | WO-0335039 | A1 | 5/2003 |
| WO | WO-0335040 | A1 | 5/2003 |
| WO | WO-0335041 | A1 | 5/2003 |
| WO | WO-0335177 | A2 | 5/2003 |
| WO | WO-2004015084 | A2 | 2/2004 |
| WO | WO-2005044278 | A1 | 5/2005 |
| WO | WO-2007023306 | A1 | 3/2007 |
| WO | WO-2013050603 | A1 | 4/2013 |
| WO | WO-2017098033 | A1 | 6/2017 |
| WO | WO-2017098047 | A1 | 6/2017 |
| WO | WO-2017131127 | A1 | 8/2017 |
| WO | WO-2020074944 | A1 | 4/2020 |
| WO | WO-2020157362 | A1 | 8/2020 |
| WO | WO-2021094331 | A1 | 5/2021 |

OTHER PUBLICATIONS

Bhambri, A., and Del Rosso, J. Q., "Calciphylaxis: a review," Journal of Clinical and Aesthetic Dermatology 1(2): 38-41, Matrix Mexical Communications, United States (Jul. 2008).

Brandenburg, V., et al. "Fo020 A Phase 2 Open-Label Single-Arm Study To Assess The Effect Of Snf472 On Wound Healing In Calciphylaxis (Calcific Uremic Arteriolopathy) Patients," Nephrology Dialysis Transplantation 33(suppl_1): i9-i9, Oxford University Press, United Kingdom (May 2018).

Brandenburg, V., et al., "Phase 2 Open Label Single Arm Repeat Dose Study To Assess The Effect Of SNF472 On Wound Healing In Uraemic Calciphylaxis Patients," Sepsis 1: 8-3, Kluwer Academic Publishers, Netherlands (May 2017).

Brater, D. C., "Measurement of renal function during drug development," British Journal of Clinical Pharmacology 54(1):87-95, Blackwell Science Ltd., United Kingdom (Jul. 2002).

Budisavljevic, M. N., et al., "Calciphylaxis in chronic renal failure," Journal of the American Society of Nephrology 7(7): 978-982, American Society of Nephrology, United States (Jul. 1996).

Costa-Bauza, A., et al., "An experimental study on residual lithiasis after shock wave lithotripsy," Urological Research 33(1):51-56, Springer-Verlag, Germany (Feb. 2005).

Davita, "Kidney Stones and Chronic Kidney Disease," accessed at http://www.davita.com/kidney-disease/overview/symptoms-and-diagnosis/kidney-stones-a, accessed on Nov. 5, 2015, 2 pages.

Dolhofer, R. and Wieland, O. H., "Enzymatic assay of myo-inositol in serum," Journal of Clinical Chemistry and Clinical Biochemistry 25(10):733-736, Walter De Gruyter & Co., Germany (1987).

Espacenet, English-language Machine Translation of German Patent DE29910454 (cited herewith as FP1), performed on Apr. 24, 2017, 7 pages.

Fine, A., and Zacharias, J., "Calciphylaxis is usually non-ulcerating: risk factors, outcome and therapy," Kidney International 61(6): 2210-2217, Elsevier, Netherlands (Jun. 2002).

Fuster, J. M. B., et al., "Plant phosphates, phytate and pathological calcifications in chronic kidney disease," Nefrologia 37(1):20-28, Elsevier, Netherlands (Jan. 2017).

Giachelli, C. M., "Ectopic calcification: gathering hard facts about soft tissue mineralization," American Journal of Pathology 154(3): 671-675, American Society for Investigative Pathology, United States (Mar. 1999).

Grases, F., and Costa-Bauza, A., "Phytate (IP6) is a powerful agent for preventing calcifications in biological fluids: usefulness in renal lithiasis treatment," Anticancer Research 19(5A):3717-3722, International Institute of Anticancer Research, Greece (Jan. 1999).

Grases, F. and March, P., "A Study about Some Phosphate Derivatives as Inhibitors of Calcium Oxalate Crystal Growth," Journal of Crystal Growth 96(4):993-995, Elsevier Science Publishers B.V., The Netherlands (Aug. 1989).

(56)            References Cited

OTHER PUBLICATIONS

Grases, F., et al., "Absorption and excretion of orally administered inositol hexaphosphate (IP(6) or phytate) in humans," Biofactors 15(1):53-61, IOS Press, Netherlands (2001).

Grases, F., et al., "Effects of phytate and pyrophosphate on brushite and hydroxyapatite crystallization. Comparison with the action of other polyphosphates," Urological Research 28(2):136-140, Springer-Verlag, Germany (Apr. 2000).

Grases, F., et al., "Effects of phytic acid on renal stone formation in rats," Scandinavian Journal of Urology and Nephrology 32(4):261-265, Scandinavian University Press, Norway (Jan. 1998).

Grases, F., et al., "Phytate (Myo-inositol hexakisphosphate) inhibits cardiovascular calcifications in rats," Frontiers in Bioscience 11:136-142, Frontiers In Bioscience Publications, United States (Jan. 2006).

Grases, F., et al., "Phytate acts as an inhibitor in formation of renal calculi," Frontiers in Bioscience 12:2580-2587, Frontiers In Bioscience Publications, United States (Jan. 2007).

Green, C. J., et al., "D-myo-inositol-1, 2, 6-trisphosphate (PP56) Inhibits Lipid Peroxidation in Warm Ischaemic Rabbit Kidneys," Medical Science Research 17(18):749-750, Elsevier Applied Science, United States (1989).

Hafner, J., et al. "Uremic small-artery disease with medial calcification and intimal hyperplasia (so-called calciphylaxis): a complication of chronic renal failure and benefit from parathyroidectomy," Journal of the American Academy of Dermatology 33(6): 954-962, Elsevier, Netherlands (Dec. 1995).

Haynes, D. A., et al., "Occurrence of pharmaceutically acceptable anions and cations in the Cambridge Structural Database," Journal of Pharmaceutical Sciences 94(10): 2111-2120, Elsevier, Netherlands (Oct. 2005).

Henneman, P. H., et al., "The cause of hypercalcuria in sarcoid and its treatment with cortisone and sodium phytate," Journal of Clinical Investigation 35(11):1229-1242, American Society for Clinical Investigation, United States (Nov. 1956).

Hoppe, B., "An update on primary hyperoxaluria," Nat Rev Nephrol 8(8):467-475, Macmillan Publishers Limited, United Kingdom (Jun. 2012).

Irnell, L., "Metastatic calcification of soft tissue on overdosage of vitamin D," Acta Medica Scandinavica 185(3):147-152, Almqvist and Wiksell, Sweden (Jan. 1969).

Joubert, P., et al., "Hypothesis: Phytate is an important unrecognised nutrient and potential intravenous drug for preventing vascular calcification," Medical Hypothesis 94: 89-92, Elsevier, Netherlands (Sep. 2016).

Khakimov, Z.Z., et al., "Antioxidant Therapeutics of Acute Renal Insufficiency in Case Crush-Syndrome on Growing Rats," Uzbekskii Biologicheskii Zhurnal 5:3-6, Publishing House "Fan" of the Academy of Sciences of the Republic of Uzbekistan, Uzbekistan (2005).

Levin, A., et al., "Mathematical formulation to help identify the patient at risk of ischemic tissue necrosis—a potentially lethal complication of chronic renal failure," American Journal of Nephrology 13(6): 448-453, Karger, Switzerland (Oct. 1993).

Liu, W., et al., "Current understanding of coronary artery calcification," Journal of Geriatric Cardiology 12(6):668-675, Institute of Geriatric Cardiology, China (Nov. 2015).

Merriam-Webster Online Dictionary, "Prevention," accessed at http://www.merriam-webster.com/dictionary/prevention, accessed on Oct. 16, 2020, 1 page.

Salcedo, C., et al., "SNF472 Inhibits Heart Valve Calcification in a Novel In Vitro Method Using Porcine Whole Leaflets," Bone and Mineral Metabolism: Basic, Abstract PO0320, Kidney Week, American Society of Nephrology, United States (Oct. 22, 2020).

Mochel, M. C., et al. "Cutaneous calciphylaxis: a retrospective histopathologic evaluation," The American Journal of Dermatopathology 35(5): 582-586, Lippincott Williams and Wilkins Ltd., United States (Jul. 2013).

Nigwekar, S. U., et al., "Calciphylaxis: risk factors, diagnosis, and treatment," American Journal of Kidney Diseases 66(1): 133-146, Elsevier, Netherlands (Jul. 2015).

O'neill, W.C., et al., "Treatment with pyrophosphate inhibits uremic vascular calcification," Kidney International 79(5):512-517, Elsevier, United States (Mar. 2011).

Oudshoorn, M. H. M. et al., "Synthesis and characterization of hyperbranched polyglycerol hydrogels," Biomaterials 27(32): 5471-5479, Elsevier, Netherlands (Nov. 2006).

Pai, M. P., "Drug dosing based on weight and body surface area: mathematical assumptions and limitations in obese adults," Pharmacotherapy: The Journal of Human Pharmacology and Drug Therapy 32(9): 856-868, Wiley and Sons, United States (Sep. 2012).

Pan, S.-D., et al. "Weight-based dosing in medication use: what should we know?," Patient Prefer Adherence 10: 549-60, Dove Press, United Kingdom (Apr. 2016).

Perelló, J., et al. "First-time-in-human randomized clinical trial in healthy volunteers and haemodialysis patients with SNF472, a novel inhibitor of vascular calcification," Br J Clin Pharmacol 84(12): 2867-2876, Wiley and Sons, United States (Dec. 2018).

Phanish, M. K., et al., "Tumoral calcinosis associated with pyrexia and systemic inflammatory response in a haemodialysis patient: successful treatment using intravenous pamidronate," Nephrol Dial Transplant 15: 1691-1693, European Renal Association-European Dialysis and Transplant Association, United Kingdom (Oct. 2000).

Phase 2 Study With SNF472 in Calciphylaxis Patients. NCT02790073, ClinicalTrials.gov, accessed at https://clinicaltrials.gov/ct2/show/NCT02790073, accessed on Oct. 9, 2020, 7 pages.

Russo, D., et al., "Progression of coronary artery calcification and cardiac events in patients with chronic renal disease not receiving dialysis," Kidney International 80:112-118, Springer-Verlag, Germany (Jul. 2011).

Salcedo, C., et al. "A phase 1b randomized, placebo-controlled clinical trial with SNF472 in haemodialysis patients," Br J Clin Pharmacol 85(4): 796-806, British Pharmacological Society, United Kingdom (Apr. 2019).

Sanchis, P., et al., "Protective Effect of Myo-Inositol Hexaphosphate (Phytate) on Abdominal Aortic Calcification in Patients With Chronic Kidney Disease," Journal of Renal Nutrition 26(4):226-236, Elsevier, Netherlands (Jul. 2016).

"Sanifit Announces Results of the Phase II Clinical Trial of SNF472 in Patients with Calciphylaxis", accessed at https://www.sanifit.com/sanifit-announces-results-phase-ii-clinical-trial-snf472-patients-calciphylaxis/, accessed on Oct. 9, 2019; Published Mar. 6, 2018.

Shantouf, R. S., et al., "Total and individual coronary artery calcium scores as independent predictors of mortality in hemodialysis patients," American Journal of Nephrology 31(5):419-425, Karger AG, United States (Apr. 2010).

Sircus, M., Dr., "Calcification and Its Treatment with Magnesium and Sodium Thiosulfate," drsircus.com, accessed at drsircus.com/magnesium/calcification-and-its-treatment-with-magnesium-and-sodium-thiosulfate/, accessed on Dec. 8, 2009, 14 pages.

Sun, X. Y., et al., "Cardiovascular and renal effects of alpha-trinositol in ischemic heart failure rats," Life Science 57(12): 1197-1211, Elsevier, Netherlands (Aug. 1995).

Weenig, R. H., et al. "Calciphylaxis: natural history, risk factor analysis, and outcome," Journal of the American Academy of Dermatology 56(4): 569-579, Elsevier, Netherlands (Apr. 2007).

Wilms, D., et al., "Hyperbranched polyglycerols: from the controlled synthesis of biocompatible polyether polyols to multipurpose applications," Acc Chem Res 43(1): 129-141, American Chemical Society, United States (Jan. 2010).

Zabirnyk, A. i247, NDT Abstract Supplement 2018, Nephrology Dialysis Transplantation, , vol. 33, Issue suppl_1, May 2018, pp. i1-i660.

Sanifit to Present New Data on SNF472 for Vascular Calcification at the American Society of Nephrology Kidney Week 2020, accessed at URL:[https://www.sanifit.com/sanifit-to-present-new-data-on-snf472-for-vascular-calcification-at-the-american-society-of-nephrology-kidney-week-2020/], accessed on Oct. 14, 2020, published Oct. 12, 2020.

Sanifit to start new clinical development program of SNF472 in End Stage Kidney Disease patients with Peripheral Artery Disease, accessed at URL:[https://www.sanifit.com/sanifit-to-start-new-

(56)　　　　　　References Cited

OTHER PUBLICATIONS clinical-development-program-of-snf472-in-end-stage-kidney-disease-patients-with-peripheral-artery-disease/], accessed on Oct. 14, 2020, published Jul. 20, 2020.

SNF472 Mechanism of Action data published in British Journal of Pharmacology, URL:[https://www.sanifit.com/snf472-mechanism-of-action-data-published-in-british-journal-of-pharmacology/], accessed on Oct. 14, 2020, published Jun. 25, 2020.

Perelló, J., et al. "Mechanism of action of SNF472, a novel calcification inhibitor to treat vascular calcification and calciphylaxis," Br J Pharmacol 117(19):4400-4415, Wiley-Blackwell on behalf of the British Pharmacological Society, United Kingdom (Oct. 2020).

Chertow, G., et al., "SNF472 Consistently Slows Progression of Coronary Artery Calcification Across Subgroups of Patients on Hemodialysis," Novel Approaches to Mineral and Bone Metabolism, Abstract TH-OR18, Kidney Week, American Society of Nephrology, United States (Oct. 22, 2020).

Sinha, S., et al., "Design of the CALCIPHYX Study, a Randomized, Double-Blind, Placebo-Controlled Phase 3 Study of SNF472 for Treating Calciphylaxis," Informational Posters, Abstract INFO07, Kidney Week, American Society of Nephrology, United States (Oct. 22, 2020).

Perello, J., et al., "Pharmacokinetics, Pharmacodynamics (PK-PD), and Exposure-Efficacy Evaluation from CaLIPSO, a Phase 2B Study to Assess the Effect of SNF472 on Progression of Cardiovascular Calcification in Patients on Hemodialysis," Hemodialysis and Frequent Dialysis—3, Abstract PO1142, Kidney Week, American Society of Nephrology, United States (Oct. 22, 2020).

Sussman, C., and Bates-Jensen, B., "Tools to measure wound healing," In: Wound Care: A Collaborative Practice Manual For Health Professionals, pp. 131-161, Philadelphia, PA, Lippincott Williams & Wilkins, United States (2012).

Ferrer, M. D., et al., "Characterization of SNF472 pharmacokinetics and efficacy in uremic and non-uremic rats models of cardiovascular calcification," PLoS one 13(5):e0197061, Public Library of Science, United States (May 2018).

Ferrer, M.D., et al., "A Novel Pharmacodynamic Assay to Evaluate the Effects of Crystallization Inhibitors on Calcium Phosphate Crystallization in Human Plasma," Scientific Reports 7(1):6858, pp. 1-12, Nature Publishing Group, United Kingdom (Jul. 2017).

NCT02790073, "Phase 2 Study with SNF472 in Calciphylaxis Patients", ClinicalTrials.gov, submitted date: Sep. 11, 2017, accessed at https://clinicaltrials.gov/ct2/history/NCT02790073?V_6=View#StudyPageTop, 7 pages.

NCT02966028, "Effect of SNF472 on Progression of Cardiovascular Calicification in End-Stage-Renal-Disease (ESRD) Patients on Hemodialysis (HD)" ClinicalTrials.gov, submitted date: Aug. 29, 2017, accessed at https://classic.clinicaltrials.gov/ct2/history/NCT02966028?V_32=View#StudyPageTop, 20 pages.

Rocha-Singh, K., et al., "Peripheral Arterial Calcification: Prevalence, Mechanism, Detection, and Clinical Implications," Catheterization and Cardiovascular Interventions 83(6):E212-E220, Wiley-Liss, United States (May 2014).

Zettervall, S.L., et al., "Association of Arterial Calcification With Chronic Limb Ischemia in Patients With Peripheral Artery Disease," Journal of Vascular Surgery 67(2):507-513, Elsevier, Netherlands (Feb. 2018).

Alabaz, D., et al., "Unusual Idiopathic Calcinosis Cutis Universalis in a Child," Case Rep Dermatol 1(1):16-22, Karger, Switzerland (Aug. 2009).

Azpiazu, D., et al., "Role of pyrophosphate in vascular calcification in chronic kidney disease," Nefrologia (Engl Ed) 38(3):250-257, Elsevier, Spain (May 2018).

Bates-Jensen, B.M., et al., "Validity and Reliability of the Pressure Sore Status Tool," Decubitus 5(6):20-28, S-N Publications, United States (Nov. 1992).

Efstratiadis, G., et al., "Coronary calcification in patients with end-stage renal disease: a novel endocrine disorder?" Hormones (Athens) 6(2):120-131, Greek Society of Endocrinology, Greece (Apr. 2007).

Higgins, C.L., et al., "Quantification of calcification in atherosclerotic lesions," Arterioscler Thromb Vasc Biol 25(8):1567-1576, Lippincott Williams & Wilkins, United States (Aug. 2005).

Holt, S.G., and Smith, E.R., "Fetuin-A-containing calciprotein particles in mineral trafficking and vascular disease," Nephrol Dial Transplant 31(10):1583-1587, Oxford University Press, United Kingdom (Oct. 2016).

International Search Report and Written Opinion for Application No. PCT/IB2018/057904, European Patent Office, Netherlands, mailed on Apr. 17, 2019, 12 pages.

Jensen, P.S., "Chondrocalcinosis and other calcifications," Radiol Clin North Am 26(6):1315-1325, Saunders, United States (Nov. 1988).

Lanzer, P., et al., "Medial vascular calcification revisited: review and perspectives," Eur Heart J 35(23):1515-1525, Oxford University Press, United Kingdom (Jun. 2014).

Liu, Q.L., et al., "Effectiveness of a traditional Chinese medicine, Wulingsan, in suppressing the development of nephrocalcinosis induced by a high phosphorus diet in young rats," Med Electron Microsc 34(2):103-114, Springer Nature, Germany (Jun. 2001).

Mccarty, M.F., and Dinicolantonio, J.J., "The molecular biology and pathophysiology of vascular calcification," Postgrad Med 126(2):54-64, Taylor & Francis, United Kingdom (Mar. 2014).

Nicoll, R., and Henein, M.Y., "The predictive value of arterial and valvular calcification for mortality and cardiovascular events," Int J Cardiol Heart Vessel 3:1-5, Elsevier, Netherlands (Feb. 2014).

Orzechowska, S., et al., "Physicochemical and micro-tomographic characterization of inorganic deposits associated with aortic stenosis," J Heart Valve Dis 23(1):40-47, ICR Publishers, United States (Jan. 2014).

Otero, J.E., et al., "Severe skeletal toxicity from protracted etidronate therapy for generalized arterial calcification of infancy," J Bone Miner Res 28(2):419-430, American Society for Bone and Mineral Research, United States (Feb. 2013).

Perelló, J., et al., "SNF472, a novel inhibitor of vascular calcification, could be administered during hemodialysis to attain potentially therapeutic phytate levels," J Nephrol 31(2):287-296, Springer Nature, Germany (Apr. 2018).

Rez, P., "What does the crystallography of stones tell us about their formation?" Urolithiasis 45(1):11-18, Springer Nature, Germany (Feb. 2017).

Vervaet, B.A., et al., "An active renal crystal clearance mechanism in rat and man," Kidney Int 75(1):41-51, Elsevier, Netherlands (Jan. 2009).

Ziegler, S.G., et al., "Ectopic calcification in pseudoxanthoma elasticum responds to inhibition of tissue-nonspecific alkaline phosphatase," Sci Transl Med 9(393):eaal1669, American Association for the Advancement of Science, United States (Jun. 2017).

U.S. Appl. No. 18/778,767, Perello Bestard, J., et al., filed Jul. 19, 2024 (Not Published). (Now Abandoned).

Adragao, T., et al., "A plain X-ray vascular calcification score is associated with arterial stiffness and mortality in dialysis patients," Nephrol Dial Transplant 24(3):997-1002, Oxford University Press, United Kingdom (Mar. 2009).

Agatston, A.S., et al., "Quantification of coronary artery calcium using ultrafast computed tomography," J Am Coll Cardiol 15(4):827-832, Elsevier, Netherlands (Mar. 1990).

Aleti, S., "Types, Causes and Risk Factors of Peripheral Artery Disease," Heart and Vascular Care Screenings And Diagnostics, Orlando Health (Jul. 2018), 3 Pages.

Amann, K., "Media Calicification and Intima Calcification are Distinct Entities in Chronic Kidney Disease," Clinical Journal of the American Society of Nephrology 3(6):1599-605, The American Society of Nephrology, United States (Nov. 2008).

Ariyoshi, T., et al., "Effect of Etidronic Acid on Arterial Calcification in Dialysis Patients," Clinical Drug Investigation 26(4):215-222, Springer International, New Zealand (Apr. 2006).

Bellasi, A., et al. "Correlation of simple imaging tests and coronary artery calcium measured by computed tomography in hemodialysis patients," Kidney Int 70(9):1623-1628, Elsevier, Netherlands (Nov. 2006).

(56)

References Cited

OTHER PUBLICATIONS

Berg, C.J.V.D., et al., "Inositol Phosphates and Phytic Acid as Inhibitors of Biological Calcification in the Rat," Clinical Science 43(3):377-383, Blackwell Scientific Publications, United Kingdom (Sep. 1972).

Blacher, J., et al., "Arterial Calcifications, Arterial Stiffness, and Cardiovascular Risk in End-stage Renal Disease," Hypertension 38(4):938-942, Lippincott Williams & Wilkins, United States (Oct. 2001).

Blaha, M.J., "Associations between C-reactive protein, coronary artery calcium, and cardiovascular events: implications for the JUPITER population from MESA, a population-based cohort study," Lancet 378(9792):684-692, Elsevier, Netherlands (Aug. 2011).

Blaha, M.J., et al., "Improving the CAC Score by Addition of Regional Measures of Calcium Distribution," JACC Cardiovasc Imaging 9(12): 1407-1416, Elsevier, United States (Dec. 2016).

Bloom, J.R., and Navon, J.R., "Inhibitory Effect of Phytate on Bone Resorption in Organ Cultures," Journal of Dental Research 63(6):890-893, Sage, United States (1979).

Boucher, L., et al., "Internalization and Distribution of Inositol Hexakisphosphate in Red Blood Cells," Biotechnology and Applied Biochemistry 24(Pt 1):73-78, Academic Press, United States (Aug. 1996).

Bourgeaux. V., et al., "Efficacy of homologous inositol hexaphosphate-loaded red blood cells in sickle transgenic mice," British Journal of Haematology 157(3):357-369, Blackwell Publishing Ltd., United Kingdom (May 2012).

Brandenburg, V.M., et al., "Improvement in wound healing, pain, and quality of life after 12 weeks of SNF472 treatment: a phase 2 open-label study of patients with calciphylaxis," J Nephrol 32(5):811-821, Springer Nature, Germany (Oct. 2019).

Brown, A.J., "Role of biomechanical forces in the natural history of coronary atherosclerosis," Nat Rev Cardiol 13(4):210-220, Nature Portfolio, United Kingdom (Apr. 2016).

Budoff, M.J., et al., "Progression of coronary artery calcium predicts all-cause mortality," JACC Cardiovasc Imaging 3(12):1229-1236, Elsevier, Netherlands (Dec. 2010).

Callister, T.Q., et al., "Coronary Artery Disease: Improved Reproducibility of Calcium Scoring with an Electron-beam CT Volumetric Method," Radiology 208(3):807-814, Radiological Society of North America, United States (Sep. 1998).

Chen, J., et al., "Coronary Artery Calcification and Risk of Cardiovascular Disease and Death Among Patients With Chronic Kidney Disease," JAMA Cardiology 2(6):635-643, American Medical Association, United States (Jun. 2017).

Chertow, G.M., et al., "Sevelamer attenuates the progression of coronary and aortic calcification in hemodialysis patients," Kidney Int 62(1):245-252, Elsevier, Netherlands (Jul. 2002).

ClinicalTrials., "Effect of SNF472 on Progression of Cardiovascular Calcification in End-Stage-Renal-Disease (ESRD) Patients on Hemodialysis (HD)," NCT02966028, accessed at https://clinicaltrials.gov/study/NCT02966028?cond=NCT02966028&rank=1&tab=results, accessed on Nov. 2016, 5 Pages.

Conte, A., et al., "Urinary Lithogen Risk Test: Usefulness in the Evaluation of Renal Lithiasis Treatment Using Crystallization Inhibitors (Citrate and Phytate)," Archivos Espannoles De Urologiia 52(3):305-310, Iniestares, Spain (Apr. 1999).

Co-pending Application, U.S. Appl. No. 19/053,226, inventors Perello Bestard, J., et al., filed Feb. 13, 2025 (Not yet Published).

Co-pending Application, U.S. Appl. No. 19/065,816, inventors Bassissi, M.F., et al., filed Feb. 27, 2025 (Not yet Published).

Co-pending Application, U.S. Appl. No. 19/355,714, inventors Bassissi, M.F., et al., filed Oct. 10, 2025 (Not yet Published).

Cozzolino, M., et al., "Cardiovascular disease in dialysis patients," Nephrol Dial Transplant 33(Suppl 3):iii28-iii34, Oxford University Press, United Kingdom (Oct. 2018).

Davita, "Kidney Stones and Chronic Kidney Disease," accessed at http://www.davita.com/kidney-disease/overview/symptoms-and-diagnosis/kidney-stones-a . . . , accessed on on Nov. 5, 2015, 1 page.

Di Iorio, B., et al., "Coronary Artery Calcification Progression is Associated with Arterial Stiffness and Cardiac Repolarization Deterioration in Hemodialysis Patients," Kidney & Blood Pressure Research 34(3):180-187, Karger Publishers, Switzerland (Apr. 2011).

Disthabanchong, S., et al., "Abdominal Aorta and Pelvic Artery Calcifications on Plain Radiographs may Predict Mortality in Chronic Kidney Disease, Hemodialysis and Renal Transplantation," International Urology and Nephrology, 50(2):355-364, Springer, Germany (Feb. 2018).

Ditmar, R., and Steidl, L., "The Importance of Magnesium in Orthopedics. Vi. The Importance of Magnesium in the Treatment of Ectopic Calcification and Ossification," Acta Chirurgiae Orthopaedicae Et Traumatologiae Cechoslovaca 56(3):190-200, Scientia Medica, Czech Republic (Jun. 1989).

Einck, L., and Holaday. J.W., "Enhancement of Tissue Oxygenation By Intracellular Introduction of Inositol Hexaphosphate By Flow Electroporation of Red Blood Cells," Update in Intensive Care And Emergency Medicine, Tissue Oxygenation in Acute Medicine 33:357-374, W. J. Sabbald, et al. (Eds), Springer-Verlag Berlin Heidleberg, Germany (1998).

Final Office Action mailed Nov. 9, 2015, in U.S. Appl. No. 14/212,286, Perello Bestard, J., et al., filed Mar. 14, 2014, 18 pages.

Final Office Action mailed Sep. 1, 2020, in U.S. Appl. No. 16/209,150, Perello Bestard, J., et al., filed Dec. 4, 2018, 16 pages.

Final Office Action mailed Sep. 7, 2021, in U.S. Appl. No. 16/209,150, Perello Bestard, J., et al., filed Dec. 4, 2018, 11 pages.

Final Office Action mailed Jan. 23, 2023, in U.S. Appl. No. 17/728,807, Perello Bestard, J., et al., filed Apr. 25, 2022, 11 pages.

Foley, R.N., et al., "Clinical Epidemiology of Cardiovascular Disease in Chronic Renal Disease," American Journal of Kidney Diseases 32(5 Suppl 3):S112-119, Elsevier, Netherlands (Nov. 1998).

Gomes, B.C., et al., "Inhibitory Effect of Inositol Phosphates on Parathyroid Hormone-induced Bone Resorption in Organ Cultures," Journal of Dental Research 63(6):890-893, Sage, United States (Jun. 1984).

Grases, F., and Costa-Bauza, A., "Potentiometric Study of the Nucleation of Calcium Oxalate in Presence of Several Additives," Clinical Chemistry and Enzymology Communications 3:319-328, The Harwood Academic Publishers, United States (1991).

Grases, F., et al., "A New Procedure to Evaluate the Inhibitory Capacity of Calcium Oxalate Crystallization in Whole Urine," International Urology and Nephrology 27(6):653-661, Springer, Netherlands (1995).

Grases, F., et al., "Absorption of Myo-inositol Hexakisphosphate (InsP6) Through the Skin in Humans," Die Pharmazie 61(7):652, Govi-Verlag Pharmazautischer Verlag, Germany (Jul. 2006).

Grases, F., et al., "Anticalculus Effect of a Triclosan Mouthwash Containing Phytate: A Double-blind, Randomized, Three-period Crossover Trial," Journal of Periodontal Research 44(5):616-621, Wiley-Blackwell, United States (Oct. 2009).

Grases, F., et al., "Artificial Simulation of the Early Stages of Renal Stone Formation," British Journal of Urology 74(3):298-301, Blackwell Science, United Kingdom (Sep. 1994).

Grases, F., et al., "Dietary Myo-inositol Hexaphosphate Prevents Dystrophic Calcifications in Soft Tissues: A Pilot Study in Wistar Rats," Life Sciences 75(1):11-19, Elsevier, Netherlands (May 2004).

Grases, F., et al., "Effect of Crystallization Inhibitors on Vascular Calcifications Induced by Vitamin D: A Pilot Study in Sprague-Dawley Rats," Circulation Journal 71(7):1152-1156, Japanese Circulation Society, Japan (Jul. 2007).

Grases, F., et al., "Phytate Inhibits Bovine Pericardium Calcification in Vitro," Cardiovascular Pathology 17(3):139-145, Elsevier Science Pub. Co., United States (May-Jun. 2008).

Grases, F., et al., "Phytate Prevents Tissue Calcifications in Female Rats," BioFactors 11(3):171-177, Wiley, United States (2000).

Grases, F., et al., "Studies on Calcium Oxalate Monohydrate Crystallization: Influence of Inhibitors," Urological Research 22(1):39-43, Springer-Verlag, Germany (Apr. 1994).

Grases, F., et al., "Study of a Myo-inositol Hexaphosphate-based Cream to Prevent Dystrophic Calcinosis Cutis," The British Journal of Dermatology 152(5):1022-1025, Oxford University Press, United Kingdom (May 2005).

(56) References Cited

OTHER PUBLICATIONS

Grases, F., et al., "Study of the Absorption of Myo-inositol Hexakisphosphate (InsP6) Through the Skin," Biological & Pharmaceutical Bulletin 28(4):764-767, Pharmaceutical Society of Japan, Japan (Apr. 2005).

Grases, F., et al., "Study of the Effects of Different Substances on the Early Stages of Papillary Stone Formation," Nephron 73(4):561-568, Karger, Switzerland (Jan. 1996).

Grau., et al., "Relationship Between Phytate and Valvular Heart Calcifications. Field Study To Design a Clinical Assay About Aortic Stenosis," Sanifit Laboratory.

Halvorson, K.G., et al., "Intravenous Ibandronate Rapidly Reduces Pain, Neurochemical Indices of Central Sensitization, Tumor Burden, and Skeletal Destruction in a Mouse Model of Bone Cancer," Journal of Pain and Symptom Management 36(3):289-303, Elsevier, United States (Sep. 2008).

Hamburg, N.M., and Balady G.J., "Exercise Rehabilitation in Peripheral Artery Disease: Functional Impact and Mechanisms of Benefits," Circulation 123(1):87-97, Lippincott Williams & Wilkins, United States (Jan. 2011).

Hippocrates, Y., and Agroyannis, B., et al., "Sodium Thiosulfate Treatment of Soft-tissue Calcifications in Patients With End-stage Renal Disease," Peritoneal Dialysis International 7(4):250-252, SAGE Publications, United Kingdom (Oct. 1987).

Howard, G., et al., "Does the Association of Risk Factors and Atherosclerosis Change With Age? An Analysis of the Combined ARIC and CHS Cohorts. The Atherosclerosis Risk in Communities (ARIC) and Cardiovascular Health Study (CHS) Investigators," Stroke 28(9):1693-1701, Lippincott Williams & Wilkins, United States (Sep. 1997).

Inhibit, "Definition of Inhibit by the Free Dictionary," accessed at http://www.thefreedictionary.com/inhibit, accessed on Feb. 28, 2018, 8 pages.

International Search Report and Written Opinion for International Application No. PCT/EP2020/081674, European Patent Office, Netherlands, mailed on Oct. 2, 2021, 9 pages.

International Search Report and Written Opinion for International Application No. PCT/ES2020/070070, European Patent Office, Netherlands, mailed on May 12, 2020, 16 pages.

Jamal, S.A., et al., "Effect of Calcium-based Versus non-calcium-based Phosphate Binders on Mortality in Patients with Chronic Kidney Disease: An Updated Systematic Review and Meta-analysis," Lancet 382(9900):1268-1277, Elsevier, Netherlands (Oct. 2013).

James, C.A., et al., "Pediatric Case of the Day. Klippel-Trenaunay Syndrome," Radiographics 19(4):1093-1096, Radiological Society of North America, United States (Jul.-Aug. 1999).

Jean, G., et al., "Peripheral Vascular Calcification in Long-haemodialysis Patients: Associated Factors and Survival Consequences," Nephrology, Dialysis, Transplantation 24(3):948-955, Oxford University Press, United Kingdom (Mar. 2009).

Johnson, R.C., "Vascular calcification: pathobiological mechanisms and clinical implications," Cut Res 99(10):1044-59, Lippincott Williams & Wilkins, United States (Nov. 2006).

Kobayashi, S., "Cardiovascular Events in Hemodialysis Patients: Challenging Against Vascular Calcification," Journal of the Japanese Society of Vascular Surgery, 25:359-365, Japanese Society for Vascular Surgery, Japan (Dec. 2016).

Kalantar-Zadeh, K., et al., "Understanding Sources of Dietary Phosphorus in the Treatment of Patients With Chronic Kidney Disease," Clinical Journal of the American Society of Nephrology 5(3):519-530, Wolters Kluwer Health, United States (Mar. 2010).

Karohl, C., et al., "Hybrid myocardial imaging for risk stratification prior to kidney transplantation: added value of coronary calcium and epicardial adipose tissue," J Nucl Cardiol 20(6): 1013-1020, Springer Science+Business Media, Germany (Dec. 2013).

Kasting, G.B., et al. "Skin Penetration Enhancement Methods for Hydrophilic Compounds," Pharmaceutical Research 14(Suppl_11):S452 (Nov. 1997), ISSN: 0724-8741.

Kaufman, H.W., "Interactions of Inositol Phosphates with Mineralized Tissues," in *Phytic Acid: Chemistry and Applications*, pp. 302-320, Pilatus Press, Minneapolis, United States (1986).

Kim, T.I., and Guzman, R.J., "The Role of Calcification in Peripheral Artery Disease," Chapter 8 in Cardiovascular Calcification and Bone Mineralization, Aikawa, E., and Hutcheson, J.D., eds., pp. 167-183, Springer Nature, Switzerland (Jul. 2020).

Kishimoto, Y., et al., "Plasma Heme Oxygenase-1 Levels in Patients with Coronary and Peripheral Artery Diseases," Disease Markers 2018:6138124, Wiley, United States (Aug. 2018), 8 pages.

Kitamura, K., et al., "Relationship Between Cardiac Calcification and Left Ventricular Hypertrophy in Patients with Chronic Kidney Disease at Hemodialysis Initiation," Heart Vessels 32(9):1109-1116, Springer Nature, Germany (Sep. 2017).

Kovacs, A., et al., "Ultrastructure and Composition of Thrombi in Coronary and Peripheral Artery Disease: Correlations with Clinical and Laboratory Findings," Thrombosis Research 135:760-766, Elsevier, Netherlands (Apr. 2015).

Kwon, H.Y., et al., "The association between mortality and abdominal aortic calcification and relation between its progression and serum calcium concentration in chronic hemodialysis patients," Kidney Res Clin Pract 33(2):95-102, Elsevier, Netherlands (Jun. 2014).

Lo, G.S., et al., "Effect of Phytate:zinc Molar Ratio and Isolated Soybean Protein on Zinc Bioavailability," The Journal of Nutrition 111(12):2223-2235, Elsevier, United States (Dec. 1981).

Marwick, T.H., et al., "Chronic Kidney Disease and Valvular Heart Disease: Conclusions From a Kidney Disease: Improving Global Outcomes (KDIGO) Controversies Conference," Kidney International 96(4):836-849, Elsevier, Netherlands (Oct. 2019).

Mcdermott, M.M., "Functional Impairment in Peripheral Artery Disease and How to Improve It in 2013," Current Cardiology Reports 15(4):347, Current Science, United States (Apr. 2013), 13 pages.

Merriam-Webster, Inc, "Merriam-Webster's Collegiate Dictionary," Tenth Edition, p. 924, Springfield, United States (1998), 3 pages.

Merriam-Webster, "Prevention," accessed at http://www.merriam-webster.com/dictionary/prevention, accessed on Feb. 7, 2015, 1 page.

Miyazaki, Y., et al., "Low Plasma. Levels of Fibroblast Growth Factor-21 in Patients with Peripheral Artery Disease," Journal of Atherosclerosis and Thrombosis 25:821-828, Japan Atherosclerosis Society, Japan (Sep. 2018).

Nambi, V., et al., "Differences in Responses of Platelets to Fluid Shear Stress in Patients with Peripheral Artery Disease (PAD) and Coronary Artery Disease (CAD)," Platelets 20(3):199-205, Elsevier, Netherlands (May 2009).

Nancollas, G.H., et al., "Novel Insights Into Actions of Bisphosphonates on Bone: Differences in Interactions With Hydroxyapatite," Bone 38(5):617-627, Elsevier Science, United States (May 2006).

NCT02966028, "Effect of SNF472 on Progression of Cardiovascular Calcification in End-Stage-Renal-Disease (ESRD) Patients on Hemodialysis (HD)," (2016), accessed at https://clinicaltrials.gov/ct2/show/NCT02966028, accessed on May 17, 2023, 11 pages.

NCT02966028, "Effect of SNF472 on Progression of Cardiovascular Calcification in End-Stage-Renal-Disease (ESRD) Patients on Hemodialysis (HD)," Study Record Version 54 (2019), accessed at https://clinicaltrials.gov/study/NCT02966028?tab=history&a=54&b=54#StudyPageTop, dated Sep. 23, 2019, 16 pages.

Non-Final Office Action mailed May 6, 2015, in U.S. Appl. No. 14/212,286, Perello Bestard, J., et al., filed Mar. 14, 2014, 20 pages.

Non-Final Office Action mailed Jul. 3, 2017, in U.S. Appl. No. 15/163,366, Perello Bestard, J., et al., filed May 24, 2016, 21 pages.

Non-Final Office Action mailed Feb. 17, 2022, in U.S. Appl. No. 16/209,150, Perello Bestard, J., et al., filed Dec. 4, 2018, 13 pages.

Non-Final Office Action mailed Mar. 20, 2020, in U.S. Appl. No. 16/209,150, Perello Bestard, J., et al., filed Dec. 4, 2018, 20 pages.

Non-Final Office Action mailed Mar. 30, 2021, in U.S. Appl. No. 16/209,150, Perello Bestard, J., et al., filed Dec. 4, 2018, 12 pages.

Non-Final Office Action mailed Oct. 12, 2022, in U.S. Appl. No. 17/728,807, Perello Bestard, J., et al., filed Apr. 25, 2022, 12 pages.

Non-Final Office Action mailed Aug. 15, 2024, in U.S. Appl. No. 18/357,004, Perello Bestard, J., et al., filed Jul. 21, 2023, 12 pages.

(56) References Cited

OTHER PUBLICATIONS

Notice of Allowance mailed Feb. 17, 2016, in U.S. Appl. No. 14/212,286, Perello Bestard, J., et al., filed Mar. 14, 2014, 11 pages.

Notice of Allowance mailed Mar. 2, 2018, in U.S. Appl. No. 15/163,366, Perello Bestard, J., et al., filed May 24, 2016, 9 pages.

Okuno, S., et al., "Presence of Abdominal Aortic Calcification is Significantly Associated with All-cause and Cardiovascular Mortality in Maintenance Hemodialysis Patients," American Journal of Kidney Diseases 49(3):417-425, W.B. Saunders, United States (Mar. 2007).

O'neill, W.C., et al., "Prevalence of Nonatheromatous Lesions in Peripheral Arterial Disease," Arteriosclerosis, Thrombosis, and Vascular Biology 35(2):439-447, American Heart Association, United States (Dec. 2014).

Pasch, A., et al., "Nanoparticle-based Test Measures Overall Propensity for Calcification in Serum," Journal of the American Society of Nephrology 23(10):1744-1752, Wolters Kluwer Health, United States (Oct. 2012).

Patel, L., et al., "Sevelamer Versus Calcium-Based Binders for Treatment of Hyperphosphatemia in CKD: A Meta-Analysis of Randomized Controlled Trials," Clin J Am Soc Nephrol 11(2):232-244, American Society of Nephrology, United States (Feb. 2016).

Raggi, P., et al., "Association of pulse wave velocity with vascular and valvular calcification in hemodialysis patients," Kidney Int 71(8):802-807, Elsevier, Netherlands (Apr. 2007).

Raggi, P., et al., "Cardiac calcification in adult hemodialysis patients. A link between end-stage renal disease and cardiovascular disease," Journal of the American College of Cardiology 39(4):695-701, American College of Cardiology Foundation, United States (Feb. 2002).

Raggi, P., et al., "Interaction of vascular and bone disease in patients with normal renal function and patients undergoing dialysis," Nature Clinical Practice. Cardiovascular Medicine 4(1):26-33, Nature Portfolio, United Kingdom (Jan. 2007).

Raggi, P., et al., "The ADVANCE study: a randomized study to evaluate the effects of cinacalcet plus low-dose vitamin D on vascular calcification in patients on hemodialysis," Nephrol Dial Transplant 26(4):1327-1339, Oxford University Press, United Kingdom (Apr. 2011).

Rao, P.S., et al., "Protection of Ischemic Heart From Reperfusion Injury by Myo-inositol Hexaphosphate, A Natural Antioxidant," The Annals of Thoracic Surgery 52(4):908-912, Elsevier, Netherlands (Oct. 1991).

Rein, P., et al., "Systemic Inflammation is Higher in Peripheral Artery Disease Than in Stable Coronary Artery Disease," Atherosclerosis 239(2):299-303, Elsevier, Ireland (Apr. 2015).

Reiter, N., et al., "Calcinosis Cutis Part I. Diagnostic Pathway," Journal of the American Academy of Dermatology 65:1-12, St. Louis, MO, United States (Jul. 2011).

Sadek, T., "Sevelamer hydrochloride with or without alphacalcidol or higher dialysate calcium vs calcium carbonate in dialysis patients: an open-label, randomized study," Nephrol Dial Transplant 18(3):582-588, Oxford University Press, United Kingdom (Mar. 2003).

Saeki, T., et al., "Inositol-1,4,5-trisphosphate Increases Contractions but Not L-type Calcium Current in Guinea Pig Ventricular Myocytes," Cardiovascular Research 41(3):620-628, Oxford Journals, United Kingdom (Mar. 1999).

Sanifit, "Sanifit announces that the Phase 2b CaLIPSO trial of SNF472 met its primary endpoint in slowing the progression of cardiovascular calcification in patients on hemodialysis," BioSpace.com, accessed at https://www.biospace.com/sanifit-announces-that-the-phase-2b-calipso-trial-of-snf472-met-its-primary-endpoint-in-slowing-the-progression-of-cardiovascular-calcification-in-patients-on-hemodialysis, dated Oct. 31, 2019, 3 pages.

Shao, U.S., et al., "Molecular Mechanisms of Vascular Calcification: Lessons Learned from the Aorta," Arteriosclerosis, Thrombosis, and Vascular Biology 26(7):1423-1430, American Heart Association, United States (Jul. 2006).

Steidl, L., and Ditmar, R., "Soft Tissue Calcification Treated With Local and Oral Magnesium Therapy," Magnesium Research 3(2):113-119, John Libbey And Company, United Kingdom (Jun. 1990).

Straub, M., and Hautmann, R.E., "Developments in Stone Prevention," Current Opinion in Urology 15(2):119-126, Lippincott Williams & Wilkins, United States (Mar. 2005).

Sullivan, B.J., and Flynn. P.M., "Influence of Inositol on Peripheral Vascular Responses to Cold Injury," Proceedings of the Society for Experimental Biology and Medicine 94(2):346-347, SAGE Publishing, United States (Feb. 1957).

Tripathi, A.K., et al., "Soybean—A Consummate Functional Food: A Review," Journal of Food Sciences and Technology 42(2):111-119, Springer Nature, Germany (2005).

Van Der Kaay, J., and Van Haastert, P.J., "Desalting Inositolpolyphosphates by Dialysis," Analytical Biochemistry 225(1):183-185, Elsevier, United States (Feb. 1995).

Verbeke, F., et al., "Prognostic Value of Aortic Stiffness and Calcification for Cardiovascular Events and Mortality in Dialysis Patients: Outcome of the Calcification Outcome in Renal Disease (CORD) Study," Clinical Journal of the American Society of Nephrology 6(1):153-159, Wolters Kluwer Health, United States (Jan. 2011).

Westerling, D., et al., "Postoperative Recovery After Cholecystectomy by Minilaparotomy: A Randomized Double-blind Comparison Between Alpha-trinositol and Placebo," Pharmacology & Toxicology 81(6):253-258, Elsevier, Netherlands (Dec. 1997).

Zabirnyk, A., et al., "SNF472, A Novel Anti-crystallization Agent, Inhibits Induced Calcification in an in Vitro Model of Human Aortic Valve Calcification," Vascular Pharmacology 122-123:106583, Elsevier Science, United States (Nov.-Dec. 2019).

IP AND IP ANALOGS DOSAGE REGIMENS FOR THE TREATMENT OF ECTOPIC CALCIFICATIONS

BACKGROUND

Field

The present disclosure is related to compositions and methods to treat and/or prevent ectopic calcifications comprising the administration of inositol phosphates, their analogs and derivatives.

Background

Cutaneous and subcutaneous calcifications (in general referred to as ectopic calcifications) arise as complications in numerous diseases. Ectopic calcifications can be classified into dystrophic, metastatic, idiopathic, or iatrogenic calcifications, or into calciphylaxis. Calciphylaxis corresponds to the calcification of small sized blood vessels and of the sub-cutaneous adipose tissue. Most of the time calciphylaxis is secondary to chronic renal failure, and it is often associated with abnormalities of calcium and phosphate metabolism. However, it remains a separate entity given its specific pathophysiology and its particular evolutionary modalities.

Beyond the abnormal nature of their presence, these calcifications can cause complications in terms of functional capability (e.g., limitation of range of motion and joint function), pain (e.g., very painful nature of some calcifications, particularly in calciphylaxis) or on the trophic level (e.g., ischemia and necrosis of the cutaneous and subcutaneous tissues) that can lead to additional infectious complications.

Although a number of treatments have been tried and reported (e.g., bisphosphonates, calcium channel blockers, probenecid) for these cutaneous and subcutaneous calcifications, to date there is no existing curative treatment for which efficacy has been demonstrated with a sufficient level of proof.

Calciphylaxis, also known as calcific uremic arteriolopathy (CUA), is a severe form of vascular calcification that affects approximately 1% to 4% of patients with end-stage renal disease, almost exclusively those who are on hemodialysis. See, e.g., Angelis et al. (1997) Surgery 122:1083-1089; Budisavljevic et al. (1996) J. Am. Soc. Nephrol. 7:978-982; Levin et al. (1993) Am. J. Nephrol. 13:448-453. One-year mortality for calciphylaxis has been reported to be between 45% and 80%, with ulcerated lesions being associated with higher mortality than non-ulcerated lesions (Nigwekar et al. (2015) Am. J. Kidney Dis. 66:133-146; Hafner et al. (1995) J. Am. Acad. Dermatol. 33:954-962; Fine & Zacharias (2002) Kidney International 61:2210-2217; Weenig et al. (2007) J. Am. Acad. Dermatol. 56:569-579).

In calciphylaxis, progressive, painful, necrotic skin ulcers result from calcification of small peripheral vessels. Mochel at al. (2013) Am. J. Dermatopathol. 35:582-586. Current treatment paradigm is palliative and based on anecdotal clinical data. Options include, e.g., intravenous sodium thiosulfate, bisphosphonates, and switching from calcium-based to non-calcium-based phosphate binders, but there are no approved therapies for calciphylaxis. The focus of treatment in calciphylaxis is often symptomatic, comprising wound care and pain management, rather than treating the underlying cause. Nigwekar et al. (2015) Am. J. Kidney Dis. 66:133-146.

Accordingly, there is a need for new therapeutic approaches to treat calciphylaxis, and ectopic calcifications in general.

BRIEF SUMMARY

The present disclosure provides methods to treat and/or prevent ectopic calcification (e.g., calciphylaxis calcifications) and/or the consequences thereof in a subject in need thereof comprising administering at least one dose of an inositol phosphate of the disclosure (e.g., inositol hexaphosphate or an analog or derivative thereof), or a combination thereof, in a dosage of about 6 mg to 9 mg per kg per day to the subject, wherein the administration of the dosage effectively treats or prevents ectopic calcification and/or the consequences thereof in the subject.

In some aspects, the inositol phosphate of the disclosure (e.g., inositol hexaphosphate or an analog or derivative thereof) comprises a compound of formula I, a pharmaceutically acceptable salt thereof, or a combination thereof:

wherein
(i) $R_1$, $R_3$, $R_5$, $R_7$, and $R_9$ independently represent OH, a compound of formula II, or a compound of formula III, or a compound for formula IV:

(ii) $R_2$, $R_4$, $R_6$, $R_8$, $R_{10}$, $R_{12}$ and $R_{13}$ represent H;
(iii) at least one of $R_1$, $R_3$, $R_5$, $R_7$, $R_9$ and $R_{11}$ represents a compound of formula II, formula III or formula IV, and
(iv) zero, one, or two of $R_1$, $R_3$, $R_5$, $R_7$, $R_9$ and $R_{11}$ represent a heterologous moiety.

In some aspects, the heterologous moiety confers an advantageous property to the inositol phosphate of the disclosure, e.g., a half-life extending moiety that would confer extended plasma half-life, a metabolism-modulating moiety, or a solubility-enhancing heterologous moiety.

In some aspects, the heterologous moiety comprises, e.g., a polyethylene glycol, a polyglycerol, or a combination thereof. In some aspects, the inositol phosphate of the disclosure is myo-inositol hexaphosphate. In some aspects, the concentration of inositol phosphate of the disclosure (e.g., inositol hexaphosphate or an analog or derivative thereof) thereof in each dose is between about 10,000 µg/mL 100,000 µg/mL. In some aspects, the concentration of inositol phosphate of the disclosure (e.g., inositol hexaphosphate or an analog or derivative thereof) in each dose is between about 12.5 mM and about 135 mM.

In some aspects, the dosage is administered as a single daily dose. In some aspects, the dosage is administered as multiple daily doses. In some aspects, the dosage is administered at least once a week. In some aspects, the dosage is administered 2, 3, 4, 5, 6 or 7 times per week. In some aspects, the dosage is administered for at least one week. In some aspects, the dosage is administered for about 2, 3, 4, 5, 6, 7, 8, 9, 10, 11 or 12 weeks. In some aspects, the dosage is administered for at least 12 weeks. In some additional aspects, the dosage is administered for about 13, 14, 15, 16, 17, 18, 19, 20, 21, 22, 23 or 24 weeks. In some further aspects, the dosage is administered for at least 24 weeks. In some ulterior aspects, the dosage is administered for about 25, 26, 27, 28, 29, 30, 31 or 32 weeks. In some other aspects, the dosage is administered for at least 32 weeks.

In some aspects, the administration of the dosage to the subject inhibits the formation and/or growth of hydroxyapatite crystals. In some aspects, the ectopic calcification arises from, or is related to, the pathological crystallization of calcium. In some aspects, the ectopic calcification is calciphylaxis calcification, metastatic calcification, dystrophic calcification, iatrogenic calcification, idiopathic calcification, or subcutaneous ectopic ossification. In some aspects, the consequence of the ectopic calcification is a functional complication, pain, a trophic complication, an infection, or a combination thereof. In some aspects, the function complication is a limitation of range of motion and/or joint function.

In some aspects, the trophic complication is ischemia and/or a lesion. In some aspects, the lesion is necrosis of the cutaneous and/or subcutaneous tissues. In some aspects, administration of the dosage to the subject causes a reduction in lesions as determined by the Bates-Jensen Wound Assessment tool. Bates-Jensen (1992) Decubitus 5(6):20-28. In some aspects, the reduction in lesions comprises a reduction in the severity of the lesions, a reduction in the size of the lesions, and reduction in the duration of the lesions, or a combination thereof. In some aspects, administration of the dosage to the subject causes an improvement in lesion healing.

In some aspects, administration of the dosage to the subject causes a reduction in pain. In some aspects, administration of the dosage to the subject causes an improvement on global wound quality of life (QoL) as determined by using a validated wound-associated QoL questionnaire. Augustin et al. (2017) Int'l. Wound J. 12:1299-1304. In some aspects, the subject has end-stage renal disease. In some aspects, the subject is on hemodialysis. In some aspects, subject is human.

In some aspects, the administration is parenteral. In some aspects, the parenteral administration is by bolus injection or by intravenous infusion. In some aspects, the administration is topical.

The present disclosure also provides a method to treat or prevent calciphylaxis calcification and/or the consequences thereof in a subject in need thereof comprising administering an intravenous dose of an inositol phosphate of the present disclosure, e.g., myo-inositol hexaphosphate, or an analog or derivative thereof, in a dosage of about 6 mg to 9 mg per kg per day to the subject, administered 3 times a week for 12 or 24 weeks, wherein the administration of the dosage effectively treats or prevents calciphylaxis calcification and/ or the consequences thereof in the subject. In some aspects, a dosage of inositol phosphate of about 7 mg per kg per day is administered 3 times a week for 12 or 24 weeks.

The presents disclosure also provides an intravenous dose of an inositol phosphate of the present disclosure, e.g., myo-inositol hexaphosphate, or an analog or derivative thereof, in a dosage of about 6 mg to 9 mg per kg per day to the subject, administered 3 times a week for 12 or 24 weeks as taken by a patient in a therapeutically effective amount sufficient to treat or prevent calciphylaxis calcification and/or the consequences thereof in a subject. In some aspects, a dosage of inositol phosphate of about 7 mg per kg per day is administered 3 times a week for 12 or 24 weeks.

The present disclosure also provides a kit or article of manufacture comprising at least one container comprising a parenteral or topical dose of an inositol phosphate of the present disclosure, e.g., inositol hexaphosphate or an analog or derivative thereof, and instructions for administration according to any method disclosed herein.

BRIEF DESCRIPTION OF THE DRAWINGS/FIGURES

FIG. 1 is a simplified schematic representation of the physiochemical mechanism of action of SNF472, a formulation of myo-inositol hexaphosphate. SNF472 inhibits cardiovascular calcification, e.g., by blocking new calcium crystal formation and the growth of existing crystals. SNF472 is an intravenous formulation of myo-inositol hexaphosphate, which selectively inhibits the formation and growth of hydroxyapatite crystals, the final common pathway in the pathophysiology of vascular calcification. Phase 1 studies in healthy volunteers and hemodialysis patients showed the tolerability and inhibition of hydroxyapatite crystal formation with SNF472. The phase 2 study presented in the Examples section of the present disclosure evaluated wound healing, pain, and quality of life with SNF472 treatment in end-stage renal disease patients on hemodialysis with calciphylaxis.

Figure 3:
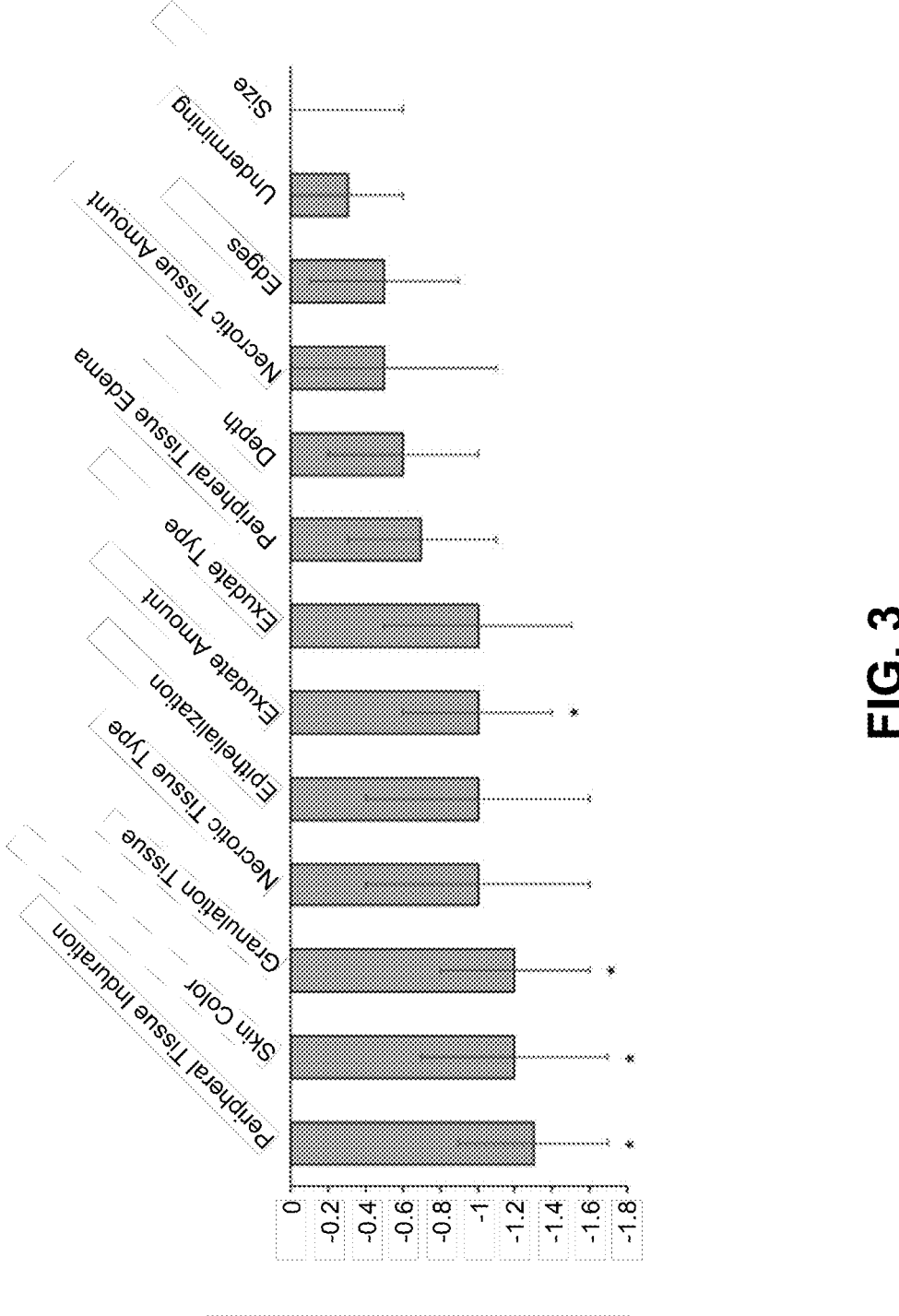

FIG. 3. SNF472 treatment for 12 weeks was associated with improvement from baseline for most of the Bates-Jensen Wound Assessment Tool component scores for the primary lesion. *p<0.05 for the change from baseline.

Figure 4A:
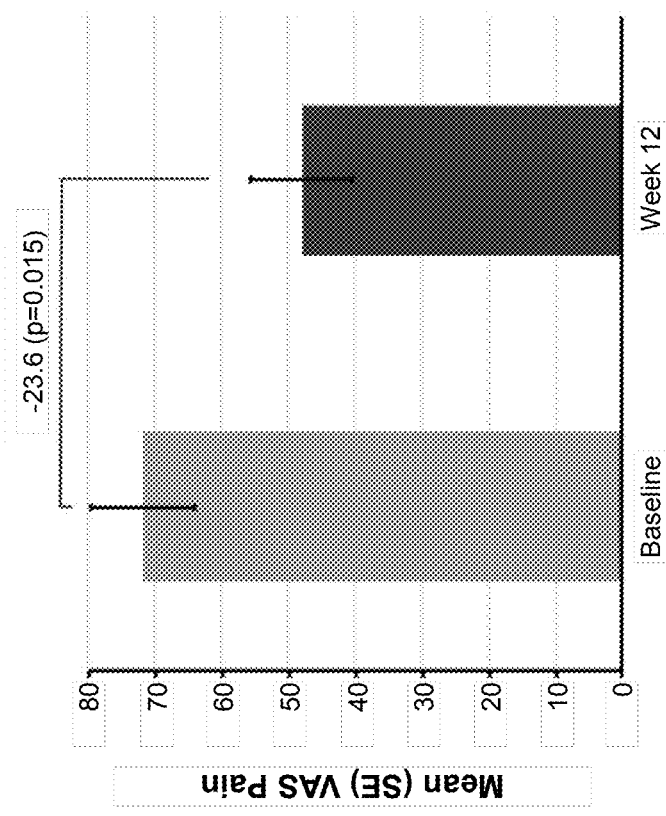

FIG. 4A shows that, in the intention-to-treat population with multiple imputation (n=14), SNF472 treatment resulted in a statistically significant improvement in pain visual analog scale (VAS) score for the primary lesion from baseline to week 12.

Figure 4B:
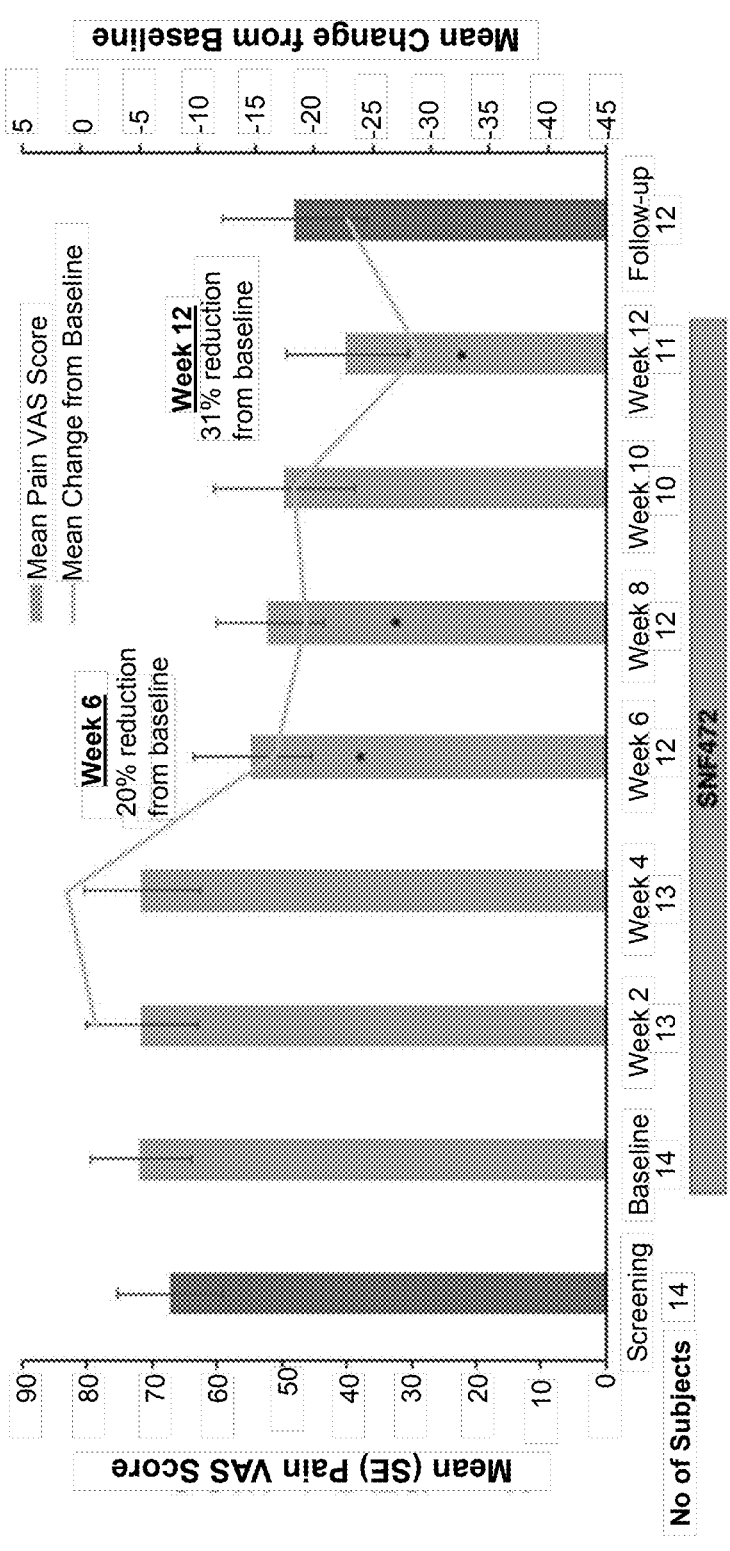

FIG. 4B shows that, using only observed data, SNF472 treatment resulted in statistically significant improvement of pain VAS scores for the primary lesion from baseline to weeks 6, 8, and 12. *p<0.05 for the change from baseline.

Figure 5:
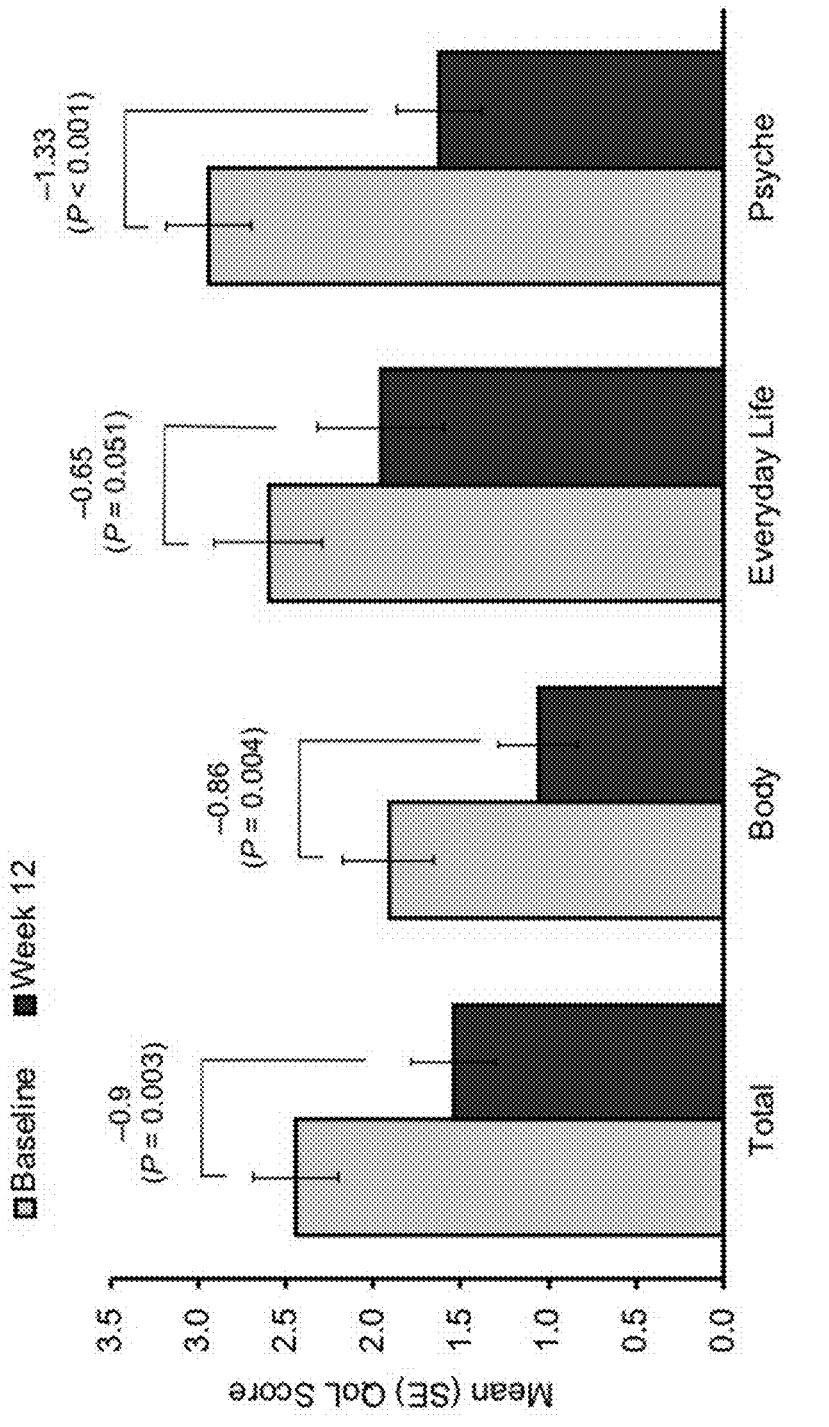

FIG. 5 shows that in the intention-to-treat population with multiple imputation (n=14), SNF472 treatment resulted in subject-reported improvements in quality of life (QoL) scores from baseline to week 12.

Figure 6:
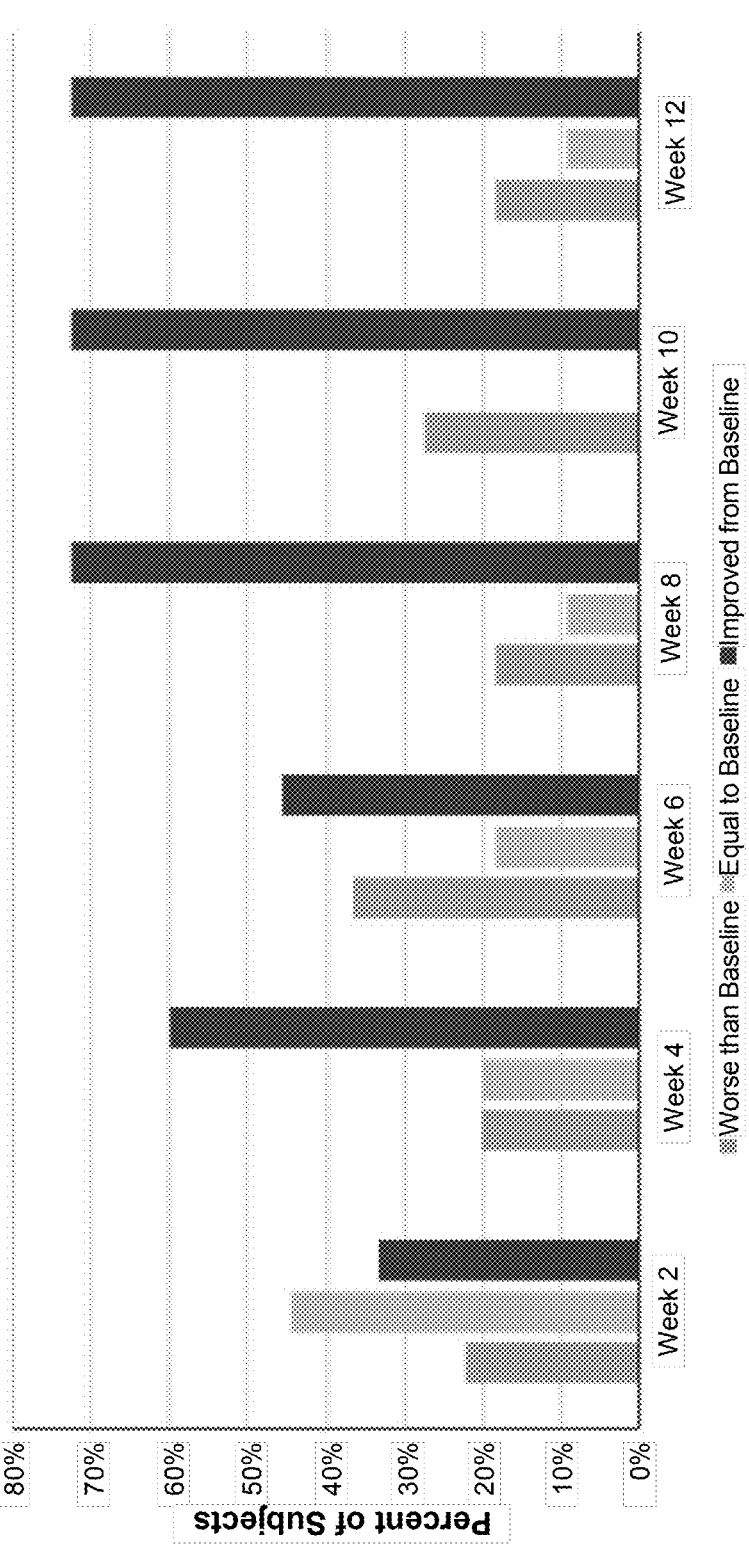

FIG. 6 shows that a qualitative unblinded review of wounds reported improvement from baseline for 8 of 11 (72.7%) subjects at week 12 of SNF472 treatment. One of the 2 patients that worsened did not have detectable SNF472 plasma levels. The other patient was equal to baseline.

Figure 7:
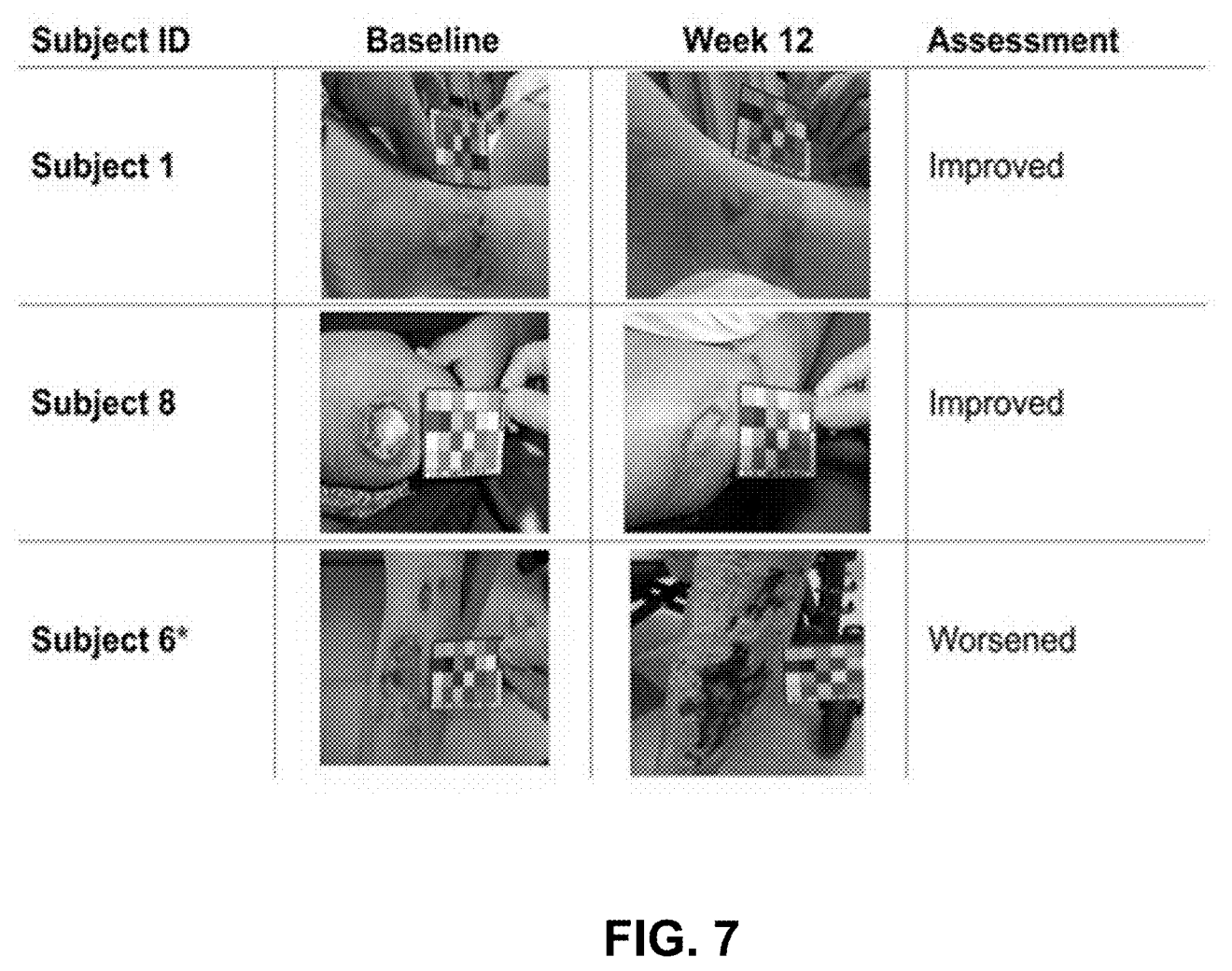

FIG. 7 shows representative images for qualitative wound assessment at baseline and at week 12 for the primary lesion. *Plasma SNF472 concentration was below the limit of quantification in Subject 6 who had lesion worsening; plasma SNF472 concentration was in the expected range in all other subjects.

Figures 8, 9:
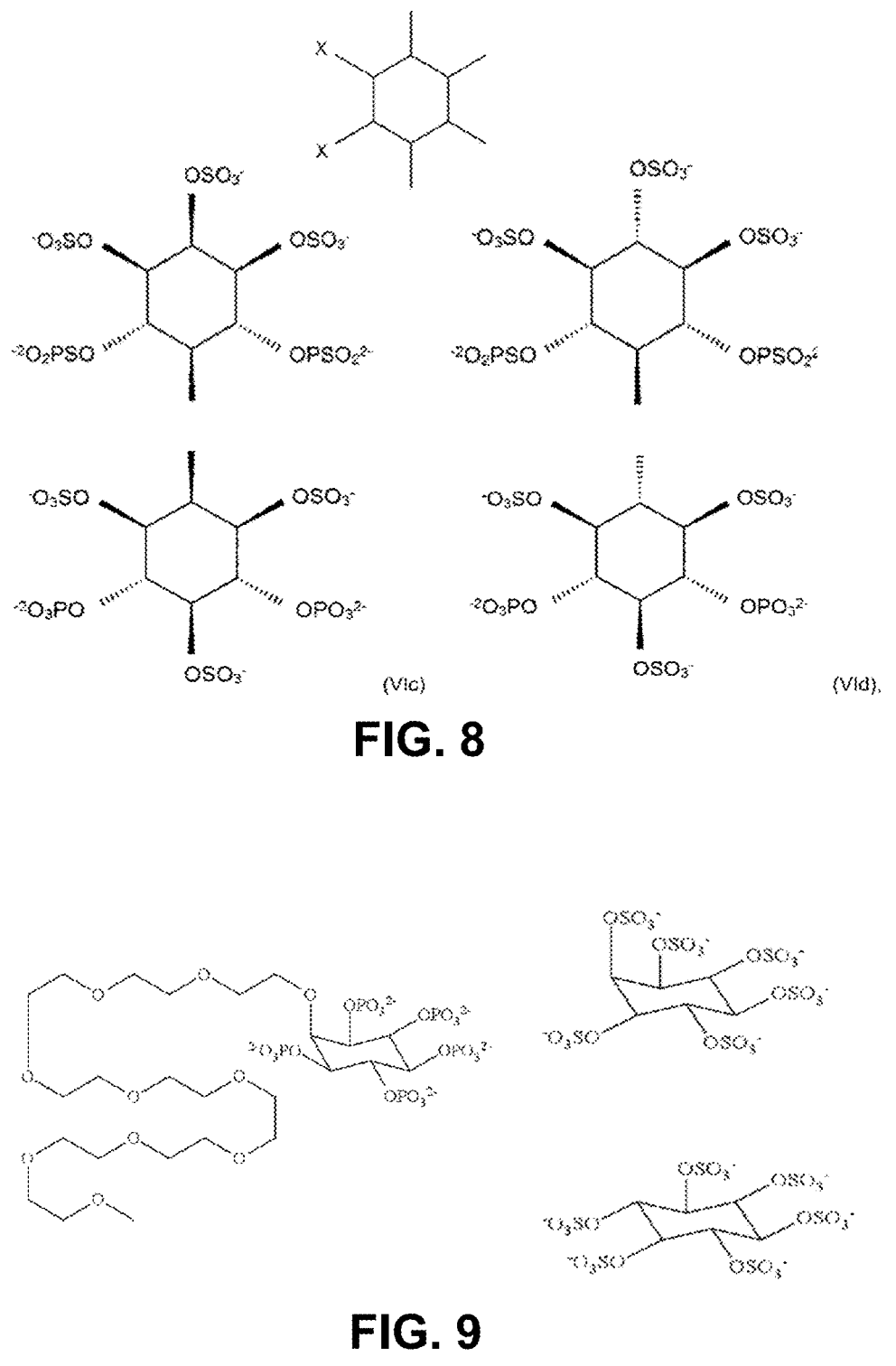

FIG. 8 shows representative inositol phosphate analogs in which two out of six X are $OPSO_2^{2-}$ and the remaining X are $OSO_3$. Four specific forms of 4,6-di-(O-thiophosphate)-inositol-1,2,3,5-tetra-O-sulfate are shown.

FIG. 9 shows inositol phosphate analogs and inositol phosphate derivatives that can be used to practice the methods of the present disclosure. The molecules shown are myo-inositol-pentakisphosphate-2-PEG400, myo-inositol hexakissulfate (myo-inositol hexasulfate), and scyllo-myo-inositol hexakissulfate (scyllo-inositol hexasulfate).

Figure 10:
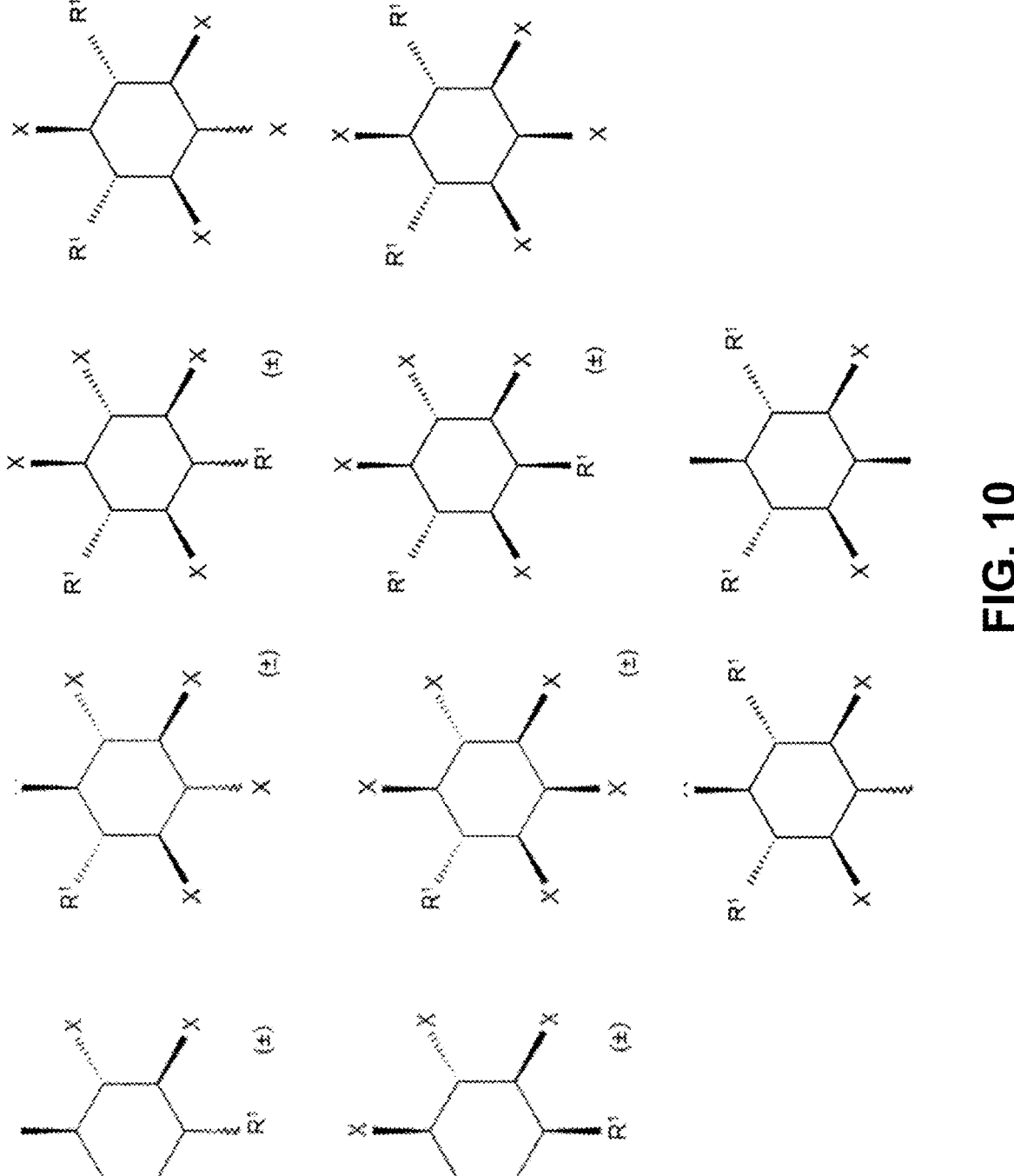

FIG. 10 shows inositol phosphate analogs and inositol phosphate derivatives that can be used to practice the methods of the present disclosure. X represent independently phosphor and/or sulfur containing groups, e.g., phosphate, sulfate, or thiophosphate. $R^1$ represents a heterologous moiety, e.g., PEG or PG.

Figure 11:
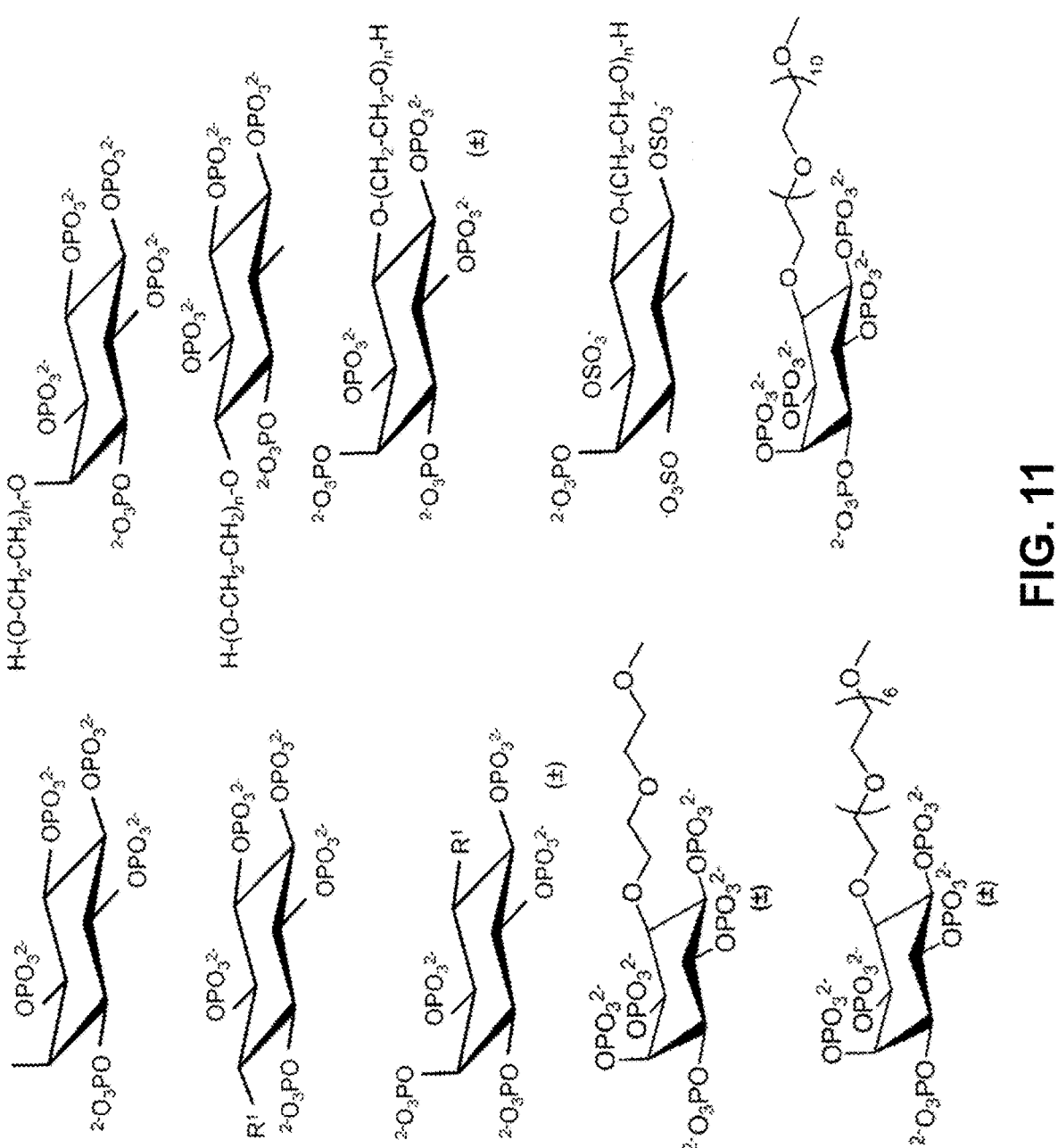

FIG. 11 shows exemplary inositol phosphate analogs and inositol phosphate derivatives that can be used to practice the methods of the present disclosure. $R^1$ represents a heterologous moiety, e.g., PEG or PG. n can be between 2 and 200.

Figure 12:
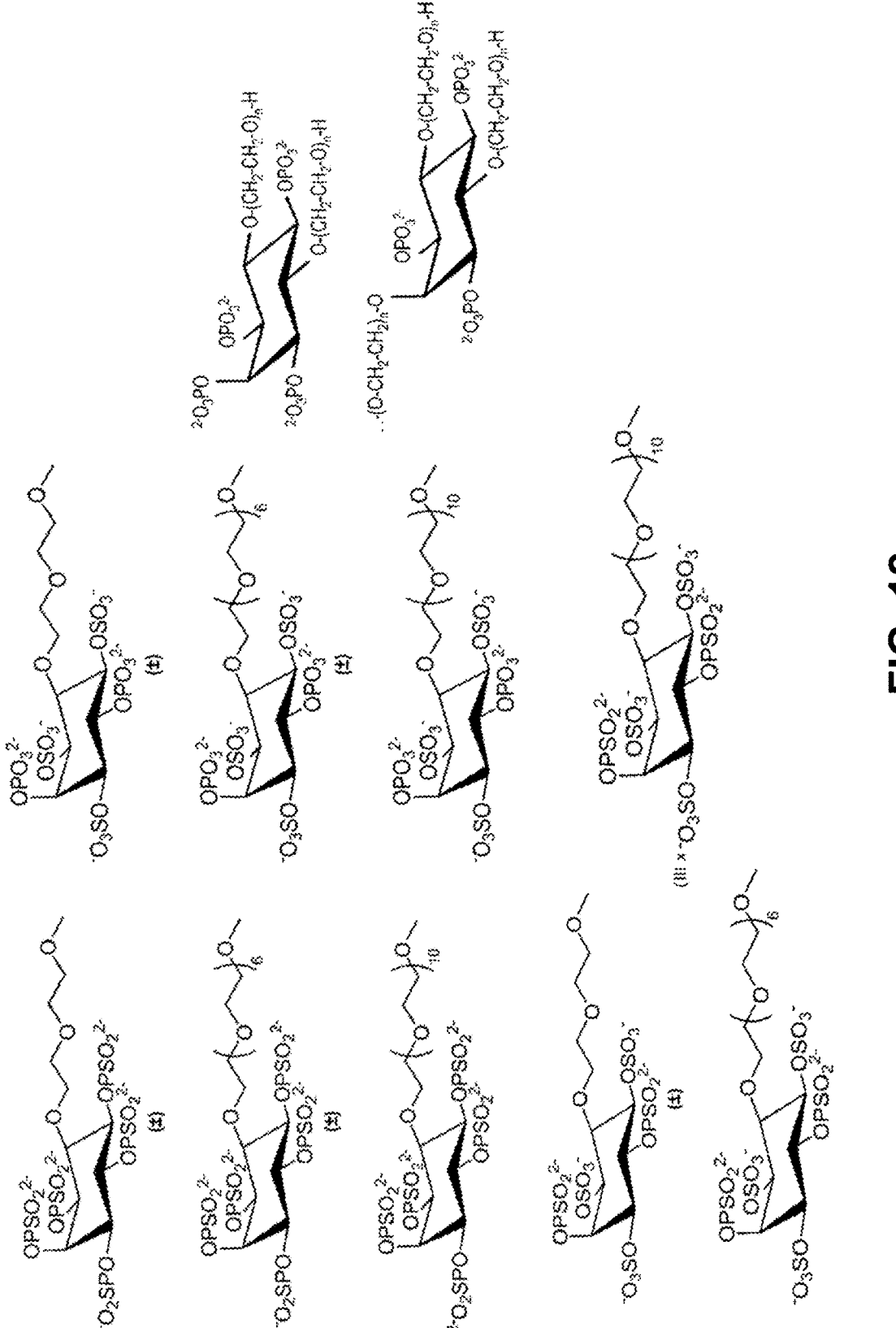

FIG. 12 shows exemplary inositol phosphate analogs and inositol phosphate derivatives that can be used to practice the methods of the present disclosure. n can be between 2 and 200.

Figure 13:
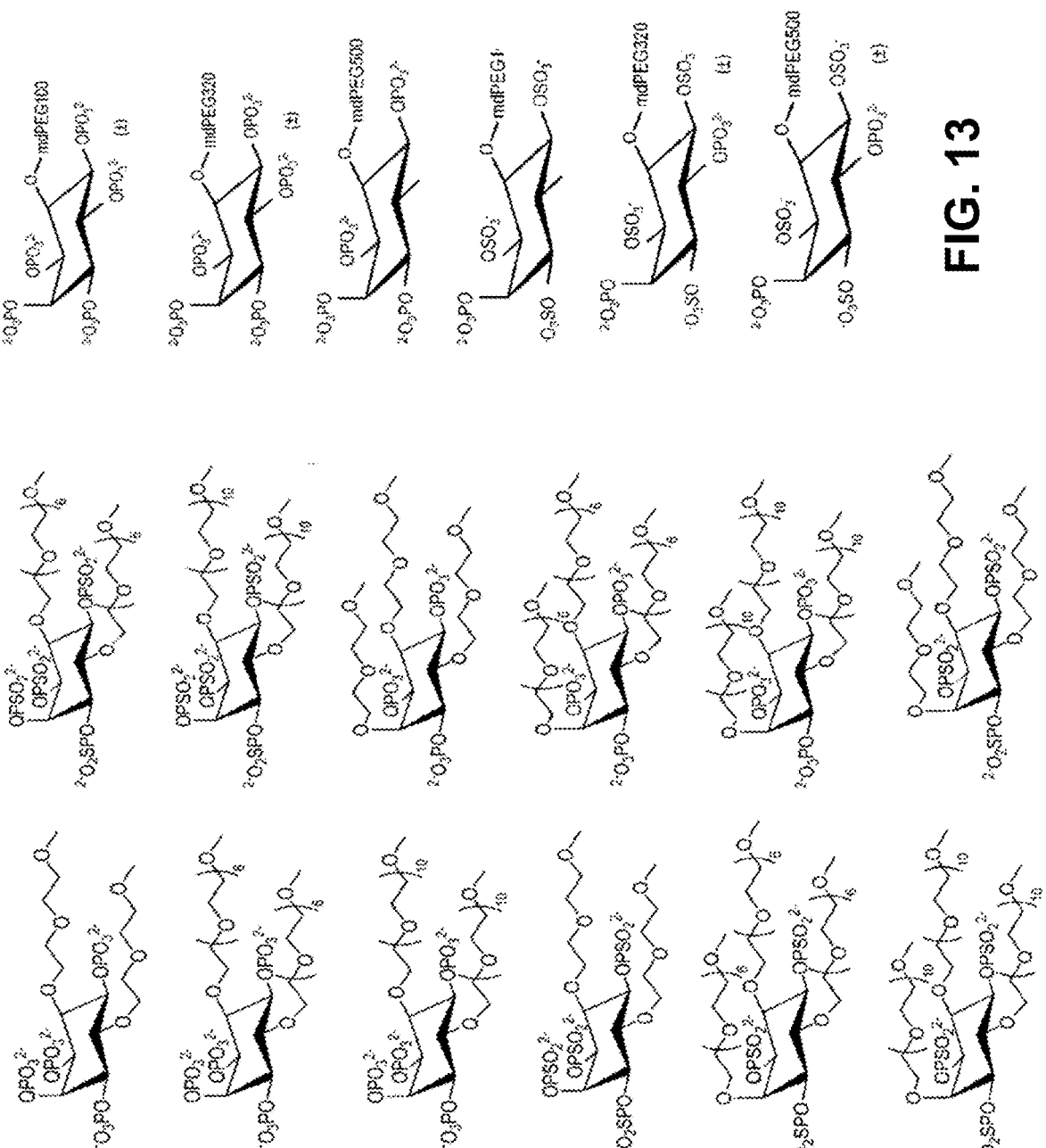

FIG. 13 shows exemplary inositol phosphate analogs and inositol phosphate derivatives that can be used to practice the methods of the present disclosure. n can be between 2 and 200.

DETAILED DESCRIPTION

The present disclosure provides compositions, dosages, dosage regimens, methods, pharmaceutical compositions and formulations, methods of use, articles of manufacture, and kits for the treatment of ectopic calcifications in general, and calciphylaxis calcifications in particular. The disclosure provides method to treat and/or prevent ectopic calcifications and/or the consequences thereof in a subject in need thereof comprising administering at least one dose of an inositol phosphate of the present disclosure (e.g., an inositol phosphate, an inositol phosphate analog, an inositol phosphate derivative, or a combination thereof), in a dosage disclosed herein, e.g., of about 6 mg to 9 mg per kg per day, to the subject, wherein the administration of the dosage effectively treats and/or prevents ectopic calcification and/or the consequences thereof in the subject.

The disclosure also provides dosage forms comprising an amount of inositol phosphate of the present disclosure (e.g., an inositol phosphate, an inositol phosphate analog, an inositol phosphate derivative, or a combination thereof) sufficient to administer a dose disclosed herein, e.g., a dose of about 6 mg to 9 mg per kg, to the subject. Also provided are pharmaceutical compositions and formulations comprising an amount of an inositol phosphate of the present disclosure (e.g., an inositol phosphate, an inositol phosphate analog, an inositol phosphate derivative, or a combination thereof) sufficient to administer, e.g., a dose of about 6 mg to 9 mg per kg to the subject.

The disclosure also provides articles of manufacture and kits comprising at least one vessel or container containing an amount of an inositol phosphate of the present disclosure (e.g., an inositol phosphate, an inositol phosphate analog, an inositol phosphate derivative, or a combination thereof) sufficient to administer, e.g., a dose of about 6 mg to 9 mg per kg to the subject, or multiple doses, as well as instructions to administer such doses according to the methods disclosed herein.

In order that the present disclosure can be more readily understood, certain terms are first defined below. As used in this application, except as otherwise expressly provided herein, each of the following terms shall have the meaning set forth below. Additional definitions are set forth throughout the application.

I. Definitions

The disclosure includes aspects in which exactly one member of the group is present in, employed in, or otherwise relevant to a given product or process. The disclosure includes aspects in which more than one, or all of the group members are present in, employed in, or otherwise relevant to a given product or process.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systéme International de Unites (SI) accepted form. Numeric ranges are inclusive of the numbers defining the range. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention.

Where a value is explicitly recited, it is to be understood that values which are about the same quantity or amount as the recited value are also within the scope of the invention. Where a combination is disclosed, each subcombination of the elements of that combination is also specifically disclosed and is within the scope of the invention. Conversely, where different elements or groups of elements are individually disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

About: The term "about" as used herein to a value or composition that is within an acceptable error range for the particular value or composition as determined by one of ordinary skill in the art, which will depend in part on how the value or composition is measured or determined, i.e., the limitations of the measurement system. For example, "about" can mean within 1 or more than 1 standard deviation per the practice in the art. Alternatively, "about" can mean a range of up to 20%. Furthermore, particularly with respect to biological systems or processes, the terms can mean up to an order of magnitude or up to 5-fold of a value.

When particular values or compositions are provided in the application and claims, unless otherwise stated, the meaning of "about" should be assumed to be within an acceptable error range for that particular value or composition. When the term "about" is used in conjunction with a numerical range, it modifies that range by extending the boundaries above and below the numerical values set forth. Thus, "about 10-20" means "about 10 to about 20." In general, the term "about" can modify a numerical value above and below the stated value by a variance of, e.g., 10 percent, up or down (higher or lower).

And or: "And/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Approximately: As used herein, the term "approximately," as applied to one or more values of interest, refers to a value that is similar to a stated reference value. In certain aspects, the term "approximately" refers to a range of values that fall within 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Comprising: It is understood that wherever aspects are described herein with the language "comprising," otherwise analogous aspects described in terms of "consisting of" and/or "consisting essentially of" are also provided.

Compound: As used herein, the term "compound," is meant to include all isomers and isotopes of the structure depicted. As used herein, the term "isomer" means any geometric isomer, tautomer, zwitterion, stereoisomer, enantiomer, or diastereomer of a compound. Compounds can include one or more chiral centers and/or double bonds and can thus exist as stereoisomers, such as double-bond isomers (i.e., geometric E/Z isomers) or diastereomers (e.g., enantiomers (i.e., (+) or (−)) or cis/trans isomers). The present invention encompasses any and all isomers of the compounds described herein, including stereomerically pure forms (e.g., geometrically pure, enantiomerically pure, or diastereomerically pure) and enantiomeric and stereoisomeric mixtures, e.g., racemates. Enantiomeric and stereomeric mixtures of compounds and means of resolving them into their component enantiomers or stereoisomers are well-known. A compound, salt, or complex of the present disclosure can be prepared in combination with solvent or water molecules to form solvates and hydrates by routine methods. In some aspects, the term compound is used to refer to an inositol phosphate of the present disclosure.

Consequence of ectopic calcification: The terms "consequence of ectopic calcification" or the term "consequences thereof" used in reference to ectopic calcifications refer to any complications related to the presence of an ectopic calcification, e.g., a calciphylaxis calcification. This type of complication can be for example a functional complication (e.g., a limitation of range of motion and joint function), pain, a trophic complication (e.g., ischemia or necrosis of the cutaneous and/or subcutaneous tissues), an infection, or a combination thereof.

Ectopic calcification: The term "ectopic calcification" as used herein refers to all pathological deposits of calcium salts or any bone growth in the tissues, in particular in a soft tissue. Examples of diseases and/or conditions related to the pathological crystallization of calcium include, but are not limited to, aortic stenosis, atherosclerosis, calcinosis cutis, calciphylaxis (CUA), cardiovascular mortality, chondrocalcinosis, coronary artery disease, critical limb ischemia, failure of renal transplant grafts and peripheral arterial disease, general arterial calcification of infancy (GACI), kidney stones, myocardial infarction, nephrocalcinosis, osteoporosis, primary hyperoxaluria (PH), progression of chronic kidney disease, pseudogout, pseudoxanthoma elasticum (PXE), valvular calcification, vascular calcification, and vascular stiffening. In some aspects, the ectopic calcification is, e.g., a metastatic calcification, a dystrophic calcification, an iatrogenic calcification, an idiopathic calcification, a calcification associated with calciphylaxis, a subcutaneous ectopic ossification. In one specific aspect, the ectopic calcification is a calciphylaxis calcification.

Effective Amount: As used herein, the term "effective amount" of a therapeutic agent, in reference to (i) an inositol phosphate of the present disclosure (e.g., an inositol phosphate, an inositol phosphate analog, an inositol phosphate derivative, or a combination thereof), (ii) any dosage form, pharmaceutical composition, or formulation disclosed herein comprising an inositol phosphate of the present disclosure, or (iii) a combination of an inositol phosphate of the present disclosure with one or more additional therapeutic agents), is that amount sufficient to effect beneficial or desired results. In some aspects, the beneficial or desired results are, for example, clinical results, and, as such, an "effective amount" depends upon the context in which it is being applied. For example, in the context of administering a therapeutic agent that treats ectopic calcification, an effective amount of a therapeutic agent is, for example, an amount sufficient to reduce or decrease the size of a calcification and/or to inhibit formation and/or growth of calcifications, as compared to the calcifications observed in the subject prior to the administration of the therapeutic agent, or in a population of control subjects without administration of the therapeutic agent. The term "effective amount" can be used interchangeably with "effective dose," "therapeutically effective amount," or "therapeutically effective dose."

Prophylaxis: As used herein, the term "prophylaxis" refers to a measure taken to maintain health and prevent or delay the onset of a disease or condition or to mitigate its extent and/or severity of the symptoms. Thus, a prophylactic use of a therapeutic agent disclosed herein, for example, (i) an inositol phosphate of the present disclosure (e.g., an inositol phosphate, an inositol phosphate analog, an inositol phosphate derivative, or (ii) a combination thereof), or any dosage form, pharmaceutical composition, or (iv) formulation disclosed herein comprising an inositol phosphate of the present disclosure, or a (iv) combination of an inositol phosphate of the present disclosure with one or more additional therapeutic agents, corresponds to that amount sufficient to effect beneficial or desired results. For example, clinical results that would prevent the development of ectopic calcification or delay the appearance of calcifications in a subject.

Ranges: As described herein, any concentration range, percentage range, ratio range or integer range is to be understood to include the value of any integer within the recited range and, when appropriate, fractions thereof (such as one tenth and one hundredth of an integer), unless otherwise indicated.

SNF472: As used herein, the term "SNF472" refers to an intravenous myo-inositol hexaphosphate formulation. SNF472 is manufactured by dissolving myo-inositol hexaphosphate in saline solution, followed by pH adjustment and aseptic filtration. SNF472 is prepared at three different strengths: (a) (i) 20 mg/mL and (ii) 90 mg/mL in 5 mL single-use vials, formulated in saline solution, pH 5.8 to 6.2 and (b) 30 mg/L in 10 mL single-use vials, formulated in saline solution, pH 5.6 to 6.4.

Soft tissue: The term "soft tissue" refers to a tissue other than bone tissue, which connects, supports, or surrounds other structures and organs of the body.

Subject: By "subject" or "individual" or "animal" or "patient" or "mammal," is meant any subject, particularly a mammalian subject, for whom diagnosis, prognosis, or therapy is desired. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; bears, food animals such as cows, pigs, and sheep; ungulates such as deer and giraffes; rodents such as mice, rats, hamsters and guinea pigs; and so on. In certain aspects, the mammal is a human subject. In other aspects, a subject is a human patient. In a particular aspect, a subject is a human patient with a pathological calcification or at risk of having pathological calcifications. In some embodiments, the subject is a human patient with a pathological calcification, for example an ectopic calcification such as a calciphylaxis calcification in need of treatment.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Therapeutic agent: As used herein, the term "therapeutic agent" is used in a broad sense to include a composition comprising an inositol phosphate of the present disclosure that can provide a significant therapeutic benefit to a subject in need thereof, in particular, a subject suffering from or at risk of developing ectopic calcifications. Thus, a therapeutic agent according to the present disclosure can be, for example, (i) any inositol phosphate of the present disclosure (e.g., an inositol phosphate, an inositol phosphate analog, an inositol phosphate derivative, or a combination thereof), or (ii) any dosage form, pharmaceutical composition, or formulation disclose herein comprising an inositol phosphate of the present disclosure, or (iii) a combination of an inositol phosphate of the present disclosure with one or more additional therapeutic agents, that is administered in an amount sufficient to effect beneficial or desired results.

In some specific aspects, the therapeutic agent is a combined composition comprising any inositol phosphate of the present disclosure and at least an additional therapeutic agent (see, e.g., TABLE 1) or a combination thereof.

The term therapeutic agent also encompasses prophylactic, diagnostic, or imaging agents comprising an inositol phosphate of the present disclosure, wherein the therapeutic agent is administered, e.g., parenterally or topically. Therapeutic agents of the present disclosure include not only agents that treat ectopic calcifications, but also agents that can ameliorate and/or prevent any symptom associated with the presence of a calcification. Thus, as defined herein, the term therapeutic agent would include, for example, agents that can reduce or suppress inflammation, agent that increase the patient's mobility, and agents that reduce pain.

Target tissue: As used herein "target tissue" refers to any one or more tissue types of interest in which the delivery of a therapeutic and/or prophylactic agent comprising an inositol phosphate of the present disclosure would result in a desired biological and/or pharmacological effect. Examples of target tissues of interest include specific tissues, organs, and systems or groups thereof. In particular applications, the target tissue can be subcutaneous tissue.

Topical administration: As used herein, the term "topical administration" refers to any administration of a composition comprising an inositol phosphate of the present disclosure by the local route, for example over the skin, an orifice, or a mucous membrane. Topical administration as used herein, includes the cutaneous, aural, nasal, vaginal, urethral, and rectal routes of administration.

Treating, treatment, therapy: As used herein, the terms "treating" or "treatment" or "therapy" refer to partially or completely alleviating, ameliorating, improving, relieving, delaying onset of, inhibiting progression of, reducing severity of, reducing incidence of one or more symptoms or features of disease, or any combination thereof. For example, "treating" calciphylaxis can refer, e.g., to inhibiting calcification, reducing the size of calcification, increasing survival, increasing mobility, reducing pain, or any combination thereof.

A treatment comprising an inositol phosphate of the present disclosure can be administered to a subject who does not exhibit signs of a disease, disorder, and/or condition, and/or to a subject who exhibits only early signs of a disease, disorder, and/or condition for the purpose of, e.g., (i) decreasing the risk of developing a pathology associated with the disease, disorder, and/or condition, (ii) delaying the onset of the disease, disorder, and/or condition, or a pathology associated with said disease, disorder, and/or condition, or (iii) mitigating the symptoms and/or sequels of the disease, disorder, and/or condition or a pathology associated with said disease, disorder, and/or condition.

Thus, in general, the term "treatment" refers to countering the effects caused as a result of the disease or pathological condition of interest in a subject including (i) inhibiting the disease or pathological condition, in other words, slowing or stopping the development or progression thereof; (ii) relieving the disease or pathological condition, in other words, causing said disease or pathological condition, or the symptoms thereof, to regress; (iii) stabilizing the disease or pathological condition, and (iv) any combination thereof.

ug, uM, uL: As used herein, the terms "ug," "uM," and "uL" are used interchangeably with "µg," "µM," and "µL" respectively.

II. Treatment of Ectopic Calcifications

The present disclosure provides methods to treat and/or prevent ectopic calcifications, e.g., calciphylaxis calcifications, and/or the consequences thereof in a subject in need thereof comprising administering at least one dose of an inositol phosphate of the present disclosure (e.g., inositol hexaphosphate or an analog or derivative thereof, or a combination thereof) in a dosage of about 5 mg to 10 mg per kg per day to the subject (e.g., a dosage of about 6 mg to about 9 mg/kg/day, such as 6 mg/kg/day or 9 mg/kg/day), at least one per week (e.g., once, twice, or three times per week), for a variable period of time (e.g., from about 1 week to about 32 weeks) wherein the administration of the dosage effectively treats and/or prevents ectopic calcification and/or the consequences thereof in the subject.

In the context of the present disclosure, the term "inositol phosphate" as well as the terms "inositol phosphate analog" or "inositol phosphate derivative" refer to compounds encompassed by formula I, the compounds disclosed in Section III of the present disclosure, the compounds disclosed in Section III incorporating one or more heterologous moieties disclose in Section IV, as well as compounds disclosed in the patents and patents application referenced therein, which are herein incorporated by reference in their entireties.

The compounds of the present disclosure do no encompass other phosphate-containing compounds known in the art such as sodium hexametaphosphate, sodium polyphosphate (Graham salts), or pyrophosphate.

As used herein, the term "inositol phosphate" (and grammatical variants thereof) refers to a compound with an inositol ring and one, two, three, four, five, or six phosphate groups, or a combination thereof. Myo-inositol hexaphosphate (IP6) is an exemplary inositol phosphate of the present disclosure. In some aspects, the inositol phosphate is pure (e.g., over 99% of the inositol phosphate species are the same species, for example, IP6) or substantially pure (e.g., at least 90%, 91%, 92%, 93%, 94%, 95%, 96%, 97%, 98% or 99% of the inositol phosphate species are the same species, for example, IP6). In some aspects, the inositol phosphate is a mixture, e.g., comprising variable amounts of IP1, IP2, IP3, IP4, IP5, and IP6. In some aspects, the inositol phosphate is a racemic mixture.

A used herein, the term "inositol phosphate analog" (and grammatical variants thereof) refers to a compound that has a ring with different number of carbons with respect to an inositol ring (i.e., 5 or 7 carbons), and/or has at least one sulfate or thiophosphate group. For example, a compound comprising a ring with 5, 6, or 7 carbons and at least one phosphate, sulfate, or thiophosphate group would be considered an inositol phosphate analog.

As used herein, the term "inositol phosphate derivative" (and grammatical variants thereof) refers to an "inositol phosphate" or "inositol phosphate analog" which has been derivatized with a heterologous moiety (i.e., a group that is not a phosphate, a sulfate, or a thiophosphate). For example, an inositol pentasulfate comprising a polyethylene glycol heterologous moiety, or a myo-inositol hexaphosphate comprising a polyglycerol heterologous moiety would be considered inositol phosphate derivatives.

A used herein, the term "heterologous moiety" (and grammatical variants thereof) refers to a group or substituent in a inositol phosphate derivative which is not a phosphate, a sulfate, or a thiophosphate, and confers a desirable property to such compound. For example, a heterologous moiety (e.g., a polyglycerol or a polyethyleneglycol) can increase the solubility of the compound. In some aspects, a heterologous moiety can confer multiple desirable properties; e.g., polyglycerol and polyethyleneglycol can both increase the solubility of a compound and reduce the clearance rate of the compound.

The terms "inositol phosphate of the disclosure" and "inositol phosphate of the present disclosure," as used herein, and grammatical variants thereof, is a generic term encompassing "inositol phosphate," "inositol phosphate analog," "inositol phosphate derivative," and combinations thereof. In some aspects, the term "inositol phosphate of the present disclosure" encompasses compositions comprising an "inositol phosphate," an "inositol phosphate analog," an "inositol phosphate derivative," or a combination thereof, and at least one additional therapeutic agent (see, e.g., TABLE 1).

Compounds of the present disclosure comprising a ring with 5, 6, or 7 carbons and at least one sulfate, or thiophosphate group but without a phosphate group would still be considered an "inositol phosphate analog" or an "inositol phosphate analog" in the context of the present disclosure. Thus, the term "inositol phosphate of the present disclosure" encompasses not only phosphate-containing compounds but also compounds without phosphate groups that comprise a ring with 5, 6, or 7 carbons and at least one sulfate, or thiophosphate group.

Representative inositol phosphates of the present disclosure are presented in FIGS. 8-13. FIG. 10 present numerous examples of inositol phosphates, all of them in the myo conformation. Besides myo-inositol, the other naturally occurring stereoisomers of inositol are scyllo-, muco-, 1D-chiro-, 1L-chiro-, neo-inositol, allo-, epi-, and cis-inositol. As their names denote, 1L- and 1D-chiro inositol are the only pair of inositol enantiomers, but they are enantiomers of each other, not of myo-inositol. It is to be understood that any exemplary inositol phosphate presented in the disclosure is not limited to the representative conformation displayed. Thus, for example, the examples presented in FIG. 10 would also encompass the corresponding equivalents in scyllo-, muco-, 1D-chiro-, 1L-chiro-, neo-inositol, allo-, epi-, and cis-inositol conformations. In its most stable conformation, the myo-inositol isomer assumes the chair conformation, which moves the maximum number of hydroxyls to the equatorial position, where they are farthest apart from each other. In this conformation, the natural myo isomer has a structure in which five of the six hydroxyls (the first, third, fourth, fifth, and sixth) are equatorial, whereas the second hydroxyl group is axial.

myo      scyllo muco      1D-chiro

13

-continued 1L-chiro neo allo epi cis

As used herein, the terms "dose" or "dose of the present disclosure" refers to a total amount, e.g., in grams or grams/kg, of an inositol phosphate of the present disclosure that would be administered to a subject in need thereof over a 24 hour period.

In the context of the present disclosure, the terms "dosage" or "dosage of the present disclosure" refer to a dose of inositol phosphate of the present disclosure administered to a subject over a period of time.

A dose can be calculated using the accepted standard weight of a subject. For example, ideal body weight (IBW) is estimated as follows: IBW (kg)=50+2.3 kg for each inch over 5 feet (males); IBW (kg)=45.5+2.3 kg for each inch over 5 feet (females). Thus, for example, a dose of inositol hexaphosphate administered as part of a regimen comprising the administration of a dosage of 5 mg/kg per day to a subject, assuming an ideal body weight of 60 kg, would consist of 300 mg of inositol hexaphosphate. For example, dosages can be adjusted based on the subjects age, weight, body surface, renal clearance, sex, pathological state, route of administration, concurrent administration of one or more other drugs, and a wide variety of physiologic and psychological factors using methods known in the art. See, e.g., Pan et al. (2016) Patient Prefer Adherence 10: 549-560; Pai et al. (2012) Pharmacotherapy 32:856-868; Hacker et al. (2009) "Pharmacology: Principles and Practice," Academic Press; and references cited therein, all of which are herein incorporated by reference in their entireties.

The term "mg/kg" as used herein refers to mg of an inositol phosphate of the present disclosure per kg of the body mass (body weight) of the subject.

In general, the effective dose of an inositol phosphate of the present disclosure to be administered according to the methods disclosed herein will depend, for example, on the relative efficacy of the compound concerned, the severity of the disorder treated, and the weight of the subject. In some aspects, the dose of a inositol phosphate of the present disclosure to be administered to a subject can be calculated based, e.g., on its capacity to inhibit crystallization, compared to a reference compound (e.g., myo-inositol hexaphosphate).

For example, if a given inositol phosphate of the present disclosure has a capacity to inhibit crystallization equivalent to the capacity to inhibit crystallization of myo-inositol hexaphosphate, the same dose would be generally used. Conversely, if a given inositol phosphate of the present disclosure has a capacity to inhibit crystallization that is 50% of the capacity to inhibit crystallization of myo-inositol hexaphosphate, a dose that is two-fold the dose of myo-inositol hexaphosphate could be generally used. In other words, the estimated dose of a inositol phosphate of the present disclosure with respect to a myo-inositol hexaphosphate dose would be the reciprocal value of the ratio between their respective capacities to inhibit crystallization (or other measurable property related to the efficacy of the inositol phosphate of the present disclosure to treat ectopic calcifications). Accordingly, $$\text{Dose}_{compound\,x} = \text{Dose}_{IP6} \times 1/\left(\text{Property}_{compound\,x}/\text{Property}_{IP6}\right),$$

wherein Property can be, e.g., capacity to inhibit hydroxyapatite crystallization, capacity to inhibit nucleation, or capacity to reduce, inhibit, or prevent any symptom associated with the ectopic crystallization, e.g., a calciphylaxis calcification.

In some aspects, the measurement of the capacity to inhibit crystallization of an inositol phosphate of the present disclosure is conducted in vitro. In other aspects, the measurement of the capacity to inhibit crystallization of an inositol phosphate of the present disclosure is conducted in vivo.

In some aspects, the inositol phosphate of the present disclosure comprises a compound of formula I, a pharmaceutically acceptable salt thereof, or a combination thereof:

I wherein
(i) $R_1$, $R_3$, $R_5$, $R_7$, $R_9$ and $R_{11}$ independently represent OH, a compound of formula II, or a compound of formula III, or a compound for formula IV

II or

III or

-continued $$IV$$

(ii) $R_2$, $R_4$, $R_6$, $R_8$, $R_{10}$, $R_{12}$ and $R_{13}$ represent H;

(iii) at least one of $R_1$, $R_3$, $R_5$, $R_7$, $R_9$ and $R_{11}$ represents a compound of formula II, formula III or formula IV, and (iv) zero, one, or two of $R_1$, $R_3$, $R_5$, $R_7$, $R_9$ and $R_{11}$ represent a heterologous moiety.

In some aspects, the dose of inositol phosphate of the present disclosure comprises from about 5 mg/kg to about 10 mg/kg of an inositol phosphate, an inositol phosphate analog, an inositol phosphate derivative, or combination thereof, with the proviso that, when the inositol phosphate is myo-inositol hexaphosphate, the dose is not equal to 5 mg/kg or 10 mg/kg. In some aspects, when the disease or condition treated or prevented is related to chronic kidney disease (CKD), for example, calciphylaxis in CKD patients (e.g., stage 5 CKD patients), the dose is not equal to 5 mg/kg or 10 mg/kg. In some aspects, when the dosage regimen comprises daily non-bolus dose administration for at least 14 days, the dose is not equal to 5 mg/kg or 10 mg/kg.

In some aspects, the dose of inositol phosphate of the present disclosure (e.g., myo-inositol hexaphosphate) is between about 5.0 mg/kg and about 6.0 mg/kg, between about 6.0 mg/kg and about 7.0 mg/kg, between about 7.0 mg/kg and about 8.0 mg/kg, between about 8.0 mg/kg and about 9.0 mg/kg, or between about 9.0 mg/kg and about 10.0 mg/kg.

In some aspects, the dose of inositol phosphate of the present disclosure (e.g., myo-inositol hexaphosphate) is between about 5.0 mg/kg and about 5.5 mg/kg, between about 5.5 mg/kg and about 6.0 mg/kg, between about 6.0 mg/kg and about 6.5 mg/kg, between about 6.5 mg/kg and about 7.0 mg/kg, between about 7.0 mg/kg and about 7.5 mg/kg, between about 7.5 mg/kg and about 8.0 mg/kg, between about 8.0 mg/kg and about 8.5 mg/kg, between about 8.5 mg/kg and about 9.0 mg/kg, between about 9.0 mg/kg and about 9.5 mg/kg, or between about 9.5 mg/kg and about 10.0 mg/kg.

In some aspects, the dose of inositol phosphate of the present disclosure (e.g., myo-inositol hexaphosphate) is between about 5.0 mg/kg and about 7.0 mg/kg, between about 6.0 mg/kg and about 8.0 mg/kg, between about 7.0 mg/kg and about 9.0 mg/kg, between about 8.0 mg/kg and about 10.0 mg/kg, between about 5.0 mg/kg and about 8 mg/kg, between about 6.0 mg/kg and about 9.0 mg/kg, between 7.0 mg/kg and about 10.0 mg/kg, between about 5.0 mg/kg and about 9 mg/kg, or between about 6.0 mg/kg and about 10.0 mg/kg.

In some aspects, the dose of inositol phosphate of the present disclosure (e.g., myo-inositol hexaphosphate) is about 5.1 mg/kg, about 5.2 mg/kg, about 5.3 mg/kg, about 5.4 mg/kg, about 5.5 mg/kg, about 5.6 mg/kg, about 5.7 mg/kg, about 5.8 mg/kg, about 5.9 mg/kg, about 6.0 mg/kg, about 6.1 mg/kg, about 6.2 mg/kg, about 6.3 mg/kg, about 6.4 mg/kg, about 6.5 mg/kg, about 6.6 mg/kg, about 6.7 mg/kg, about 6.8 mg/kg, about 6.9 mg/kg, about 7.0 mg/kg, about 7.1 mg/kg, about 7.2 mg/kg, about 7.3 mg/kg, about 7.4 mg/kg, about 7.5 mg/kg, about 7.6 mg/kg, about 7.7 mg/kg, about 7.8 mg/kg, about 7.9 mg/kg, about 8.0 mg/kg, about 8.1 mg/kg, about 8.2 mg/kg, about 8.3 mg/kg, about 8.4 mg/kg, about 8.5 mg/kg, about 8.6 mg/kg, about 8.7 mg/kg, about 8.8 mg/kg, about 8.9 mg/kg, about 9.0 mg/kg, about 9.1 mg/kg, about 9.2 mg/kg, about 9.3 mg/kg, about 9.4 mg/kg, about 9.5 mg/kg, about 9.6 mg/kg, about 9.7 mg/kg, about 9.8 mg/kg, about 9.9 mg/kg, or about 10 mg/kg.

In some aspects, the dose of inositol phosphate of the present disclosure (e.g., myo-inositol hexaphosphate) is between about 5.1 mg/kg and about 10 mg/kg, between about 5.2 mg/kg and about 10 mg/kg, between about 5.3 mg/kg and about 10 mg/kg, between about 5.4 mg/kg and about 10 mg/kg, between about 5.5 mg/kg and about 10 mg/kg, between about 5.6 mg/kg and about 10 mg/kg, between about 5.7 mg/kg and about 10 mg/kg, between about 5.8 mg/kg and about 10 mg/kg, between about 5.9 mg/kg and about 10 mg/kg, between about 6.0 mg/kg and about 10 mg/kg, between about 6.1 mg/kg and about 10 mg/kg, between about 6.2 mg/kg and about 10 mg/kg, between about 6.3 mg/kg and about 10 mg/kg, between about 6.4 mg/kg and about 10 mg/kg, between about 6.5 mg/kg and about 10 mg/kg, between about 6.6 mg/kg and about 10 mg/kg, between about 6.7 mg/kg and about 10 mg/kg, between about 6.8 mg/kg and about 10 mg/kg, between about 6.9 mg/kg and about 10 mg/kg, between about 7.0 mg/kg and about 10 mg/kg, between about 7.1 mg/kg and about 10 mg/kg, between about 7.2 mg/kg and about 10 mg/kg, between about 7.3 mg/kg and about 10 mg/kg, between about 7.4 mg/kg and about 10 mg/kg, between about 7.5 mg/kg and about 10 mg/kg, between about 7.6 mg/kg and about 10 mg/kg, between about 7.7 mg/kg and about 10 mg/kg, between about 7.8 mg/kg and about 10 mg/kg, between about 7.9 mg/kg and about 10 mg/kg, between about 8.0 mg/kg and about 10 mg/kg, between about 8.1 mg/kg and about 10 mg/kg, between about 8.2 mg/kg and about 10 mg/kg, between about 8.3 mg/kg and about 10 mg/kg, between about 8.4 mg/kg and about 10 mg/kg, between about 8.5 mg/kg and about 10 mg/kg, between about 8.6 mg/kg and about 10 mg/kg, between about 8.7 mg/kg and about 10 mg/kg, between about 8.8 mg/kg and about 10 mg/kg, between about 8.9 mg/kg and about 10 mg/kg, between about 9.0 mg/kg and about 10 mg/kg, between about 9.1 mg/kg and about 10 mg/kg, between about 9.2 mg/kg and about 10 mg/kg, between about 9.3 mg/kg and about 10 mg/kg, between about 9.4 mg/kg and about 10 mg/kg, between about 9.5 mg/kg and about 10 mg/kg, between about 9.6 mg/kg and about 10 mg/kg, between about 9.7 mg/kg and about 10 mg/kg, between about 9.8 mg/kg and about 10 mg/kg, between about 9.9 mg/kg and about 10 mg/kg, or between about 10 mg/kg and about 10 mg/kg.

In some aspects, the dose of inositol phosphate of the present disclosure (e.g., myo-inositol hexaphosphate) is between about 5.0 mg/kg and about 5.1 mg/kg, between about 5.0 mg/kg and about 5.2 mg/kg, between about 5.0 mg/kg and about 5.3 mg/kg, between about 5.0 mg/kg and about 5.4 mg/kg, between about 5.0 mg/kg and about 5.5 mg/kg, between about 5.0 mg/kg and about 5.6 mg/kg, between about 5.0 mg/kg and about 5.7 mg/kg, between about 5.0 mg/kg and about 5.8 mg/kg, between about 5.0 mg/kg and about 5.9 mg/kg, between about 5.0 mg/kg and about 6.0 mg/kg, between about 5.0 mg/kg and about 6.1 mg/kg, between about 5.0 mg/kg and about 6.2 mg/kg, between about 5.0 mg/kg and about 6.3 mg/kg, between about 5.0 mg/kg and about 6.4 mg/kg, between about 5.0 mg/kg and about 6.5 mg/kg, between about 5.0 mg/kg and about 6.6 mg/kg, between about 5.0 mg/kg and about 6.7 mg/kg, between about 5.0 mg/kg and about 6.8 mg/kg, between about 5.0 mg/kg and about 6.9 mg/kg, between about 5.0 mg/kg and about 7.0 mg/kg, between about 5.0 mg/kg and about 7.1 mg/kg, between about 5.0 mg/kg and about 7.2 mg/kg, between about 5.0 mg/kg and about 7.3 mg/kg, between about 5.0 mg/kg and about 7.4 mg/kg, between about 5.0 mg/kg and about 7.5 mg/kg, between about 5.0 mg/kg and about 7.6 mg/kg, between about 5.0 mg/kg and about 7.7 mg/kg, between about 5.0 mg/kg and about 7.8 mg/kg, between about 5.0 mg/kg and about 7.9 mg/kg, between about 5.0 mg/kg and about 8.0 mg/kg, between about 5.0 mg/kg and about 8.1 mg/kg, between about 5.0 mg/kg and about 8.2 mg/kg, between about 5.0 mg/kg and about 8.3 mg/kg, between about 5.0 mg/kg and about 8.4 mg/kg, between about 5.0 mg/kg and about 8.5 mg/kg, between about 5.0 mg/kg and about 8.6 mg/kg, between about 5.0 mg/kg and about 8.7 mg/kg, between about 5.0 mg/kg and about 8.8 mg/kg, between about 5.0 mg/kg and about 8.9 mg/kg, between about 5.0 mg/kg and about 9.0 mg/kg, between about 5.0 mg/kg and about 9.1 mg/kg, between about 5.0 mg/kg and about 9.2 mg/kg, between about 5.0 mg/kg and about 9.3 mg/kg, between about 5.0 mg/kg and about 9.4 mg/kg, between about 5.0 mg/kg and about 9.5 mg/kg, between about 5.0 mg/kg and about 9.6 mg/kg, between about 5.0 mg/kg and about 9.7 mg/kg, between about 5.0 mg/kg and about 9.8 mg/kg, between about 5.0 mg/kg and about 9.9 mg/kg, or between about 5.0 mg/kg and about 10 mg/kg.

In some aspects, the dose of inositol phosphate of the present disclosure (e.g., myo-inositol hexaphosphate) is administered once daily, i.e., as a single daily dose. In some aspects, the daily dose can be subdivided into smaller doses and administered separately. Accordingly, in some aspect, the total daily dose can be subdivided into 2, 3, 4 or more sub-doses, i.e., multiple daily doses.

In some aspects, the dose of inositol phosphate of the present disclosure (e.g., myo-inositol hexaphosphate) is administered at least once a week. In some aspects, the dose of inositol phosphate of the present disclosure (e.g., myo-inositol hexaphosphate) is administered at least 2, at least 3, at least 4, at least 5, at least 6 or at least 7 times per week.

In some aspects, the dose of inositol phosphate of the present disclosure (e.g., myo-inositol hexaphosphate) is administered for at least one week. In some aspects, the dose of inositol phosphate of the present disclosure is administered for about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 or about 32 weeks.

In some aspects, the dose of inositol phosphate of the present disclosure (e.g., myo-inositol hexaphosphate) is administered for at least 1 weeks, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks, at least 16 weeks, at least 17 weeks, at least 18 weeks, at least 19 weeks, at least 20 weeks, at least 21 weeks, at least 22 weeks, at least 23 weeks, at least 24 weeks, at least 25 weeks, at least 26 weeks, at least 27 weeks, at least 28 weeks, at least 29 weeks, least 30 weeks, at least 31 weeks, or at least 32 weeks.

In some aspects, the dose of inositol phosphate of the present disclosure (e.g., myo-inositol hexaphosphate) is administered for 1 week to 4 weeks, for 1 week to 8 weeks, for 1 week to 12 weeks, for 1 week to 16 weeks, for 1 week to 20 weeks, for 1 week to 24 weeks, for 1 week to 28 weeks, for 1 week to 32 weeks, for 4 weeks to 8 weeks, for 4 weeks to 12 weeks, for 4 weeks to 16 weeks, for 4 weeks to 20 weeks, for 4 weeks to 24 weeks, for 4 weeks to 28 weeks, for 4 weeks to 32 weeks, for 8 weeks to 12 weeks, for 8 weeks to 16 weeks, for 8 weeks to 20 weeks, for 8 weeks to 24 weeks, for 8 weeks to 28 weeks, for 8 weeks to 32 weeks, for 12 weeks to 16 weeks, for 12 weeks to 20 weeks, for 12 weeks to 24 weeks, for 12 weeks to 28 weeks, for 12 weeks to 32 weeks, for 16 weeks to 20 weeks, for 16 weeks to 24 weeks, for 16 weeks to 28 weeks, for 16 weeks to 32 weeks, for 20 weeks to 24 weeks, for 20 weeks to 28 weeks, for 20 weeks to 32 weeks, for 24 weeks to 28 weeks, for 24 weeks to 32 weeks, or for 28 weeks to 32 weeks.

In a particular aspect, the dose of inositol phosphate of the present disclosure (e.g., a as 6 mg/kg/day or 9 mg/kg/day dose of myo-inositol hexaphosphate) is administered 3 times per week. In a particular aspect, the dose of inositol phosphate of the present disclosure (e.g., a as 6 mg/kg/day or 9 mg/kg/day dose of myo-inositol hexaphosphate) is administered 3 times per week for at least 12 weeks.

In some aspects, the concentration of inositol phosphate of the present disclosure (e.g., myo-inositol hexaphosphate or an analog or derivative thereof, or a combination thereof) in each dose is between about 10,000 μg/mL and about 100,000 μg/mL. In one specific aspect, the concentration of inositol phosphate of the present disclosure (e.g., myo-inositol hexaphosphate or an analog or derivative thereof, or a combination thereof) in each dose is between about 20,000 μg/mL and about 90,000 μg/mL.

In one specific aspect, the concentration of inositol phosphate of the present disclosure (e.g., myo-inositol hexaphosphate or an analog or derivative thereof, or a combination thereof) in each dose is about 20,000 μg/mL. In another specific aspect, the concentration of inositol phosphate of the present disclosure (e.g., inositol hexaphosphate or an analog or derivative thereof, or a combination thereof) in each dose is about 30,000 μg/mL. In yet another specific aspect, the concentration of inositol phosphate of the present disclosure (e.g., inositol hexaphosphate or an analog or derivative thereof, or a combination thereof) in each dose is about 90,000 μg/mL.

In some aspects, the concentration of inositol phosphate of the present disclosure (e.g., myo-inositol hexaphosphate or an analog or derivative thereof, or a combination thereof) in each dose is about 10,000 μg/mL, about 20,000 μg/mL, about 30,000 μg/mL, about 40,000 μg/mL, about 50,000 μg/mL, about 60,000 μg/mL, about 70,000 μg/mL, about 80,000 μg/mL, about 90,000 or about 100,000 μg/mL of inositol phosphate of the present disclosure.

In some aspects, the concentration of inositol phosphate of the present disclosure (e.g., myo-inositol hexaphosphate or an analog or derivative thereof, or a combination thereof) in each dose is between about 20,000 μg/mL and about 100,000 μg/mL, between about 30,000 μg/mL and about 100,000 μg/mL, between about 40,000 μg/mL and about 100,000 μg/mL, between about 50,000 μg/mL and about 100,000 μg/mL, between about 60,000 μg/mL and about 100,000 μg/mL, between about 70,000 μg/mL and about 100,000 μg/mL, between about 80,000 μg/mL and about 100,000 μg/mL, or between about 90,000 μg/mL and about 100,000 μg/mL of inositol phosphate of the present disclosure.

In some aspects, the concentration of inositol phosphate of the present disclosure (e.g., myo-inositol hexaphosphate or an analog or derivative thereof, or a combination thereof) in each dose is between about 10,000 µg/mL and about 20,000 µg/mL, between about 10,000 µg/mL and about 30,000 µg/mL, between about 10,000 µg/mL and about 40,000 µg/mL, between about 10,000 µg/mL and about 50,000 µg/mL, between about 10,000 µg/mL and about 60,000 µg/mL, between about 10,000 µg/mL and about 70,000 µg/mL, between about 10,000 µg/mL and about 80,000 µg/mL, or between about 10,000 µg/mL and about 90,000 µg/mL of inositol phosphate of the present disclosure.

In some aspects, the concentration of inositol phosphate of the present disclosure (e.g., myo-inositol hexaphosphate or an analog or derivative thereof, or a combination thereof) in each dose is between about 10,000 µg/mL and about 20,000 µg/mL, between about 20,000 µg/mL and about 30,000 µg/mL, between about 30,000 µg/mL and about 40,000 µg/mL, between about 40,000 µg/mL and about 50,000 µg/mL, between about 50,000 µg/mL and about 60,000 µg/mL, between about 60,000 µg/mL and about 70,000 µg/mL, between about 70,000 µg/mL and about 80,000 µg/mL, between about 80,000 µg/mL and about 90,000 µg/mL, or between about 90,000 µg/mL and about 100,000 µg/mL of inositol phosphate of the present disclosure.

In some aspects, the concentration of inositol phosphate of the present disclosure (e.g., myo-inositol hexaphosphate or an analog or derivative thereof, or a combination thereof) in each dose is between about 10,000 µg/mL and about 30,000 µg/mL, between about 20,000 µg/mL and about 40,000 µg/mL, between about 30,000 µg/mL and about 50,000 µg/mL, between about 40,000 µg/mL and about 60,000 µg/mL, between about 50,000 µg/mL and about 70,000 µg/mL, between about 60,000 µg/mL and about 80,000 µg/mL, between about 70,000 µg/mL and about 90,000 µg/mL, or between about 80,000 µg/mL and about 100,000 µg/mL of inositol phosphate of the present disclosure.

In some aspects, the concentration of inositol phosphate of the present disclosure (e.g., myo-inositol hexaphosphate or an analog or derivative thereof, or a combination thereof) in each dose is between about 10,000 µg/mL and about 40,000 µg/mL, between about 20,000 µg/mL and about 50,000 µg/mL, between about 30,000 µg/mL and about 60,000 µg/mL, between about 40,000 µg/mL and about 70,000 µg/mL, between about 50,000 µg/mL and about 80,000 µg/mL, between about 60,000 µg/mL and about 90,000 µg/mL, or between about 70,000 µg/mL and about 100,000 µg/mL of inositol phosphate of the present disclosure.

In some aspects, the concentration of inositol phosphate of the present disclosure (e.g., myo-inositol hexaphosphate or an analog or derivative thereof, or a combination thereof) in each dose is between about 10,000 µg/mL and about 50,000 µg/mL, between about 20,000 µg/mL and about 60,000 µg/mL, between about 30,000 µg/mL and about 70,000 µg/mL, between about 40,000 µg/mL and about 80,000 µg/mL, between about 50,000 µg/mL and about 90,000 µg/mL, or between about 60,000 µg/mL and about 100,000 µg/mL of inositol phosphate of the present disclosure.

In some aspects, the concentration of inositol phosphate of the present disclosure (e.g., myo-inositol hexaphosphate or an analog or derivative thereof, or a combination thereof) in each dose is between about 10,000 µg/mL and about 60,000 µg/mL, between about 20,000 µg/mL and about 70,000 µg/mL, between about 30,000 µg/mL and about 80,000 µg/mL, between about 40,000 µg/mL and about 90,000 µg/mL, or between about 50,000 µg/mL and about 100,000 µg/mL of inositol phosphate of the present disclosure.

In some aspects, the concentration of inositol phosphate of the present disclosure (e.g., myo-inositol hexaphosphate or an analog or derivative thereof, or a combination thereof) in each dose is between about 10,000 µg/mL and about 55,000 µg/mL, or between about 55,000 µg/mL and about 100,000 µg/mL of inositol phosphate of the present disclosure.

In some aspects, the concentration of inositol phosphate of the present disclosure (e.g., myo-inositol hexaphosphate or an analog or derivative thereof, or a combination thereof) in each dose is between about 12.5 mM and about 135 mM.

In some aspects, the concentration of inositol phosphate of the present disclosure (e.g., myo-inositol hexaphosphate or an analog or derivative thereof, or a combination thereof) in each dose is between about 12.5 mM and about 125 mM. In some aspects, the concentration of inositol phosphate of the present disclosure (e.g., myo-inositol hexaphosphate or an analog or derivative thereof, or a combination thereof) in each dose is about 25 mM, about 39 mM or about 114 mM.

In some aspects, the concentration of inositol phosphate of the present disclosure (e.g., myo-inositol hexaphosphate or an analog or derivative thereof, or a combination thereof) in each dose is about 12.5 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25, about 26 mM, about 27 mM, about 28 mM, about 29 mM, about 30 mM, about 31 mM, about 32 mM, about 33 mM, about 34 mM, about 35 mM, about 36 mM, about 37 mM, about 38 mM, about 39 mM, about 40 mM, about 41 mM, about 42 mM, about 43 mM, about 44 mM, about 45 mM, about 46 mM, about 47 mM, about 48 mM, about 49 mM, about 50 mM, about 51 mM, about 52 mM, about 53 mM, about 54 mM, about 55 mM, about 56 mM, about 57 mM, about 58 mM, about 59 mM, about 60 mM, about 61 mM, about 62 mM, about 63 mM, about 64 mM, about 65 mM, about 66 mM, about 67 mM, about 68 mM, about 69 mM, or about 70 mM. about 71 mM, about 72 mM, about 73 mM, about 74 mM, about 75 mM, about 76 mM, about 77 mM, about 78 mM, about 79 mM, about 80 mM, about 81 mM, about 82 mM, about 83 mM, about 84 mM, about 85 mM, about 86 mM, about 87 mM, about 88 mM, about 89 mM, about 90 mM, 91 mM, about 92 mM, about 93 mM, about 94 mM, about 95 mM, about 96 mM, about 97 mM, about 98 mM, about 99 mM, about 100 mM, about 101 mM, about 102 mM, about 103 mM, about 104 mM, about 105 mM, about 106 mM, about 107 mM, about 108 mM, about 109 mM, about 110 mM, about 111 mM, about 112 mM, about 113 mM, about 114 mM, about 115 mM, about 116 mM, about 117 mM, about 118 mM, about 119 mM, about 120 mM, about 121 mM, about 122 mM, about 123 mM, about 124 mM, about 125 mM, about 126 mM, about 127 mM, about 128 mM, about 129 mM, about 130 mM, about 131 mM, about 132 mM, about 133 mM, about 134 mM, or about 135 mM.

In some aspects, the concentration of inositol phosphate of the present disclosure (e.g., myo-inositol hexaphosphate or an analog or derivative thereof, or a combination thereof) in each dose is between about 12.5 mM and about 20 mM, between about 20 mM and about 30 mM, between about 30 mM and about 40 mM, between about 40 mM and about 50 mM, between about 50 mM and about 60 mM, between about 60 mM and about 70 mM, between about 70 mM and about 80 mM, between about 80 mM and about 90 mM, between about 90 mM and about 100 mM, between about 100 mM and about 110 mM, between about 110 mM and about 120 mM, between about 120 mM and about 130 mM, or between about 130 mM and about 135 mM.

In some aspects, the concentration of inositol phosphate of the present disclosure (e.g., myo-inositol hexaphosphate or an analog or derivative thereof, or a combination thereof) in each dose is between about 12.5 mM and about 30 mM, between about 20 mM and about 40 mM, between about 30 mM and about 50 mM, between about 40 mM and about 60 mM, between about 50 mM and about 70 mM, between about 60 mM and about 80 mM, between about 70 mM and about 90 mM, between about 80 mM and about 100 mM, between about 90 mM and about 110 mM, between about 100 mM and about 120 mM, or between about 110 mM and about 135 mM.

In some aspects, the concentration of inositol phosphate of the present disclosure (e.g., myo-inositol hexaphosphate or an analog or derivative thereof, or a combination thereof) in each dose is between about 12.5 mM and about 40 mM, between about 20 mM and about 50 mM, between about 30 mM and about 60 mM, between about 40 mM and about 70 mM, between about 50 mM and about 80 mM, between about 60 mM and about 90 mM, between about 70 mM and about 100 mM, between about 80 mM and about 110 mM, between about 90 mM and about 120 mM, or between about 100 mM and about 135 mM.

In some aspects, the concentration of inositol phosphate of the present disclosure (e.g., myo-inositol hexaphosphate or an analog or derivative thereof, or a combination thereof) in each dose is between about 12.5 mM and about 50 mM, between about 20 mM and about 60 mM, between about 30 mM and about 70 mM, between about 40 mM and about 80 mM, between about 50 mM and about 90 mM, between about 60 mM and about 100 mM, between about 70 mM and about 110 mM, between about 80 mM and about 120 mM, between about 90 mM and about 130 mM, or between about 100 mM and about 135 mM.

In some aspects, the concentration of inositol phosphate of the present disclosure (e.g., myo-inositol hexaphosphate or an analog or derivative thereof, or a combination thereof) in each dose is between about 12.5 mM and about 60 mM, between about 20 mM and about 70 mM, between about 30 mM and about 80 mM, between about 40 mM and about 90 mM, between about 50 mM and about 100 mM, between about 60 mM and about 110 mM, between about 70 mM and about 120 mM, between about 80 mM and about 130 mM, or between about 90 mM and about 135 mM.

In some aspects, the concentration of inositol phosphate of the present disclosure (e.g., myo-inositol hexaphosphate or an analog or derivative thereof, or a combination thereof) in each dose is between about 12.5 mM and about 135 mM, between about 20 mM and about 135 mM, between about 30 mM and about 135 mM, between about 40 mM and about 135 mM, between about 50 mM and about 135 mM, between about 60 mM and about 135 mM, between about 70 mM and about 135 mM, between about 80 mM and about 135 mM, between about 90 mM and about 135 mM, between about 100 mM and about 135 mM, about 110 mM and about 135 mM, between about 120 mM and about 135 mM, or between about 130 mM and about 135 mM.

In some aspects, the concentration of inositol phosphate of the present disclosure (e.g., myo-inositol hexaphosphate or an analog or derivative thereof, or a combination thereof) in each dose is between about 12.5 mM and about 20 mM, between about 12.5 mM and about 30 mM, between about 12.5 mM and about 40 mM, between about 12.5 mM and about 50 mM, between about 12.5 mM and about 60 mM, between about 12.5 mM and about 70 mM, between about 12.5 mM and about 80 mM, between about 12.5 mM and about 90 mM, between about 12.5 mM and about 100 mM, between about 12.5 mM and about 110 mM, about 12.5 mM and about 120 mM, between about 12.5 mM and about 130 mM, or between about 12.5 mM and about 135 mM.

In some aspects, the dose of inositol phosphate of the present disclosure (e.g., myo-inositol hexaphosphate or an analog or derivative thereof, or a combination thereof) can be administered parenterally such as, for example, intravenously, intraperitoneally, intramuscularly, intra-arterially or subcutaneously. Alternatively, the compound can be administered as a component of a hemodialysis, hemofiltration, or peritoneal dialysis solution. In some aspects, the parenteral administration is by bolus injection or by intravenous infusion. In some aspects, the administration is topical.

In some aspects, inositol phosphates of the present disclosure can be administered by any appropriate method, e.g., a method that provokes a non-bolus type release or effect, such as intravascular (for example intravenous) infusion, other parenteral (subcutaneous, subcutaneous depot, intraperitoneal, intramuscular, intradermal, intrathecal, epidural, spinal or others known to a person skilled in the art), topical (intranasal, inhalation, intravaginal, transdermal or others known to a person skilled in the art), enteral (oral, sublingual, rectal, etc.) administrations, oral, spinal, intraperitoneal preparations or others known to a person skilled in the art.

As used herein, "parenteral administration" of a composition comprising an inositol phosphate of the present disclosure includes any route of administration characterized by physical breaching of a tissue of a subject and administration of the composition through the breach in the tissue. Parenteral administration thus includes, but is not limited to, administration of a composition comprising an inositol phosphate of the present disclosure by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

In the particular case of patients treated with dialysis, a very appropriate method of administration consists of an administration (e.g, a non-bolus type administration) of an inositol phosphate of the present disclosure via the dialysis apparatus (before or after the filter) instead of directly injecting the inositol phosphate of the present disclosure into the patient intravenously. Thus, blood can be treated with the inositol phosphate of the present disclosure (e.g., myo-inositol hexaphosphate) as it leaves the patient and circulates through the dialysis circuit and, when the blood containing the inositol phosphate of the present disclosure returns to the body, the inositol phosphate of the present disclosure has been introduced into the blood in a manner that presents a series of advantages.

In the case of dialysis patients, administration of an inositol phosphate of the present disclosure (e.g., myo-inositol hexaphosphate) via the dialysis apparatus allows the blood to equilibrate with the dialysis fluid prior to returning to the body; thus, although inositol phosphate of the present disclosure (e.g., myo-inositol hexaphosphate) can sequester ionic calcium, this fact is compensated when the blood passes through the dialysis filter thereby eliminating said side effect and significantly improving the safety profile.

As used herein, the terms "prolonged release," "slow release," or "non-bolus," refer to an administration form that slowly releases an inositol phosphate of the present disclosure (e.g., myo-inositol hexaphosphate) into the bloodstream, thus allowing significant levels to be maintained in plasma for a longer period of time than for a "bolus-type" administration. A bolus-type administration comprises, e.g., fast intravenous injection, for example less than 10 seconds (or less than 20, 30, 40, 50, 60 second), or intravenous infusion over less than approximately 3 minutes, 4 minutes, 5 minutes, 6 minutes, 7 minutes, 8 minutes, 9 minutes or 10 minutes.

In a particular aspect of the present disclosure, myo-inositol hexaphosphate (or a formulation comprising myo-inositol hexaphosphate such as SNF472) is administered intravenously via intravenous infusion. In another particular aspect of the present disclosure, myo-inositol hexaphosphate is administered subcutaneously. In another particular aspect of the present disclosure, myo-inositol hexaphosphate is administered topically.

In some aspect, when an inositol phosphate of the present disclosure (e.g., myo-inositol hexaphosphate) is administered to a patient undergoing dialysis such administration (e.g., intravenous administration via infusion) can occur during a dialysis treatment.

In some aspects, the inositol phosphate of the present disclosure (e.g., myo-inositol hexaphosphate) is administered before a dialysis treatment. In some aspects, the inositol phosphate of the present disclosure is administered after a dialysis treatment.

In some aspects, the inositol phosphate of the present disclosure (e.g., myo-inositol hexaphosphate) is administered about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 our or about 48 hours before a dialysis treatment.

In some aspects, the inositol phosphate of the present disclosure (e.g., myo-inositol hexaphosphate) is administered about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 our or about 48 hours after a dialysis treatment.

In some aspects, the administration of the dosage of inositol phosphate of the present disclosure (e.g., myo-inositol hexaphosphate) to the subject inhibits the formation and/or growth of hydroxyapatite crystals and their deposition in ectopic calcifications. In some aspects, the ectopic calcification is, e.g., a calciphylaxis calcification, a metastatic calcification, a dystrophic calcification, an iatrogenic calcification, an idiopathic calcification, or a subcutaneous ectopic ossification.

In some aspects, the consequence of the ectopic calcification is, e.g., (i) a functional complication, (ii) pain, (iii) atrophic complication, (iv) an infection, or (v) a combination thereof. In some aspects, the function complication is, e.g., a limitation of range of motion and/or joint function. In some aspects, the trophic complication is, e.g., ischemia and/or a lesion. In some aspects, the lesion is, e.g., necrosis of the cutaneous and/or subcutaneous tissues.

In some aspects, administration of the dosage of inositol phosphate of the present disclosure (e.g., myo-inositol hexaphosphate) to the subject causes a reduction in lesions, e.g., as determined by the Bates-Jensen Wound Assessment tool or other methods known in the art. Bates-Jensen (1992), supra. In some aspects, the reduction in lesions comprises, e.g., a reduction in the severity of the lesions, a reduction in the size of the lesions, and reduction in the duration of the lesions, or a combination thereof. In some aspects, administration of the dosage of inositol phosphate of the present disclosure to the subject causes an improvement in lesion healing. In some aspects, administration of the dosage of inositol phosphate of the present disclosure to the subject causes a reduction in pain.

In some aspects, administration of the dosage of inositol phosphate of the present disclosure (e.g., myo-inositol hexaphosphate) to the subject causes an improvement on global wound quality of life (QoL) as determined by using a validated wound-associated QoL questionnaire or other methods known in the art. Augustin (2017), supra. In some aspects, the subject has end-stage renal disease. In some aspects, the subject is on hemodialysis. In some aspects, subject is human.

The present disclosure also provides a method to treat or prevent calciphylaxis calcification and/or the consequences thereof in a subject in need thereof comprising administering an intravenous dose of myo-inositol hexaphosphate in a dosage of about 6 mg to 9 mg per kg per day to the subject, administered 3 times a week for 12 or 24 weeks, wherein the administration of the dosage effectively treats or prevents calciphylaxis calcification and/or the consequences thereof in the subject. In some aspects, a dosage of about 7 mg per kg per day is administered to the subject 3 times a week for 12 or 24 weeks.

The presents disclosure also provides an intravenous dose of myo-inositol hexaphosphate in a dosage of about 6 mg to 9 mg per kg per day to the subject, administered 3 times a week for 12 or 24 weeks as taken by a patient in a therapeutically effective amount sufficient to treat or prevent calciphylaxis calcification and/or the consequences thereof in a subject. In some aspects, a dosage of about 7 mg per kg per day is administered to the subject 3 times a week for 12 or 24 weeks.

The present disclosure also provides a kit or article of manufacture comprising at least one container comprising a parenteral or topical dose of an inositol phosphate of the present disclosure and instructions for administration according to any method disclosed herein.

III. Inositol Phosphate Compositions

The inositol phosphates of the present disclosure comprise, as discussed above, compounds of formula I, a pharmaceutically acceptable salt thereof, or a combination thereof:

wherein (i) at least one of $R_1$, $R_3$, $R_5$, $R_7$, $R_9$ and $R_{11}$ independently represent OH, a compound of formula II, or a compound of formula III, or a compound for formula IV:

(ii) $R_2$, $R_4$, $R_6$, $R_8$, $R_{10}$, $R_{12}$ and $R_{13}$ represent H;

(iii) at least one of $R_1$, $R_3$, $R_5$, $R_7$, $R_9$ and $R_{11}$ represents a compound of formula II, formula III or formula IV, and (iv) zero, one, or two of $R_1$, $R_3$, $R_5$, $R_7$, $R_9$ and $R_{11}$ represent a heterologous moiety.

The formulas disclosed herein are meant to encompass any diastereomer.

In some aspects, at least one of $R_1$, $R_3$, $R_5$, $R_7$, $R_9$ and $R_{11}$ independently represents H, —X, —OX, —NHX, —NX$_2$, —SX, —OSO$_3$HX, —OSO$_3$X$_2$ or a compound of formula II, formula III or formula IV, where each X independently represents H, $C_{1-30}$ alkyl, $C_{2-30}$ alkynyl or Cy$_1$, where $C_{1-30}$ alkyl, $C_{2-30}$ alkenyl and $C_{2-30}$ alkynyl are independently optionally substituted with one or more $R_{14}$ and where Cy$_1$ is optionally substituted by one or more $R_{15}$;

Cy$_1$ represents a carbocyclic or heterocyclic three- to 10-membered ring, which can be saturated, partially unsaturated or aromatic, where said heterocycle has between one and four heteroatoms selected from amongst O, S and N, where said ring can be bound to the rest of the molecule via any available C atom and where Cy$_1$ is optionally fused to between one and four five- or six-membered rings, each saturated, partially unsaturated or aromatic, carbocyclic or heterocyclic, and where said fused heterocycle can contain one or two heteroatoms selected from amongst O, N and S; each $R_{13}$ independently represents H, $C_{1-30}$ alkyl, —NH$_2$, —NHC$_{1-30}$alkyl or N(C$_{1-30}$alkyl)$_2$, where each $C_{1-30}$ alkyl is independently optionally substituted with one or more halogen, —OH, —CN and —NO$_2$ groups; and each $R_{14}$ and $R_{15}$ independently represents —OH, $C_{1-30}$ alkoxy, $C_{1-30}$ alkyithionyl, $C_{1-30}$ acyloxy, phosphate, halogen, trihalo $C_{1-30}$ alkyl, nitrile azide.

In some aspects, each X independently represents H, $C_{1-30}$ alkyl or Cy$_1$, where $C_{1-30}$ alkyl is optionally substituted by one or more $R_{14}$ and where Cy$_1$ is optionally substituted by one or more $R_{15}$; and each $R_{14}$ and $R_{15}$ independently represents —OH, $C_{1-30}$ alkoxy, $C_{1-30}$ alkyithionyl, $C_{1-30}$ acyloxy, phosphate, halogen, trihaloC$_{1-30}$alkyl, nitrile or azide. In some aspects, each X represents H, $C_{1-30}$alkyl or Cy$_1$. In some aspects, each X represents H.

In some aspects, at least one of radicals $R_1$, $R_3$, $R_5$, $R_7$, $R_9$ and $R_{11}$ independently represents a compound of formula II, formula III or formula IV, each $R_{13}$ independently represents H, $C_{1-30}$ alkyl, —NH$_2$, —NHC$_{1-30}$ alkyl or —N(C$_{1-30}$ alkyl)$_2$, where each $C_{1-30}$ alkyl is independently optionally substituted by one or more halogen, —OH, —CN and —NO$_2$ groups; and $R_2$, $R_4$, $R_6$, $R_8$, $R_{10}$ and $R_{12}$ independently represent H.

In another aspect, $R_1$, $R_3$, $R_5$, $R_7$, $R_9$ and $R_{11}$ independently represent a compound of formula II, formula III, or formula IV, each $R_{13}$ independently represents H or $C_{1-30}$alkyl, where each $C_{1-30}$alkyl is independently optionally substituted by one or more halogen, —OH, —CN and —NO$_2$ groups; and $R_2$, $R_4$, $R_6$, $R_8$, $R_{10}$ and $R_{12}$ independently represent H.

In another aspect, $R_1$, $R_3$, $R_5$, $R_7$, $R_9$ and $R_{11}$ independently represent a compound of formula II, formula III, or formula IV, each $R_{13}$ independently represents H or $C_{1-30}$alkyl; and $R_2$, $R_4$, $R_6$, $R_8$, $R_{10}$ and $R_{12}$ independently represent H.

In another aspect, $R_1$, $R_3$, $R_5$, $R_7$, $R_9$ and $R_{11}$ independently represent a compound of formula II, formula III or formula IV, each $R_3$ independently represents H; and $R_2$, $R_4$, $R_6$, $R_8$, $R_{10}$ and $R_{12}$ independently represent H.

In a particular aspect, the compound is inositol hexaphosphate (IP6). In other aspects, the compound is inositol monophosphate (IP1), inositol diphosphate (IP2), inositol triphosphate (IP3), inositol tetraphosphate (IP4), or inositol pentaphosphate (IP5). In some aspects, compound comprises a combination of IP1, IP2, IP3, IP4, IP6 and IP6. In some aspects, the IP6 can form other inositol phosphates (IP5, IP4, IP3, IP2, IP1) by dephosphorylation in vivo. Inositol is assumed to mean any isomeric form of the molecule.

The inositol phosphates of the present disclosure also encompass compounds that are produced a metabolites during physiological dephosphorylation (or desulfation or dethiosulfation in the case of compounds comprising sulfate or thiophosphate groups).

In some aspects, the compound administered in a dosage according to the methods disclosed herein is a prodrug that after undergoing hydrolysis or other intracellular or extra-cellular processing yields an inositol phosphate of the present disclosure.

The inositol phosphates of the present disclosure encompass also any combination of the inositol phosphate, inositol phosphate analogs, and derivatives thereof disclosed herein.

All compounds of formula I contain C—O—P or C—O—S bonds, which provide the compounds with an affinity for calcium-containing crystals and a sufficiently labile bond to be hydrolyzed in vivo, thereby preventing irreversible binding to calcium-containing crystals such as the hydroxyapatite (HAP) in bone, which would have a negative impact on bone remodeling, as is the case with bisphosphonates when administered long term as said compounds contain P—C—P bonds that cannot be hydrolyzed by the body. At the other extreme are phosphorylated compounds that do not contain said C—O—P bonds, such as pyrophosphates, the P—O—P bonds of which mean that they are too readily hydrolyzed in the intestine, thus meaning that only parenteral administration is feasible. The compounds of the present disclosure, with C—O—P bonds, C—O—S bonds, and combinations thereof represent an adequate midpoint due to the efficacy thereof and the fact that the body presents mechanisms for eliminating said compounds, thus reducing the risk of side effects (e.g., compounds with P—C—P bonds can present half-lives of several months which in vivo, thereby affecting, e.g., bone remodeling).

The term "alkyl" or "alkyl group" in the context of the present disclosure refers to a saturated hydrocarbon moiety, which can be linear, branched, cyclic or cyclic with linear or branched side chains. The term alkyl includes partially unsaturated hydrocarbons such as propenyl. Examples are methyl, ethyl, n- or isobutyl, n- or cyclohexyl. The term alkyl can extend to alkyl groups linked or bridged by hetero atoms. Hetero atoms in the context of the present invention are nitrogen (N), sulfur (S) and oxygen (O).

An "amine function" or "amine group" is a function NR'R", with R' and R" selected independently from hydrogen and $C_1$-$C_5$ alkyl. In some embodiments, R' and R" are selected from hydrogen and $C_1$-$C_3$ alkyl. A "hydroxy function" or "hydroxy group" is OH. A "thiol function" or "thiol group" is SH. A "carboxylic acid function" or "carboxylic acid group" is COOH or its anion, $COO^-$. A "carboxylic amide" is CONR'R", with R' and R" independently having the meanings indicated above. A "sulfonic acid" is $SO_3H$. A "sulfonic acid amide" is $SO_2NR'R"$, with R' and R" independently having the meanings indicated above.

A "$C_1$-$C_3$ alkyl" in the context of the present disclosure refers to a saturated linear or branched hydrocarbon having 1, 2, or 3 carbon atoms, wherein one carbon-carbon bond can be unsaturated and one $CH_2$ moiety can be exchanged for oxygen (ether bridge). Non-limiting examples for a $C_1$-$C_3$ alkyl are methyl, ethyl, propyl, prop-2-enyl and prop-2-inyl.

A "$C_1$-$C_5$ alkyl" in the context of the present disclosure refers to a saturated linear or branched hydrocarbon having 1, 2, 3, 4 or 5 carbon atoms, wherein one or two carbon-carbon bond can be unsaturated and one $CH_2$ moiety can be exchanged for oxygen (ether bridge). Non-limiting examples for a $C_1$-$C_5$ alkyl include the examples given for $C_1$-$C_3$ alkyl above, and additionally n-butyl, 2-methylpropyl, tert-butyl, 3-methylbut-2-enyl, 2-methylbut-3-enyl, 3-methylbut-3-enyl, n-pentyl, 2-methylbutyl, 3-methylbutyl, 1,1-dimethylpropyl, 1,2-dimethylpropyl, 1,2-dimethylpropyl, but-3-enyl, but-3-inyl and pent-4-inyl.

A "$C_3$-$C_{10}$ alkyl" in the context of the present disclosure refers to a saturated linear or branched hydrocarbon having 3, 4, 5, 6, 7, 8, 9 or 10 carbon atoms, wherein 1, 2 or 3 carbon-carbon bonds can be unsaturated and one $CH_2$ moiety can be exchanged for oxygen (ether bridge).

The term "$C_{1-30}$ alkyl," as a group or part of a group, refers to a linear or branched chain alkyl group containing between 1 and 30 carbon atoms including, amongst others, methyl, ethyl, propyl, isopropyl, butyl, isobutyl, sec-butyl, tert-butyl, pentyl, hexyl, decyl and dodecyl groups.

The term "$C_{2-30}$ alkenyl" refers to a linear or branched alkyl chain containing between 2 and 30 carbon atoms and also contains one or more double bonds. Examples include, amongst others, ethenyl, 1-propenyl, 2-propenyl, isopropenyl 1-butenyl, 2-butenyl, 3-butenyl and 1,3-butadienyl.

The term "$C_{2-30}$ alkynyl" refers to a linear or branched alkyl chain containing between 2 and 30 carbon atoms and also contains one or more triple bonds. Examples include, amongst others, ethynyl, 1-propynyl, 2-propynyl, 1-butynyl, 2-butynyl, 3-butynyl and 1,3-butadiynyl.

A "$Cy_1$ group" refers to a three- to 10-membered carbocyclic or heterocyclic ring that can be saturated, partially unsaturated or aromatic and which is bound to the rest of the molecule via any available C atom. When heterocyclic, $Cy_1$ contains between one and four heteroatoms selected from amongst N, O and S. Moreover, $Cy_1$ can optionally be fused with up to four five- or six-membered carbocyclic or heterocyclic rings, which can be saturated, partially unsaturated or aromatic. If the fused ring is a heterocycle, said ring contains one or two heteroatoms selected from amongst N, O and S. Examples of $Cy_2$ include, amongst others, phenyl, naphthyl, thienyl, furyl, pyrrolyl, thiazolyl, isothiazolyl, imidazolyl, pyrazolyl, 1,2,3-triazolyl, 1,2,4-triazolyl, tetrazolyl, 1,3,4-thiadiazolyl, 1,2,4-thiadiazolyl, pyridyl, pyrazinyl, pyrimidinyl, pyridazinyl, benzimidazolyl, benzofuranyl, isobenzofuranyl, indolyl, isoindolyl, benzothiophenyl, benzothiazolyl, cyclopropyl, cyclobutyl, cyclopentyl, cyclohexyl, cycloheptyl, azetidinyl and aziridinyl.

A "$C_{1-30}$ alkoxy group," as a group or part of a group, refers to an —$OC_{1-30}$alkyl group, where the $C_{1-30}$alkyl part has the same meaning as above. Examples include methoxy, ethoxy, propoxy, isopropoxy, butoxy, isobutoxy, sec-butoxy and tert-butoxy.

A "$C_{1-30}$ alkylthionyl group" as a group or part of a group refers to an —$SOC_{1-30}$alkyl group, where the $C_{1-30}$alkyl part has the same meaning as above. Examples include methylthionyl, ethylthionyl, propyithionyl, isopropyithionyl, butylthionyl, isobutyithionyl, see-butylthionyl and tert-butylthionyl.

A "$C_{1-30}$ acyloxy group" as a group or part of a group refers to a —$COC_{1-30}$alkyl group, where the $C_{1-30}$alkyl part has the same meaning as above. Examples include acetyl, ethanoyl, propanoyl and 2,2-diisopropylpentanoyl.

A "halogen radical" or the halo abbreviation thereof refers to fluorine, chlorine, bromine and iodine.

A "trihalo $C_{1-30}$ alkyl group" refers to a group resulting from the substitution of three hydrogen atoms of a $C_{1-30}$alkyl group by three halogen radicals as defined above. Examples include, amongst others, trifluoromethyl, tribromomethyl, trichloromethyl, triiodomethyl, trifluoroethyl, tribromoethyl, trichloroethyl, triiodoethyl, tribromopropyl, trichloropropyl and triiodopropyl.

An "—$NHC_{1-30}$ alkyl group" refers to a group resulting from the substitution of one hydrogen atom of an —$NH_2$ group by a $C_{1-30}$alkyl group as defined above. Examples include, amongst others, methylamine, ethylamine, propylamine, butylamine and pentylamine.

A "—$N(C_{1-30}$alkyl$)_2$ group" refers to a group resulting from the substitution of two hydrogen atoms of an —$NH_2$ group by a $C_{1-30}$alkyl group as defined above. Examples include, amongst others, dimethylamine, diethylamine, diisopropylamine, dibutylamine and diisobutylamine.

The expression "optionally substituted by one or more" signifies the possibility that a group can be substituted by one or more, e.g., by 1, 2, 3 or 4 substituents. In some aspects, a group can be substituted by 1, 2 or 3 substituents and even by 1 or 2 substituents provided that the group has sufficient positions that can be substituted available. If present, the substituents can be the same or different and can be located at any available position.

In some aspects, the inositol phosphates of the present disclosure used, e.g., in the methods and compositions disclosed herein, comprise the compounds disclosed in International Publication Nos. WO2017098033 and WO2017098047, and U.S. Appl. Publ. No. U.S. Pat. No.

9,358,243B2, all of which are herein incorporated by reference in their entireties. In some aspects, the inositol phosphates of the present disclosure used, e.g., in the methods and compositions disclosed herein, comprise the compounds disclosed in FIGS. 8, 9, 10, 11, 12 and 13.

In some aspects, the inositol phosphates, inositol phosphate analogs, and derivatives thereof used, e.g., in the methods and compositions disclosed herein, comprise compounds of formula (V), formula (VI), or formula (VII):

(V)

(VI)

(VII)

wherein
each X independently is selected from $OPO_3^{2-}$, $OPSO_2^{2-}$, or $OSO_3^-$; Z is an alkyl chain comprising 1 to 3 carbon and/or hetero atoms, optionally comprising a group X, wherein X is also selected from $OPO_3^{2-}$, $OPSO_2^{2-}$, or $OSO_3^-$; and,
$R^1$ is an optional heterologous moiety (see Section IV below). In some aspects, the molecule comprises more than one heterologous moiety, in which case the heterologous moieties can be the same or be different.

In some aspects, Z, as used in formula (V), is $CH_2$, CHX, $CHR^1$, $CXR^1$, $CH_2$—$CH_2$, $CH_2$—CHX, CHX—CHX, $CHR^1$—CHX, $CXR^1$—CHX, $CHR^1$—$CH_2$, $CXR^1$—$CH_2$, $CHR^1$—CHOH, $CH_2$—$CH_2$—$CH_2$, $CH_2$—O—$CH_2$, CHOH—$CH_2$—$CH_2$, CHOH—CHOH—$CHR^1$, CHOH—$CHR^1$—CHOH, CHX—$CH_2$—$CH_2$, $CH_2$—CHX—$CH_2$, CHX—CHX—$CH_2$, CHX—$CH_2$—CHX or CHX—$CHR^1$—CHX, wherein X independently is selected from $OPO_3^{2-}$, $OPSO_2^{2-}$, and $OSO_3^-$.

In some aspects, Z, as used in formula (V), is $(CHX)_p CHX(CHX)_q$; wherein p and q each independently from the other have a value from 0 to 2, with the proviso that (p+q) has a value of 0, 1 or 2; one or two or three X can be a heterologous moiety (e.g., PEG) and the remaining X are independently selected from $OPO_3^{2-}$, $OPSO_2^{2-}$, and $OSO_3^-$. In some aspects, not all X of Z are $OPO_3^{2-}$. In some aspects, not all X of Z are $OSO_3^-$.

In some aspects, one, two, or three of the X in compounds of formula (V), formula (VI), or formula (VII) can be a heterologous moiety and the remaining X can independently be selected from $OPO_3^{2-}$, $OPSO_2^{2-}$, or $OSO_3^-$.

Formula (V) above describes a five-membered, six-membered, or seven-membered alkyl ring, and the optional heterologous moiety or moieties is/are attached to one of the carbon atoms forming the ring.

In some aspects, the inositol phosphates, inositol phosphate analogs, and derivatives thereof used, e.g., in the methods and compositions disclosed herein, comprise compounds of formula (VIII) or formula (IX):

(VIII)

(IX)

wherein:
(a) $X^2$ is $OSO_3^-$, and $X^1$, $X^3$, $X^4$, $X^5$ and $X^6$ are independently selected from $OPO_3^{2-}$, $OPSO_2^{2-}$ or $OSO_3^-$;
(b) $X^1$, $X^3$ and $X^5$ are $OPO_3^{2-}$ and $X^2$, $X^4$ and $X^6$ are $OSO_3^-$;
(c) $X^1$, $X^3$ and $X^5$ are $OSO_3^{2-}$ and $X^2$, $X^4$ and $X^6$ are $OPO_3^{2-}$;
(d) $X^4$, $X^5$ and $X^6$ are $OSO_3^-$ and $X^1$, $X^2$ and $X^3$ are $OSO_3^{2-}$;
(e) $X^4$, $X^5$ and $X^6$ are $OPO_3^{2-}$ and $X^1$, $X^2$ and $X^3$ are $OSO_3^-$;
(f) $X^2$ and $X^5$ are $OSO_3^{2-}$ and $X^1$, $X^3$, $X^4$, and $X^6$ are $OPO_3^-$;
(g) $X^2$ and $X^5$ are $OSO_3^-$ and $X^1$, $X^3$, $X^4$, and $X^6$ are $OPO_3^{2-}$;
(h) $X^2$ and $X^3$ are $OSO_3^{2-}$ and $X^1$, $X^4$, $X^5$, and $X^6$ are $OSO_3^-$; or,
(i) $X^2$ and $X^3$ are $OSO_3^-$ and $X^1$, $X^4$, $X^5$ and $X^6$ are $OPO_3^{2-}$.

In some aspects, the inositol phosphates of the present disclosure or metabolites thereof can be detected and/or quantified using the methods disclosed in U.S. Pat. No. 9,612,250B2, which is herein incorporated by reference in its entirety. See also, U.S. Pat. Nos. 8,377,909B2 and 8,778,912 and U.S. Pat. Appl. Publ. No. US20070066574.

The compounds disclosed herein can be present in any form commonly used in pharmaceutical technology. Particular aspects include, but are not limited to, the sodium salt, magnesium salt, potassium salt, ammonium salt, free acid, or a mixture of the preceding forms. Other pharmaceutically acceptable salts are known to the skilled artisan and can be obtained, inter alia, from Haynes et al. (2005) J. Pharmaceutical Sci. 94:2111-2120.

IV. Heterologous Moieties

In some aspects, the inositol phosphate derivatives of the present disclosure can comprise at least one heterologous moiety conferring an advantageous property with respect to a corresponding molecule lacking such heterologous moiety or moieties. Exemplary advantageous properties that can be conferred by a heterologous moiety or a combination thereof to an inositol phosphate or inositol phosphate analogs are:

(i) increase in solubility;

(ii) increase or decrease in degradation or metabolisation rate;

(iii) increase or decrease in plasma half-life;

(iv) decrease in liver metabolisation rate;

(v) increase or decrease in renal clearance;

(vi) decrease in precipitation;

(vii) increase in shelf life;

(viii) increase or decrease in rate of permeation through physiological barriers (e.g., blood-brain barrier, intestinal wall, peritoneum, vascular walls, skin, etc);

(ix) thermal stability;

(x) resistance to phosphatases and/or sulfatases;

(xi) any combination thereof.

The advantageous properties disclosed above can be evaluated or quantified using methods known in the art without undue experimentation.

In some aspects, the heterologous moiety is, e.g., a polyethylene glycol (PEG), a polyglycerol (PG).

PEG:

In certain aspects, the heterologous moiety comprises a polyethylene glycol (PEG) characterized by a formula $R^3$—$(O$—$CH_2$—$CH_2)_n$— or $R^3$-$(0$-$CH_2$—$CH_2)_n$—$O$— with $R^3$ being hydrogen, methyl or ethyl and n having a value from 2 to 200.

In some aspects, n has a value of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 189, 181, 182, 183, 184, 185, 186, 187, 188, 189, 190, 191, 192, 193, 194, 195, 196, 197, 198, 199, or 200.

In some aspects, n is between 2 and 10, between 10 and 20, between 20 and 30, between 30 and 40, between 40 and 50, between 50 and 60, between 60 and 70, between 70 and 80, between 80 and 90, between 90 and 100, between 100 and 110, between 110 and 120, between 120 and 130, between 130 and 140, between 140 and 150, between 150 and 160, between 160 and 170, between 170 and 180, between 180 and 190, or between 190 and 200.

In some specific aspects, n has a value from 3 to 200, from 3 to 20, from 10 to 30, or from 9 to 45.

In some aspects, the PEG is a branched PEG. Branched PEGs have three to ten PEG chains emanating from a central core group.

In certain embodiments, the PEG moiety is a monodisperse polyethylene glycol. In the context of the present disclosure, a monodisperse polyethylene glycol (mdPEG) is a PEG that has a single, defined chain length and molecular weight. mdPEGs are typically generated by separation from the polymerization mixture by chromatography. In certain formulae, a monodisperse PEG moiety is assigned the abbreviation mdPEG.

In some aspects, the PEG is a Star PEG. Star PEGs have 10 to 100 PEG chains emanating from a central core group.

In some aspects, the PEG is a Comb PEGs. Comb PEGs have multiple PEG chains normally grafted onto a polymer backbone.

In certain aspects, the PEG has a molar mass between 100 g/mol and 3000 g/mol, particularly between 100 g/mol and 2500 g/mol, more particularly of approx. 100 g/mol to 2000 g/mol. In certain aspects, the PEG has a molar mass between 200 g/mol and 3000 g/mol, particularly between 300 g/mol and 2500 g/mol, more particularly of approx. 400 g/mol to 2000 g/mol.

In some aspects, the PEG is $PEG_{100}$, $PEG_{200}$, $PEG_{300}$, $PEG_{400}$, $PEG_{500}$, $PEG_{600}$, $PEG_{700}$, $PEG_{800}$, $PEG_{900}$, $PEG_{1000}$, $PEG_{1100}$, $PEG_{1200}$, $PEG_{1300}$, $PEG_{1400}$, $PEG_{1500}$, $PEG_{1600}$, $PEG_{1700}$, $PEG_{1800}$, $PEG_{1900}$, $PEG_{2000}$, $PEG_{2100}$, $PEG_{2200}$, $PEG_{2300}$, $PEG_{2400}$, $PEG_{2500}$, $PEG_{1600}$, $PEG_{1700}$, $PEG_{1800}$, $PEG_{1900}$, $PEG_{2000}$, $PEG_{2100}$, $PEG_{2200}$, $PEG_{2300}$, $PEG_{2400}$, $PEG_{2500}$, $PEG_{2600}$, $PEG_{2700}$, $PEG_{2800}$, $PEG_{2900}$, or $PEG_{3000}$. In one particular aspect, the PEG is $PEG_{400}$. In another particular aspect, the PEG is $PEG_{2000}$.

PG: In some aspects, the heterologous moiety is a polyglycerol (PG) described by the formula $((R_3$—$O$—$(CH_2$—$CHOH$—$CH_2O)_n$—$)$ with R3 being hydrogen, methyl or ethyl, and n having a value from 3 to 200. In some aspects, n has a value from 3 to 20. In some aspects, n has a value from 10 to 30. In some alternatives of these embodiments, n has a value from 9 to 45. In some aspects, the heterologous moiety is a branched polyglycerol described by the formula $(R^3$—$O$—$(CH_2$—$CHOR^5$—$CH_2$—$O)_n$—$)$ with $R^5$ being hydrogen or a linear glycerol chain described by the formula $(R^3$—$O$—$(CH_2$—$CHOH$—$CH_2$—$O)_n$—$)$ and $R^3$ being hydrogen, methyl or ethyl. In some aspects, the heterologous moiety is a hyperbranched polyglycerol described by the formula $(R^3$—$O$—$(CH_2$—$CHOR^5$—$CH_2$—$O)_n$—$)$ with $R^5$ being hydrogen or a glycerol chain described by the formula $(R^3$—$O$—$(CH_2$—$CHOR^6$—$CH_2$—$O)_n$—$)$, with $R^6$ being hydrogen or a glycerol chain described by the formula $(R^3$—$O$—$(CH_2$—$CHOR^7$—$CH_2$—$O)_n$—$)$, with $R^7$ being hydrogen or a linear glycerol chain described by the formula $(R^3$—$O$—$(CH_2$—$CHOH$—$CH_2$—$O)_n$—$)$ and $R^3$ being hydrogen, methyl or ethyl. Hyperbranched glycerol and methods for its synthesis are described in Oudshorn et al. (2006) Biomaterials 27:5471-5479; Wilms et al. (20100 Acc. Chem. Res. 43, 129-41, and references cited therein.

In certain aspects, the PG has a molar mass between 100 g/mol and 3000 g/mol, particularly between 100 g/mol and 2500 g/mol, more particularly of approx. 100 g/mol to 2000 g/mol. In certain aspects, the PG has a molar mass between 200 g/mol and 3000 g/mol, particularly between 300 g/mol and 2500 g/mol, more particularly of approx. 400 g/mol to 2000 g/mol.

In some aspects, the PG is $PG_{100}$, $PG_{200}$, $PG_{300}$, $PG_{400}$, $PG_{500}$, $PG_{600}$, $PG_{700}$, $PG_{800}$, $PG_{900}$, $PG_{1000}$, $PG_{1100}$, $PG_{1200}$, $PG_{1300}$, $PG_{1400}$, $PG_{1500}$, $PG_{1600}$, $PG_{1700}$, $PG_{1800}$, $PG_{1900}$, $PG_{2000}$, $PG_{2100}$, $PG_{2200}$, $PG_{2300}$, $PG_{2400}$, $PG_{2500}$, $PG_{1600}$, $PG_{1700}$, $PG_{1800}$, $PG_{1900}$, $PG_{2000}$, $PG_{2100}$, $PG_{2200}$, $PG_{2300}$, $PG_{2400}$, $PG_{2500}$, $PG_{2600}$, $PG_{2700}$, $PG_{2800}$, $PG_{2900}$, or $PG_{3000}$. In one particular aspect, the PG is $PG_{400}$. In another particular aspect, the PG is $PG_{2000}$.

V. Pharmaceutical Compositions

The present disclosure also provides pharmaceutical compositions for use in the methods for the prevention and/or treatment of ectopic calcifications disclosed herein, wherein the pharmaceutical composition comprises at least one inositol phosphate of the present disclosure (e.g., myo-inositol hexaphosphate or an analog or derivative thereof or a combination thereof). In some aspects, the pharmaceutical composition comprises an inositol phosphate of the present disclosure alone or together with one or more pharmaceutically acceptable excipients or carriers.

The term "excipient" as used herein refers to a substance which helps absorption of the elements of the pharmaceutical composition, stabilizes said elements, activates or helps preparation of the composition. Thus, examples of excipients used in parenteral formulations include, but are not limited to, antimicrobial agents (e.g., benzalkonium chloride, metacresol, thimerosal), co-solvents (e.g., ethanol), buffers and pH adjusting factors (e.g., carbonate, citrate, phosphate solutions).

As is the case for the excipient, the "pharmaceutically acceptable vehicle" is a substance used in the composition to dilute any of the components contained therein to a determined volume or weight. The pharmaceutically acceptable vehicle is an inert substance or a substance with an analogous action to any of the elements comprising the pharmaceutical composition of the present disclosure. The role of said vehicle is to allow the incorporation of other elements, allow better dosing and administration or to provide consistency and shape to the composition.

Pharmaceutical compositions can comprise from approximately 1% to approximately 95% active ingredient (i.e., an inositol phosphate of the present disclosure or a combination, alone or in combination, e.g., with one or more therapeutic agents disclosed in TABLE 1). In some aspects, e.g., the pharmaceutical compositions of the present disclosure can comprise from approximately 20% to approximately 90% active ingredient (i.e., an inositol phosphate of the present disclosure or a combination, alone or in combination, e.g., with one or more therapeutic agents disclosed in TABLE 1).

Formulations of a pharmaceutical composition suitable for parenteral administration comprise the active ingredient, e.g., an inositol phosphate of the present disclosure, combined with a pharmaceutically acceptable carrier, such as sterile water or sterile isotonic saline. Such formulations can be prepared, packaged, or sold in a form suitable for bolus administration or for continuous administration. Injectable formulations can be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations can further comprise one or more additional ingredients including, but not limited to, suspending, stabilizing, or dispersing agents.

In some aspects, in a formulation for parenteral administration, the active ingredient, e.g., an inositol phosphate of the present disclosure, is provided in dry (i.e., powder or granular) form for reconstitution with a suitable vehicle (e.g., sterile pyrogen-free water) prior to parenteral administration of the reconstituted composition.

The pharmaceutical compositions can be prepared, packaged, or sold in the form of a sterile injectable aqueous or oily suspension or solution. This suspension or solution can be formulated according to the known art, and may comprise, in addition to the active ingredient, e.g., an inositol phosphate of the present disclosure, additional ingredients such as the dispersing agents, wetting agents, or suspending agents described herein. Such sterile injectable formulations can be prepared using a non-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides.

Other parentally-administrable formulations which are useful include those which comprise the active ingredient in microcrystalline form, in a liposomal preparation, or as a component of a biodegradable polymer system. Compositions for sustained release or implantation can comprise pharmaceutically acceptable polymeric or hydrophobic materials such as an emulsion, an ion exchange resin, a sparingly soluble polymer, or a sparingly soluble salt.

Controlled- or sustained-release formulations of a pharmaceutical composition of the present disclosure can be made using conventional technology. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions.

Suitable controlled-release formulations known to those of ordinary skill in the art, including those described herein, can be readily selected for use with the pharmaceutical compositions of the disclosure. Thus, single unit dosage forms suitable for parenteral or topical administration, such as injectable solutions, gels, creams, and ointments, which are adapted for controlled-release are encompassed by the present disclosure.

Most controlled-release pharmaceutical products have a common goal of improving therapy over that achieved by their non-controlled counterparts. Ideally, the use of an optimally designed controlled-release preparation in medical treatment is characterized by a minimum of therapeutic agent being employed to cure or control the condition in a minimum amount of time. Advantages of controlled-release formulations include extended activity of the therapeutic agent, reduced dosage frequency, and increased patient compliance. In addition, controlled-release formulations can be used to affect the time of onset of action or other characteristics, such as blood level of the therapeutic agent, and thus can affect the occurrence of side effects.

Most controlled-release formulations are designed to initially release an amount of therapeutic agent that promptly produces the desired therapeutic effect, and gradually and continually release of other amounts of therapeutic agent to maintain this level of therapeutic effect over an extended period of time. In order to maintain this constant level of therapeutic agent in the body, the therapeutic agent must be released from the dosage form at a rate that will replace the amount of therapeutic agent being metabolized and excreted from the body.

Controlled-release of an active ingredient can be stimulated by various inducers, for example pH, temperature, enzymes, water, or other physiological conditions or compounds. The term "controlled-release component" in the context of the present disclosure is defined herein as a compound or compounds, including, but not limited to, polymers, polymer matrices, gels, permeable membranes, liposomes, or microspheres or a combination thereof that facilitates the controlled-release of the active ingredient.

In certain embodiments, the formulations of the present disclosure can be, but are not limited to, short-term, rapid-offset, as well as controlled, for example, sustained release, delayed release and pulsatile release formulations.

The term sustained release is used in its conventional sense to refer to a therapeutic agent formulation, e.g., a formulation comprising an inositol phosphate of the present disclosure, that provides for gradual release of a therapeutic agent over an extended period of time, and that can, although not necessarily, result in substantially constant blood levels of a therapeutic agent over an extended time period. The period of time can be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the present disclosure can be administered in the form of microparticles, for example, by injection or in the form of wafers or discs by implantation. In certain aspects, the compounds of the disclosure are administered to a patient, alone or in combination with another pharmaceutical agent, using a sustained release formulation.

The term delayed release is used herein in its conventional sense to refer to a therapeutic agent formulation that provides for an initial release of the therapeutic agent after some delay following therapeutic agent administration. The delay may be from about 10 minutes up to about 12 hours. The term pulsatile release is used herein in its conventional sense to refer to a therapeutic agent formulation that provides release of the therapeutic agent in such a way as to produce pulsed plasma profiles of the therapeutic agent after administration. The term immediate release is used in its conventional sense to refer to a therapeutic agent formulation that provides for release of the therapeutic agent immediately after administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after therapeutic agent administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after therapeutic agent administration.

Additional formulations and dosage forms of the compositions of the present disclosure include dosage forms as described in U.S. Pat. Nos. 6,340,475, 6,488,962, 6,451,808, 5,972,389, 5,582,837, and 5,007,790; U.S. Patent Applications Nos. 20030147952, 20030104062, 20030104053, 20030044466, 20030039688, and 20020051820; PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757, all of which are incorporated herein by reference in their entireties.

Medicaments according to the disclosure are manufactured by methods known in the art, especially by conventional mixing, coating, granulating, dissolving or lyophilizing.

The present disclosure also provides a compound or a combination of compounds or pharmaceutical formulation according to any of the above aspects of the disclosure, in the broadest definition given, or as specified in any of the aspects presented above, for use as a medicament.

The present disclosure also provides a compound or combination of compounds or pharmaceutical formulation according to any of the above aspects of the disclosure, in the broadest definition given, or as specified in any of the aspects presented above, for use in the treatment and/or prevention of a disease or condition disclosed herein.

The present disclosure also provides a compound or combination of compounds or pharmaceutical formulation according to any of the above aspects of the disclosure, in the broadest definition given, or as specified in any of the aspects presented above, for the manufacture of a medicament for the prevention and/or treatment of a disease or condition disclosed herein.

VI. Indications

The methods, compositions, pharmaceutical compositions and formulations, articles of manufacture and kits comprising inositol phosphates of the present disclosure disclosed herein, can be used to treat and/prevent ectopic calcifications, and in particular cutaneous or subcutaneous calcification such as calciphylaxis calcifications, and/or the consequences thereof in a subject in need thereof.

Cutaneous and subcutaneous calcifications (in general referred to as ectopic calcifications) are related to the pathological crystallization of calcium and arise as complications in numerous diseases. Ectopic calcifications can be classified into dystrophic, metastatic, idiopathic, or iatrogenic calcifications, or into calciphylaxis.

Dystrophic calcifications result from local tissue abnormalities and grow in spite of normal plasma calcium and phosphorus levels. The main diseases that can develop due to these calcifications are: connective tissue diseases (scleroderma, CREST syndrome, juvenile dermatomyositis, lupus), cutaneous and subcutaneous infections (panniculitis), skin tumors (in particular pilomatricoma), certain congenital diseases (Elher-Danlos disease, Werner's syndrome, pseudo xanthoma elasticum).

Metastatic calcifications are the result of a disorder of calcium and phosphate metabolism (hypercalcemia and/or hyperphosphatemia). All diseases that cause these disorders can therefore contribute to the development of calcifications.

Idiopathic calcifications occur without tissue lesions or disorders of calcium and phosphate metabolism. The main known diseases in this group are tumoral calcinosis, scrotal calcifications as well as sub-epidermal calcified nodules.

Iatroqenic calcifications can occur following the injection of calcium or para-aminosalycilic acid. They have also been described following the use of calcium chloride saturated electrodes.

Soft tissue calcifications (e.g., cutaneous or subcutaneous calcifications) can be associated with a disease or pathological condition selected from the group consisting of primary hyperparathyroidism, vitamin D intoxication, milk drinker's syndrome, hypercalcemia, secondary hyperparathyroidism, renal failure, hyperphosphatemia, in particular genetic hyperphosphatemia, scleroderma, dermatomyositis, in particular the juvenile form, mixed connective tissue diseases, lupus, CREST syndrome, Elhers-Danlos syndrome, pseudo xanthoma elasticum, Werner's syndrome, late cutaneous porphyria, pseudo hypoparathyroidism, pseudo pseudo-hypoparathyroidism, (primary or secondary) venous or arterial insufficiency, diabetes, scrotal calcinosis, ossifying myositis, post-traumatic ectopic ossifications and any other disease or pathological condition caused by calcium crystal deposit(s), in particular of hydroxyapatite or calcium pyrophosphate, e.g., calciphylaxis.

An important concept is that various disorders, including those listed in the previous paragraphs, can be treated by preventing, reducing, slowing or stopping the progression of calcification in the presence of uremia. The disease related to calcium disorders, or the calcification induced by said disease, can already be present when administration commences, in order to reduce or stop progression of the disease, or can not yet be present, in order to prevent the appearance or onset of the disease.

Calciphylaxis corresponds to the calcification of small sized blood vessels and of the sub-cutaneous adipose tissue. Calciphylaxis can be treated concurrently with at least the following diseases (i) Hypercalcemia;

(ii) Hyperphosphatemia;

(iii) Secondary and tertiary hyperparathyroidism;

(iv) Hypoparathyroidism; or, (v) Any combination thereof.

Further conditions that can benefit from a treatment with the inositol phosphates of the disclosure are, e.g., peripheral arterial disease, critical limb ischemia, general arterial calcification of infancy, aortic stenosis, atherosclerosis, pseudogout, primary hyperoxaluria and pseudoxanthoma elasticum.

In the context of the present disclosure, "peripheral arterial disease" refers to a narrowing of the peripheral arteries to the legs (most commonly), stomach, arms, and head. Symptoms include intermittent claudication (leg pain when walking which resolves with rest), skin ulcers, bluish skin, cold skin, or poor nail and hair growth.

In the context of the present disclosure, "critical limb ischemia" refers to a severe obstruction of the arteries which markedly reduces blood flow to the extremities and progresses to the point of severe pain and even skin ulcers, sores, or gangrene. Critical limb ischemia is a very severe condition of peripheral artery disease.

In the context of the present disclosure, "pseudogout", also known as "Calcium pyrophosphate dihydrate (CPPD) crystal deposition disease" or "pyrophosphate arthropathy" refers to a rheumatologic disorder believed to be caused by calcium pyrophosphate crystal accumulation in connective tissues, particularly joints such as the knee joint.

In the context of the present disclosure, the term "general arterial calcification of infancy" (GACI) relates to a disorder affecting the circulatory system that becomes apparent before birth or within the first few months of life, and which is characterized by abnormal calcification of the arteries and thickening of the arterial walls. These changes lead to stenosis and stiffness of the arteries, resulting in heart failure in some affected individuals, with signs and symptoms including difficulty breathing, edema, cyanosis, hypertension and cardiomegaly.

VII. Combination Therapies

The present disclosure also provides combination treatments comprising the administration of an inositol phosphate of the disclosure and at least one additional therapeutic agent. Also provided are combined compositions comprising an inositol phosphate of the disclosure and at least one additional therapeutic agent. Thus, a further aspect of the present disclosure relates to a composition comprising at least one inositol phosphate of the disclosure as described above and another therapeutic agent.

The term "combination therapy" as used herein refers interchangeably to both combination treatments according to the methods and dosages disclosed herein, and to combined compositions. As used herein the term "combined composition" does not imply the components of the combined composition need to be present together. Consequently, the expression implies that the combination is not necessarily a true combination in light of the physical separation of the components thereof. For example, the components in a combined composition can be applied separately, sequentially, or their application can overlap.

In some aspects, the additional therapeutic agent is selected, e.g., from the compositions presented in TABLE 1. In some aspects, a combination therapy can comprise an inositol phosphate of the disclosure and a therapeutic agent from TABLE 1. In other aspects, a combination therapy can comprise an inositol phosphate of the disclosure and more than one therapeutic agent from TABLE 1. When more than one therapeutic agent from TABLE 1 is present in a combination therapy, the therapeutic agents from TABLE 1 can belong to the same indication or to different indications. For example, a combination composition can comprise a treatment (e.g., OPG), a wound healing compound, and a pain management compound.

TABLE 1

| Exemplary therapeutic agents that can be combined with the inositol phosphates of the present disclosure. | |
| --- | --- |
| Indication | Therapeutic agent(s) to combine with compound(s) of the disclosure |
| Treatment | Osteoprotegerin (OPG) |
| | Corticosteroids |
| | Group A (hydrocortisone, hydrocortisone, methylprednisolone, prednisolone, prednisone, triamcinolone) |
| | Group B (amcinonide, budesonide, desonide, fluocinolone acetonide, fluocinonide, halcinonide, triamcinolone acetonide) |
| | Group C (beclometasone, betamethasone, dexamethasone, fluocortolone, halometasone, mometasone) |
| | Group D1 (alclometasone dipropionate, betamethasone dipropionate, betamethasone valerate, clobetasol propionate, clobetasone butyrate, fluprednidene acetate, mometasone furoate) |
| | Group D2 (ciclesonide, cortisone acetate, hydrocortisone aceponate, hydrocortisone acetate, hydrocortisone buteprate, hydrocortisone butyrate, hydrocortisone valerate, prednicarbate, tixocortol pivalate) |
| | Fetuin-alpha |
| | Vitamin K |
| | Protein C |

TABLE 1-continued

| Exemplary therapeutic agents that can be combined with the inositol phosphates of the present disclosure. | |
| --- | --- |
| Indication | Therapeutic agent(s) to combine with compound(s) of the disclosure |
| | Protein S |
| | Gla Protein Matrix (MGP) |
| | Hyperbaric medicine |
| | [1]Cinacalcet CAS [226256-56-0] |
| | [2]Sevelamer CAS [52757-95-6], lanthanum carbonate, sucroferric oxyhydroxide |
| | Bisphosphonates (etidronate, pamidronate), sodium thiosulfate, other C—O—P compounds |
| | Other ectopic calcification inhibitors |
| Wound healing | Gram positive antibiotics (gloxacillin, amoxicillin plus clavulanic acid, piperacillin-tazobactam, daptomycin) |
| | Anaerobic germs antibiotics (metronidazole, clindamycin) |
| Pain management | Analgesics in general that are not easily dialyzed |
| General analgesia | Opioids (buprenorphine, fentanyl, methadone) |
| | GBA analogs (gabapentin) |
| | Central pain modulators (amitriptyline, duloxetine) |
| Pain management | Lidocaine |
| Topical analgesia | Morphine infusion gels |

[1]In patients with calciphylaxis/hyperparathyroidism
[2]In patients with calciphylaxis/hyperphosphatemia Several of the compounds described as additional therapeutic agents change the thermodynamics of the crystallization process by modifying the concentration of the ions present in the structure of the calcium-containing crystal that results in an ectopic calcification. This sub-group includes calcimimetics, phosphate chelators, thiosulfate, or vitamin D.

Calcimimetics allow the calcium and phosphate concentration to be controlled by regulating blood PTH levels. Said compounds include, e.g., cinacalcet, NPS R-467, NPS R-568, and KAI-4169.

In some aspects, the combination composition comprises a vitamin selected from vitamin B, vitamin D, vitamin K or a combination thereof. Although with a different mechanism of action, vitamin D has a similar effect. The vitamin D is preferably selected from the group consisting of calciferol, ergocalciferol (Vitamin D2), cholecalciferol (Vitamin D3), doxercalciferol, paricalcitol alfarol, alpha-calcidol calcidiol, calcitriol, derivatives or pharmaceutically acceptable salts thereof, or any combinations thereof.

Phosphate chelators act by sequestering phosphate thereby reducing the systemic concentration thereof in blood. The phosphate binder can contain a metal or be metal-free. Metal-free chelators include, e.g., sevelamer. Metal-containing chelators include, e.g., various calcium, iron, lanthanum, aluminum and magnesium salts. Thiosulfate is a chelator that reduces the free calcium concentration in blood.

Other compounds (e.g., pyrophosphate, citrate, bisphosphonates, antihypertensives, anticholesteremic agents, vitamin B, or vitamin K) that can be used in combination therapies act against the altered calcium and phosphate metabolism kinetically by attempting to stop the crystallization process or altering bone metabolism by increasing the amount of repressor factors (pyrophosphate, citrate, vitamin B, vitamin K, bisphosphonates) or by reducing the quantity of promoter factors (necrotic remains or organic matter in the case of antihypertensives or lipid deposits in the case of anticholesteremic agents).

In some aspects, the bisphosphonate can contain nitrogen or be nitrogen-free. In some aspects, the bisphosphonate can be selected from the group consisting of etidronate, alendronate, risedronate, zoledronate, tiludronate, pamidronate, monidronate, neridronate, pamidronate, olpadronate, clodronate, ibandronate, and combinations thereof.

In some aspects, the combination therapy can comprises an anticholesteremic agent selected from the group consisting of statins, fibrates, niacin, acid sequestrants, ezetimibe, lomitapide, phytosterols, orlistat, or combinations thereof.

Compounds that can be also used for the treatment of ectopic calcifications also include those disclosed in U.S. Pat. No. 9,629,872, International Publ. No. WO2017131127, U.S. Pat. Nos. 5,362,886, 4,024,175, and 3,159,581, all of which are herein incorporated by reference in their entireties.

VIII. Articles of Manufacture and Kits

The present disclosure also provides articles of manufacture and kits. Such articles of manufacture and kits can comprise a container (e.g., a box) comprising one or more vials containing a formulation comprising one or more of the inositol phosphates of the present disclosure and/or solvents for their administration according to the methods disclosed herein. A kit or article of manufacture provided according to this disclosure can also comprise brochures or instructions describing the process of administration and dosages disclosed herein. In some aspects, kit or article of manufacture can comprise multiple vials, each one of them containing a single dose. In other aspects, kit or article of manufacture can comprise one or more vials, each one of them comprising more than one dose.

In some aspects, the article of manufacture is a bag containing a solution of an inositol phosphate of the present disclosure. In other aspects, the article of manufacture is a bottle (e.g., a glass bottle or a plastic bottle) containing a solution of an inositol phosphate of the present disclosure. In some aspects, the article of manufacture is a bag containing an inositol phosphate of the present disclosure in powder form for reconstitution in a appropriate solvent. In other aspects, the article of manufacture is a bottle (e.g., a glass bottle or a plastic bottle) containing an inositol phosphate of the present disclosure in powder form for reconstitution in a appropriate solvent.

The kits and articles of manufacture can include instructions for carrying out one or more administrations of the inositol phosphate of the present disclosure according to the methods and dosages disclosed herein.

Instructions included in the kits and articles of manufacture can be affixed to packaging material or can be included as a package insert. While the instructions are typically written or printed materials they are not limited to such. Any medium capable of storing such instructions and communicating them to an end user is contemplated. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

EXAMPLES

Example 1

A Phase 2 Open-Label Single-Arm Study to Assess the Effect of SNF472 on Wound Healing in Subjects with Calciphylaxis

Background

Calciphylaxis in end-stage renal disease is characterized by painful necrotic skin ulcers and high mortality. There are no approved therapies. SNF472, an intravenous formulation of myo-inositol hexaphosphate, selectively inhibits formation and growth of hydroxyapatite crystals, the final common pathway in vascular calcification. This phase 2 study evaluated SNF472 in the treatment of calciphylaxis.

Methods

In this open-label, single-arm study, subjects with calciphylaxis and on hemodialysis received intravenous SNF472 6-9 mg/kg during thrice weekly dialysis for 12 weeks, on top of standard care. The primary endpoint was Bates-Jensen Wound Assessment Tool (BWAT). Pain visual analog scale (VAS), wound quality of life (QoL), and qualitative wound image review were secondary endpoints. Quantitative changes from baseline to week 12 were analyzed for all subjects with multiple imputation; qualitative wound image review was analyzed descriptively for subjects who completed 12 weeks of SNF472 treatment.

Results

Among the 14 subjects who were enrolled and received SNF472, significant improvements from baseline to week 12 were observed for total BWAT score (mean, −8.1; P<0.001), pain VAS (mean, −23.6 mm; P=0.014), and Wound-QoL global score (mean, −0.9; P=0.003). Qualitative wound image review showed improvement for 8 of 11 subjects who completed 12 weeks of treatment. Adverse events and deaths (n=2) were consistent with a hemodialysis population. Eight subjects experienced serious adverse events, none of which were considered related to SNF472.

Conclusions

The results of this phase 2 study indicate that SNF472 is tolerated well and calciphylaxis patients had benefits across multiple parameters, supporting a phase 3 study of SNF472 for calciphylaxis.

Materials and Methods (1) Study Design
This was an open-label, single-arm, repeat-dose phase 2 clinical study at 11 study centers in the United States and England to investigate the effect of SNF472 in patients with calciphylaxis. After screening, eligible subjects were enrolled and received SNF472 intravenously during hemodialysis 3 times weekly for 12 weeks. A follow-up safety visit was conducted 1 week after the last SNF472 dose. SNF472 was administered by slow infusion for 2.5 to 4 hours using the dialysis system. The dose of SNF472 administered at each session was 400, 450, 700, or 900 mg, based on the subject's dry body weight at screening (50 to <66 kg, 66 to <81 kg, 81 to <111 kg, or 111 to 150 kg, respectively). SNF472 treatment was added to standard of care in accordance with the study center's standard procedures.

(2) Subjects
Eligible subjects were men or women ≥18 years of age who were either newly diagnosed with calciphylaxis or had recurrent calciphylaxis that had been dormant with no skin lesion involvement for at least 90 days from study start (new or recurrent diagnosis was made within 5 weeks of study start). Subjects were required to be receiving maintenance hemodialysis and have pain (at least minimal) on the pain VAS or they were receiving analgesics stronger than non-steroidal anti-inflammatory drugs.

Key exclusion criteria were pregnancy, body weight above 150 kg, body mass index>35 $kg/m^2$ and central (abdominal) ulcers, bisphosphonate treatment within 12 months before entering into the study, severe illness with expected survival ≥6 months, and scheduled parathyroidectomy. Subjects signed written informed consent to participate. This study was conducted in accordance with the ethical principles that originate from the Declaration of Helsinki and that are consistent with International Council for Harmonisation Guidelines on Good Clinical Practice and regulatory requirements.

(3) Assessments
Investigators documented the severity of the primary lesion (the largest one) with the BWAT (Bates-Jensen & Sussman "Tools to measure wound healing." In: Wound Care: A collaborative practice manual for health professionals. Edited by SUSSMAN, C., BATES-JENSEN, B., Philadelphia, PA, Lippincott Williams & Wilkins, 2012, pp 131-161) at weeks 1, 2, 4, 6, 8, 10, 12, and 13 (follow-up). The BWAT uses a scale of 1 (best) to 5 (worst) for each of 13 items: size, depth, edges, undermining or pockets, necrotic tissue type, necrotic tissue amount, exudate type, exudate amount, surrounding skin color, peripheral tissue edema, peripheral tissue induration, granulation tissue, epithelialization. The total BWAT score was the sum of these individual scores, with a possible range from 13 to 65. Two additional items (location and shape) were not scored.

At the same visits as the BWAT assessments, subjects recorded the intensity of wound pain, using a VAS from 0 (no pain) to 100 (worst possible pain). At weeks 1, 6, and 12, subjects completed the Wound-QoL questionnaire containing 17 questions about impairment of QoL that are coded from 0 (not at all) to 4 (very much) (Augustin (2017), supra).

In addition to a global score, other items can be used to calculate subscale scores for impairment of the body (items 1-5), psyche (items 6-10), and everyday life (items 11-16).

Wound images were obtained for each subject at baseline and every 2 weeks until week 12. Two reviewers reviewed each image and discussed individual cases if there was discordance between their assessments. In the first step, baseline and week 12 images for each subject were randomly labeled "A" and "B" to blind the reviewers. The blinded reviewers determined which was worse, or if both were the same. In the second step, the reviewers examined all images, without blinding, and rated the wound as worsened, improved, or no change from baseline to each visit.

Safety assessments included treatment-emergent adverse events at any time; ECG at weeks 1, 6, 12, and 13 (follow-up); and clinical laboratories at screening, weeks 1, 6, 12, and 13 (follow-up). Blood sampling for pharmacokinetics occurred at day 1 and week 12 day 5.

(4) Statistical Analysis

The primary efficacy endpoint was the absolute change in total BWAT score from baseline to week 12 for the primary lesion. Secondary efficacy endpoints for wound healing were absolute change from baseline in BWAT total and component scores by visit and qualitative change from baseline in wound images. Other secondary efficacy endpoints were absolute change from baseline by visit in the pain VAS score and absolute change from baseline at weeks 6 and 12 in QoL global score and QoL subscale scores.

The primary analysis set for efficacy was the intention-to-treat population, which included subjects who received at least one dose of SNF472 and had at least one postbaseline efficacy measurement. The primary endpoint and quantitative secondary endpoints were analyzed using paired Student's t-tests. Absolute change from baseline was assessed with a multiple imputation method for missing data.

Sensitivity analyses of quantitative endpoints in the intention-to-treat population used the last-observation-carried-forward method and no imputation (observed cases). Additional sensitivity analyses of quantitative endpoints used the per-protocol population of subjects who received at least 75% of SNF472 doses and did not violate the protocol in a way that might have affected the evaluation of the effect of the study drug. Absolute change in quantitative endpoints from baseline to week 12 were also assessed for subgroups based on sodium thiosulfate use at baseline, using multiple imputation in the intention-to-treat population. Imaging results were summarized using descriptive statistics.

Analyses of pharmacokinetic data included all subjects who received at least one dose of SNF472 and for whom the primary pharmacokinetic parameter (postdose SNF472 concentration) could be determined. Descriptive statistics were presented by visit and time point. Accumulation from day 1 to week 12 was assessed by comparing the difference in postdose concentrations between the visits. Accumulation was declared if the 90% CI of the difference did not include the value 0.

Safety analyses included all subjects who received at least one dose of SNF472. Subject incidences of adverse events and serious adverse events were summarized descriptively. For each 12-lead ECG variable, the absolute change from the predose to postdose measurement at each visit and the absolute change from baseline to all other predose measurements were summarized descriptively.

Results (1) Subject Disposition

All 14 subjects who were enrolled in the study received at least one dose of SNF472 and were included in efficacy (intention-to-treat), safety, and pharmacokinetics analyses. Eleven (78.6%) subjects completed the study and were included in per-protocol analyses (TABLE 2).

TABLE 2

Subject disposition (intention-to-treat population)

| | All Subjects (n = 14) |
|---|---|
| Completed study/per protocol | 11 (79) |
| Early discontinuation | 3 (21) |

TABLE 2-continued

Subject disposition (intention-to-treat population)

| | All Subjects (n = 14) |
|---|---|
| Reasons for discontinuation: | |
| Subject withdrew consent | 1 (7) |
| Death | 1 (7) |
| Withdrew from dialysis (led to death) | 1 (7) |
| Adverse event | 0 |
| Lost to follow-up | 0 |

Values are n (%).

Reasons for early study discontinuation were withdrawal of subject consent (n=1), death (n=1), and withdrawal from hemodialysis leading to death (n=1).

(2) Baseline Characteristics

The mean (SD) age of study participants was 60.5 (14.1) years (range, 34-90) (TABLE 3).

TABLE 3

Demographics and baseline characteristics

| Parameter | SNF472 (n = 14) |
|---|---|
| Age, yr | 60.5 ± 14.1 |
| Range | 34-90 |
| Years on hemodialysis | 3.8 ± 1.1 |
| Range | 0.03-15 |
| Sex, n (%) | |
| Female | 11 (78.6) |
| Race, n (%) | |
| White | 10 (71.4) |
| American Indian/Alaska Native, n (%) | 2 (14.3) |
| Black/African American, n (%) | 2 (14.3) |
| Weight, kg | 85.9 ± 23.6 |
| Body mass index, kg/m$^2$ | 31.7 ± 8.4 |
| Intense pain at baseline, n (%) | 13 (92.9) |
| Firm, calcified lesion, n (%) | 10 (71.4) |
| Baseline concomitant medications | |
| Warfarin, n (%) | 2 (14.3)[a] |
| Sodium thiosulfate, n (%) | 11 (78.6)[b] |

Data are mean ± SD unless otherwise stated.
[a] 1 subject stopped warfarin at week 3 and the other subject continued warfarin.
[b] 1 subject stopped sodium thiosulfate at week 2 and other subjects continued sodium thiosulfate; 1 additional subject started sodium thiosulfate at week 7.

The mean (SD) duration of hemodialysis at baseline was 3.8 (1.1) years. Eleven (78.6%) subjects were female and 10 (71.4%) were white. At baseline, sodium thiosulfate was used by 11 (78.6%) subjects and warfarin by 2 (14.3%). One subject each stopped sodium thiosulfate (week 2) and warfarin (week 3) during the study; another subject started sodium thiosulfate on study (week 7). Among the 11 subjects receiving sodium thiosulfate at baseline, the mean length of time on sodium thiosulfate before the first dose of SNF472 was 19 days (range 2-30 days). Ten (71.4%) subjects had firm, calcified subcutaneous tissue surrounding the lesion at baseline. Thirteen (92.9%) subjects reported intense pain at baseline; the subject without intense pain was receiving opioid medications.

(3) Total Bates-Jensen Wound Assessment Tool Score

Figure 1:
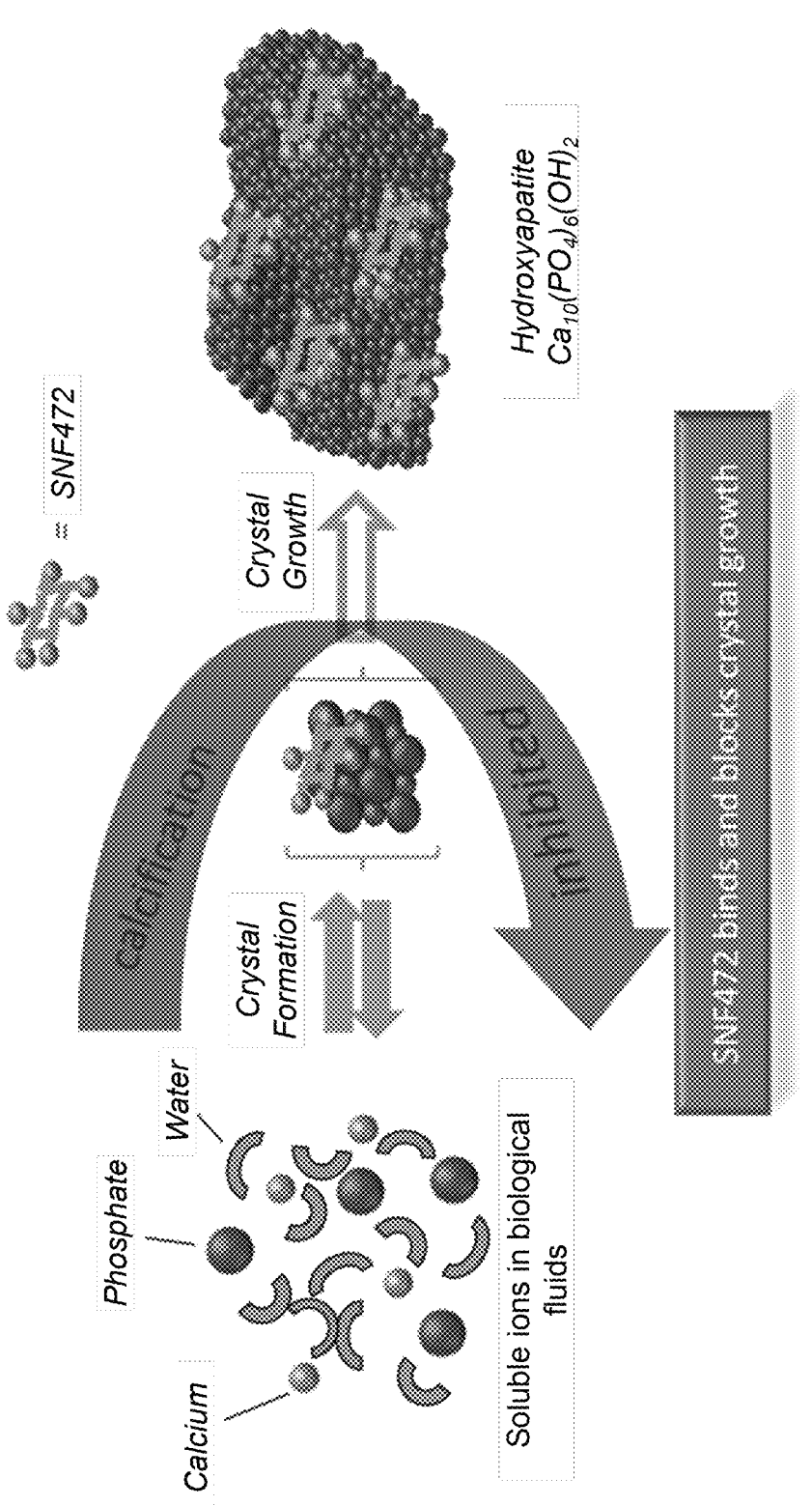
Figure 2A:
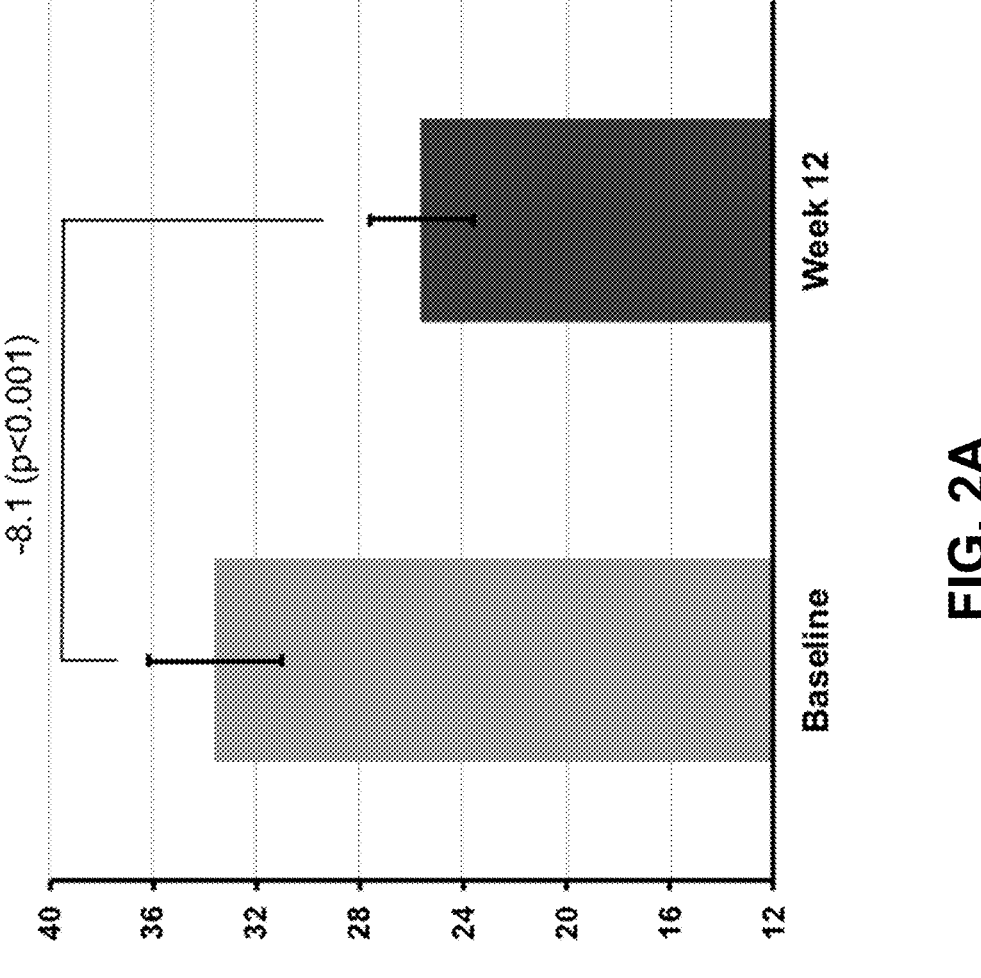
FIG. 2A shows that in the intention-to-treat population with multiple imputation (n=14), SNF472 treatment resulted in a statistically significant improvement in mean total Bates-Jensen Wound Assessment Tool (BWAT) score for the primary lesion from baseline to week 12.

For the primary endpoint of total Bates-Jensen Wound Assessment Tool (BWAT) score for the primary lesion among all subjects, mean (SD) scores improved from 33.6 (9.6) at baseline to 25.6 (7.3) at week 12 (FIG. 2A). SNF472 treatment was associated with statistically significant improvement, with a mean (SD) change of −8.1 (8.5) from baseline to week 12 (95% CI, −12.7 to −3.4; P<0.001; TABLE 4).

TABLE 4

| | Baseline (n = 14) | Week 12 (n = 14) | Change (n = 14) |
|---|---|---|---|
| Changes from baseline to week 12 for the primary and secondary quantitative endpoints with SNF472 treatment (intention-to-treat population with multiple imputation) | | | |
| Total BWAT (primary) | | | |
| Mean (SD) | 33.6 (9.6) | 25.6 (7.3) | −8.1 (8.5) |
| 95% CI | | | −12.7, −3.4 |
| P-value | | | <0.001 |
| Median (range) | 34.0 (16, 46) | 26.0 (16, 38) | −6.0 (−28, 1) |
| Pain VAS (mm) (secondary) | | | |
| Mean (SD) | 71.8 (29.2) | 48.1 (28.6) | −23.6 (30.0) |
| 95% CI | | | −42.6, −4.7 |
| P-value | | | 0.015 |
| Median (range) | 81.0 (0, 100) | 54.2 (0, 88) | −11.0 (−80, 17) |
| Wound-QoL global score (secondary) | | | |
| Mean (SD) | 2.44 (0.89) | 1.54 (0.90) | −0.9 (0.87) |
| 95% CI | | | −1.49, −0.31 |
| P-value | | | 0.003 |
| Median (range) | 2.50 (0.6, 3.7) | 1.63 (0.0, 2.9) | −0.79 (−2.5, 0.5) |

BWAT, Bates-Jensen Wound Assessment Tool; VAS, visual analog scale.
Possible scores: total BWAT, 13 (best) to 65 (worst); pain VAS, 0 mm (no pain) to 100 mm (worst possible pain); Wound-QoL, 0 (no impairment) to 4 (very much impairment).

Figure 2B:
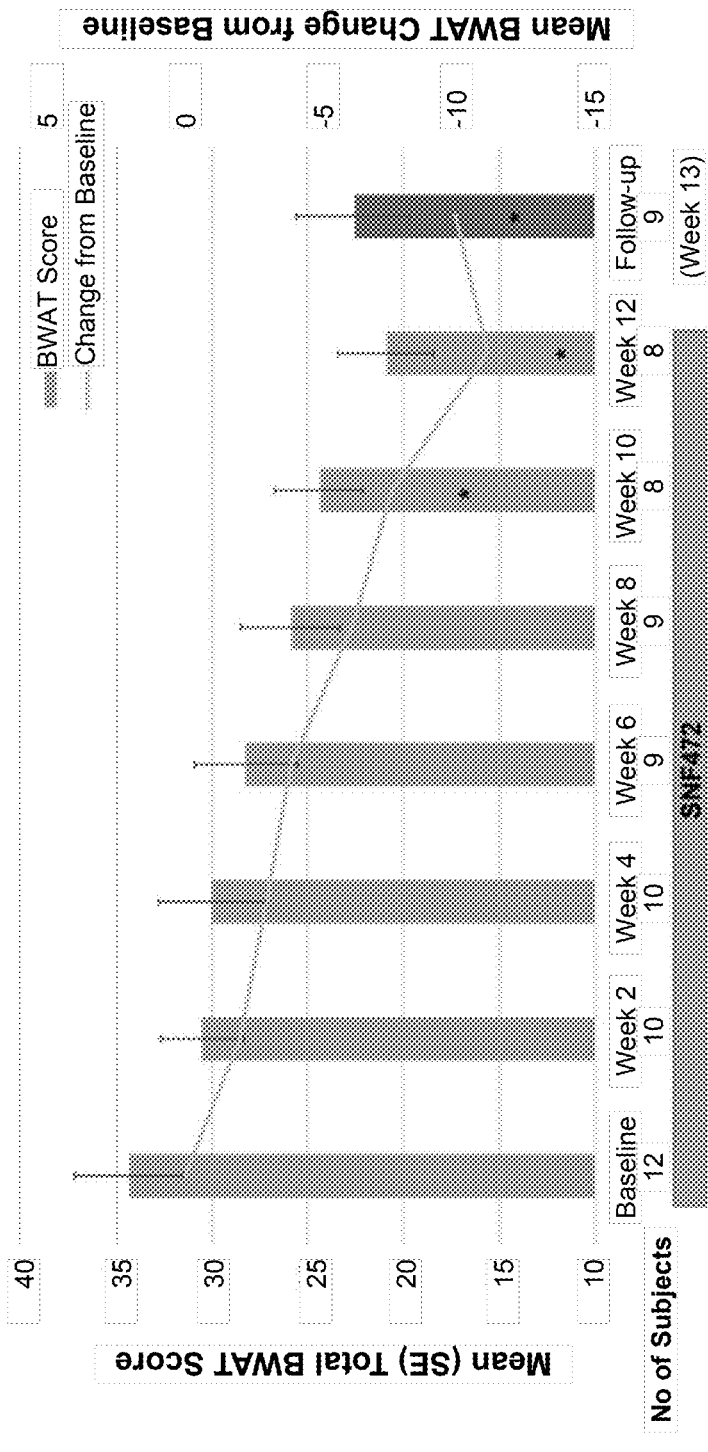
FIG. 2B shows that, using only observed data, SNF472 treatment resulted in progressive improvement in mean total BWAT scores at each visit, with statistically significant improvements at weeks 10 and 12. *p<0.05 for the change from baseline.

Using only observed data, total BWAT score improved progressively, with statistically significant improvements from baseline at weeks 10 and 12 (FIG. 2B). Significant improvements from baseline to week 12 were observed in the BWAT component scores for peripheral tissue induration (mean change, −1.3; P=0.011), skin color surrounding wound (mean change, −1.2; P=0.034), granulation tissue (mean change, −1.2; P=0.024), and exudate amount (mean change, −1.0; P=0.026; FIG. 3). Sensitivity analyses (TABLE 5) showed consistent improvements in BWAT from baseline to week 12 in the per-protocol population with multiple imputation (P=0.002), the intention-to-treat population with observed data (P=0.041), and the intent-to-treat population with last-observation-carried-forward imputation (P=0.021).

(4) Pain

For the secondary endpoint of pain VAS for the primary lesion among all subjects, mean (SD) scores improved from 71.8 (29.2) mm at baseline to 48.1 (28.6) mm at week 12 (FIG. 4A). SNF472 treatment was associated with statistically significant improvement, with a mean (SD) change of −23.6 (30.0) mm from baseline to week 12 (95% CI, −42.6 to −4.7; P=0.015; TABLE 4). Using only observed data, pain VAS score improved significantly from baseline to weeks 6, 8, and 12 (FIG. 4B).

Sensitivity analyses (TABLE 5) showed consistent improvements in pain from baseline to week 12 for the per-protocol population with multiple imputation (P=0.017), the intention-to-treat population with observed data (P=0.020), and the intent-to-treat population with last-observation-carried-forward imputation (P=0.032).

TABLE 5

Sensitivity analyses: change from baseline to week 12 with SNF472 treatment

| | ITT, LOCF Baseline | Week 12 | Change* | ITT, Observed Cases Baseline | Week 12 | Change* | Per Protocol, Multiple Imputation Baseline | Week 12 | Change* |
|---|---|---|---|---|---|---|---|---|---|
| Total BWAT | (n = 14) | (n = 14) | (n = 14) | (n = 12) | (n = 7) | (n = 7) | (n = 11) | (n = 11) | (n = 11) |
| Mean | 33.6 | 27.0 | −6.6 | 34.3 | 22.0 | −8.0 | 32.3 | 23.3 | −8.9 |
| (SD) | (9.6) | (9.0) | (9.5) | (9.6) | (6.9) | (9.6) | (10.5) | (6.4) | (9.5) |
| 95% CI | | | −12.1, −1.2 | | | −16.9, 0.9 | | | −14.6, −3.3 |
| P-value | | | 0.021 | | | 0.071 | | | 0.002 |
| Median (range) | 34.0 (16, 46) | 26.0 (16, 46) | −5.5 (−28, 7) | 34.0 (16, 46) | 18.0 (16, 34) | −6.0 (−28, 1) | 33.0 (16, 46) | 24.1 (16, 34) | −6.0 (−28, 1) |
| Pain VAS | (n = 14) | (n = 14) | (n = 14) | (n = 14) | (n = 10) | (n = 10) | (n = 11) | (n = 11) | (n = 11) |
| Mean | 71.8 | 51.8 | −20.0 | 71.8 | 43.0 | −26.00 | 69.1 | 43.8 | −25.3 |
| (SD) | (29.2) | (31.5) | (31.2) | (29.2) | (31.1) | (35.1) | (31.6) | (29.6) | (33.4) |
| 95% CI | | | −38.0, −2.0 | — | — | −51.1, −0.9 | | | −46.0, −4.5 |
| P-value | | | 0.032 | | | 0.044 | | | 0.017 |

TABLE 5-continued

| Sensitivity analyses: change from baseline to week 12 with SNF472 treatment | | | | | | | | |
| --- | --- | --- | --- | --- | --- | --- | --- | --- |
| ITT, LOCF | | | ITT, Observed Cases | | | Per Protocol, Multiple Imputation | | |
| Baseline | Week 12 | Change* | Baseline | Week 12 | Change* | Baseline | Week 12 | Change* |
| Median (range) Wound-QoL Global | | | | | | | | |
| 81.0 (0, 100) (n = 14) | 60.0 (0, 95) (n = 14) | −8.5 (−80, 17) (n = 14) | 81.0 (0, 100) (n = 14) | 47.5 (0, 85) (n = 14) | −10.0 (−80, 17) (n = 14) | 80.0 (0, 100) (n = 14) | 52.2 (0, 85) (n = 14) | −10.0 (−80, 17) (n = 14) |
| Mean (SD) | | | | | | | | |
| 2.44 (0.89) | 1.76 (1.16) | −0.68 (0.92) | 2.44 (0.89) | 1.29 (1.07) | −1.05 (1.01) | 2.44 (0.89) | 1.54 (0.90) | −0.90 (0.87) |
| 95% CI | | −1.20, −0.15 | | | −1.73, −0.37 | | | −1.49, −0.31 |
| P-value | | 0.016 | | | 0.006 | | | 0.003 |
| Median (range) | | | | | | | | |
| 2.50 (0.6, 3.7) | 1.68 (0.0, 3.9) | −0.50 (−2.5, 0.5) | 2.50 (0.6, 3.7) | 1.29 (0.0, 2.9) | −0.94 (−2.5, 0.5) | 2.50 (0.6, 3.7) | 1.63 (0.0, 2.9) | −0.79 (−2.5, 0.5) |

ITT, intention-to-treat;
LOCF, last observation carried forward.

(5) Quality of Life

For the secondary endpoint of wound quality of life (Wound-QoL) global score, mean (SD) scores improved from 2.44 (0.89) at baseline to 1.54 (0.90) at week 12 (FIG. 5). SNF472 treatment was associated with a statistically significant improvement in mean (SD) change of −0.9 (0.87) from baseline to week 12 (95% CI, −1.49 to −0.31; P=0.003; TABLE 5). Wound-QoL subscales also showed statistically significant mean (SD) improvements from baseline to week 12: body, −0.86 (0.87), P=0.004; and psyche, −1.33 (1.14), P<0.001 (FIG. 5). Improvement in everyday life (mean, −0.65; SD, 0.99) approached statistical significance (P=0.051; FIG. 5).

Sensitivity analyses (TABLE 5) showed consistent improvements in Wound-QoL global score from baseline to week 12 for the per-protocol population with multiple imputation (P=0.016), the intention-to-treat population with observed data (P=0.006), and the intent-to-treat population with last-observation-carried-forward imputation (P=0.003).

(6) Subgroup Analyses by Sodium Thiosulfate Use

Only 2 subjects received SNF472 without sodium thiosulfate, limiting interpretation of the subgroup analyses. However, mean improvements from baseline to week 12 in BWAT and pain VAS were observed in the subjects who received SNF472 without concomitant sodium thiosulfate, including statistically significant improvement for total BWAT score (P=0.003).

(7) Qualitative Wound Assessments

In the unblinded review in which the reviewers knew which visit was associated with each image, they reported that the primary lesion improved qualitatively for 8 of 11 subjects at week 12; many subjects demonstrated qualitative improvement by week 6 of SNF472 treatment (FIG. 6). Representative images for qualitative wound healing assessments at baseline and week 12 are provided in FIG. 7, including 2 examples of wound healing and 1 example of worsening.

(8) Pharmacokinetics

The median (range) postdose plasma SNF472 concentration was 15,845 (1830-411,197) ng/mL at day 1 and 13,679 (2808, 40,192) ng/mL at week 12 day 5. The mean change in postdose SNF472 concentration from day 1 to week 12 day 5 was −2522 ng/mL, indicating that SNF472 did not accumulate with repeated dosing. Plasma SNF472 concentration was in the expected range in all subjects except 1 subject in whom SNF472 was below the limit of quantitation postdose at week 12. The wound also worsened in this subject, as shown in FIG. 7.

(9) Safety

At least one treatment-emergent adverse event was reported for 13 (92.9%) subjects (TABLE 6).

TABLE 6

| Summary of treatment-emergent adverse events (safety analysis set) | |
| --- | --- |
| Category | SNF472 (n = 14) n (%) |
| Any adverse event | 13 (92.9) |
| Adverse events possibly related to SNF472 | 4 (28.6) |
| Adverse events leading to drug discontinuation | 2 (14.3) |
| Worst severity of adverse events | |
| Grade 3 | 5 (35.7) |
| Grade 4 | 0 |
| Grade 5 (fatal) | 2 (14.3)[a] |
| Any serious adverse event | 7 (50.0)[a] |
| Adverse events reported for >1 subject | |
| Arteriovenous fistular thrombosis | 2 (14.3) |
| Cellulitis | 2 (14.3) |
| Diarrhea | 2 (14.3) |
| ECG QT interval prolonged | 2 (14.3) |
| Fluid overload | 2 (14.3) |
| Hypertension | 2 (14.3) |
| Hypoesthesia | 2 (14.3) |
| Nausea | 2 (14.3) |
| Skin lesion | 2 (14.3) |

ECG, electrocardiogram.
[a]Neither of the deaths and none of the other serious adverse events were considered by the investigator to be related to SNF472 treatment.

Adverse events reported for more than one subject were arteriovenous fistula thrombosis, cellulitis, diarrhea, fluid overload, hypertension, hypoesthesia, nausea, prolonged QT interval, and skin lesion (2 [14.3%] subjects each). Most adverse events were mild or moderate in severity. Five (35.7%) subjects had grade 3 (severe) adverse events and no subject had grade 4 (life-threatening) adverse events. Two (14.3%) subjects had grade 5 (fatal) adverse events (cardiorespiratory arrest and cardiogenic shock). The event of cardiorespiratory arrest occurred subsequent to withdrawal from hemodialysis. Aside from these 2 subjects, no subject discontinued study treatment for an adverse event. Seven (50.0%) subjects had serious adverse events. Infections and infestations was the most common System Organ Class of serious adverse events (including cellulitis, gangrene, infection, sepsis, and urinary tract infection in 1 subject each). Other serious adverse events were abdominal wound dehiscence, cardiogenic shock, cardiorespiratory arrest, dry gangrene, fluid overload, hematemesis, hypertensive emergency, and pulmonary edema in 1 subject each. No serious adverse event was considered by the investigator to be related to SNF472 treatment.

No clinically relevant trends in ECG intervals were observed, either from predose to postdose, or between predose assessments on day 1, week 6 day 1, and week 12 day 5. The majority of subjects with assessments had ECG abnormalities that were not clinically significant, either predose or postdose at several assessments. Three subjects had ECG abnormalities that were reported as adverse events: prolonged QT interval (2 subjects) and tachycardia (1 subject). One prolonged QT interval adverse event was considered by the investigator unlikely to be related to SNF472 treatment; it occurred at the follow-up visit 21 days after the last dose of SNF472. The other ECG adverse events were considered possibly related. Each ECG abnormality adverse event was mild to moderate in severity, was asymptomatic, and resolved without treatment.

DISCUSSION

This was the first multicenter, international, prospective, interventional study of a treatment for calciphylaxis. Statistically significant improvement in wound healing for the primary lesion was observed with SNF472 treatment. Statistically significant improvement in pain and Wound-QoL scores also were observed with SNF472 treatment. There was no observed accumulation of SNF472 over time with repeated dosing. SNF472 was generally well tolerated; serious adverse events were consistent with the study population. These results support conducting a phase 3 study of SNF472 for CUA.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments but should be defined only in accordance with the following claims and their equivalents.

The claims in the instant application are different than those of the parent application or other related applications. The Applicant therefore rescinds any disclaimer of claim scope made in the parent application or any predecessor application in relation to the instant application. The Examiner is therefore advised that any such previous disclaimer and the cited references that it was made to avoid, may need to be revisited. Further, the Examiner is also reminded that any disclaimer made in the instant application should not be read into or against the parent application.

What is claimed is:

1. A method of treating or inhibiting the occurrence of aortic stenosis in a human subject in need thereof, comprising administering a dosage of about 5 mg to 10 mg of SNF472 (hexasodium salt of myo-inositol hexaphosphate) per kg per day, wherein the administration of the dosage effectively treats or inhibits the occurrence of aortic stenosis in the subject.

2. The method of claim 1, wherein the dosage is administered daily.

3. The method of claim 2, wherein the dosage is administered daily to the subject for about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or 32 weeks.

4. The method of claim 1, wherein SNF472 is at least 90% pure.

5. The method of claim 1, wherein SNF472 is at least 95% pure.

6. The method of claim 5, wherein SNF472 is at least 99% pure.

7. The method of claim 1, wherein the dose of SNF472 is formulated for injection.

8. The method of claim 7, wherein the injection is an intravenous injection.

9. The method of claim 8, wherein the intravenous injection is a bolus injection.

10. The method of claim 9, wherein the intravenous injection is intravenous infusion.

11. The method of claim 10, wherein the administration is via slow or controlled release.

12. The method of claim 1, wherein the dosage is administered as a single daily dose or as multiple daily doses.

13. The method of claim 1, wherein the dosage is administered between 2, 3, 4, 5, 6, or 7 times per week.

14. The method of claim 13, wherein the dosage is administered 3 times per week.

15. The method of claim 1, wherein the dosage is administered for 12 weeks.

16. The method of claim 1, wherein the dosage is administered 3 days per week for 12 weeks.

17. The method of claim 1, wherein the subject has end-stage renal disease and/or is on hemodialysis.

18. The method of claim 1, wherein the dosage is administered via a dialysis apparatus.

19. The method of claim 18, wherein the dosage is administered before or after the filter of the dialysis apparatus.

20. The method of claim 1, wherein the administration of the dosage to the subject inhibits the formation and/or growth of hydroxyapatite crystals.

21. The method of claim 1, wherein the dosage of about 5 mg to 10 mg of SNF472 (hexasodium salt of myo-inositol hexaphosphate) per kg per day is a unit dose of about 6.0 mg/kg, about 7.0 mg/kg, about 8.0 mg/kg, about 9.0 mg/kg, about 9.7 mg/kg, or about 10 mg/kg.

\* \* \* \* \*